US005856155A

United States Patent [19]

Li

[11] Patent Number: 5,856,155

[45] Date of Patent: Jan. 5, 1999

[54] COMPOUNDS AND RELATED METHODS FOR MODULATING POTASSIUM ION CHANNELS AND ASSAYS FOR SUCH COMPOUNDS

[75] Inventor: Min Li, Lutherville, Md.

[73] Assignee: The Johns Hopkins University School Of Medicine, Baltimore, Md.

[21] Appl. No.: 606,143

[22] Filed: Feb. 23, 1996

[51] Int. Cl.$^6$ .................................................... C12N 15/63

[52] U.S. Cl. ........................ 435/172.3; 514/44; 536/23.1; 536/23.5; 435/6; 435/7.1; 435/69.1; 435/91.1; 435/91.3; 435/320.1; 435/325; 935/6; 935/62; 935/52; 935/55; 935/22; 935/23

[58] Field of Search .............................. 514/44; 536/23.1, 536/23.5; 935/6, 7.1, 240.1, 62, 52, 55, 22, 23; 435/91.1, 91.3, 325, 172.3, 69.1; 924/93.21

[56] References Cited

U.S. PATENT DOCUMENTS 5,401,629 3/1995 Harpold et al. ............................. 435/6

OTHER PUBLICATIONS

Hopkins et al., *J. Neuroscience,* 14, 1385–1393 (1994).
Scott et al., *Proc. Nat'l. Acad. Sci. (USA),* 91 1637–1641 (1994).
Heinemann et al., *J. Physiology,* 88, 173–180 (1994).
Sewing et al., *Neuron,* 16, 455–463 (1996).
Nakahira et al., *J. Biological Chemistry,* 271, 7084–7089 (1996).
Aldrich, *Current Biology,* 4, 839–840 (1994).
Baldwin et al., *Neuron,* 7, 471–483 (1991).
Butler et al., *Nucleic Acids Res.,* 18, 2173–2174 (1990).
Chevray et al., *Proc. Natl. Acad. Sci. USA,* 89, 5789–5793 (1992).
Drewe et al., *J. Neurosci.,* 12, 538–548 (1992).
Fields et al., *Nature,* 340, 245–246(1989).
Frech et al., *Nature,* 340, 642–645 (1989).
Hoshi et al., *Science,* 250, 533–538 (1990).
Iverson et al., *Proc. Natl. Acad. Sci. USA,* 85, 5723–5727 (1988).
Kamb et al., *Cell,* 50, 405–413 (1987).
Li et al., *Science,* 257, 1225–1230 (1992).
Pongs et al., *EMBO J.,* 7, 1087–1996 (1988).
Rettig et al., *Nature,* 369, 289–294 (1994).
Rhodes et al., *J. Neurosci.,* 15, 5360–5371 (1995).
Roberds et al., *Proc. Natl. Acad. Sci. USA,* 88, 1798–1802 (1991).
Stuhmer et al., *EMBO J.,* 8, 3235–3244 (1989).
Tempel et al., *Science,* 237, 770–775, (1987).
Timpe et al., Neuron, 8, 659–667 (1988).
Xu et al., *J. Biol. Chem.,* 270, 24761–24768 (1995).
Yokoyama et al., *FEBS Lett.,* 259, 37–42 (1989).
Zagotta et al., *Proc. Natl. Acad. Sci. USA,* 86, 7243–7247 (1989).
Rettig et al. Nature. 1994, 369:289–294.
Rhodes et al. J. Neurosci. 1995, 15:5360–5371.
Scott et al. P.N.A.S. 1994, 91:1637–1641.
Kozopas et al. P.N.A.S. 1993, vol. 90:3516–3520.
Herman. Mol. Med. Today. 1995, 73:157–163.
Crystal. Science. 1995, 270:404–409.
Coghlan. New Scientist. 1995, vol. 148, pp. 14–15.
Li. Science. 1992, vol. 257:1225–1230.
Yu et al., Neuron, vol. 16, 441–453, 1996
Moralres et al. (J. Biological Chemistry, vol. 270, 11:6272–6277), 1995.
Majumder et al. (FEBS Letters, 361:13–16 1995).

*Primary Examiner*—Christopher S. F. Low
*Assistant Examiner*—Dave Trong Nguyen
*Attorney, Agent, or Firm*—Leydig, Voit & Mayer, Ltd.

[57] ABSTRACT

A polypeptide consisting essentially of the NAB and linking region of an α-subunit of Shaker-like potassium ion channel which binds to a core region of a β-subunit of said Shaker-like potassium ion channel. A related polypeptide is also provided and consists essentially of the core region of a β-subunit of a Shaker-like potassium ion channel which binds to the NAB and linking region of an α-subunit of said Shaker-like channel. Nucleic acid sequences which encode these polypeptides, vectors containing those sequences, expression systems, hosts cells containing the aforesaid polypeptides, and pharmaceutical formulations of the peptides are also provided.

Other aspects of the invention include methods of modulating the flow of potassium ions through a cell membrane surrounding a cytoplasm by introducing either of the aforesaid polypeptides or exogenous Kvβ2 protein into the cytoplasm of the cell, methods of detecting a molecule that binds to either of the aforesaid polypeptides, and an improved yeast two-hybrid system which utilizes the aforesaid polypeptides.

6 Claims, 37 Drawing Sheets

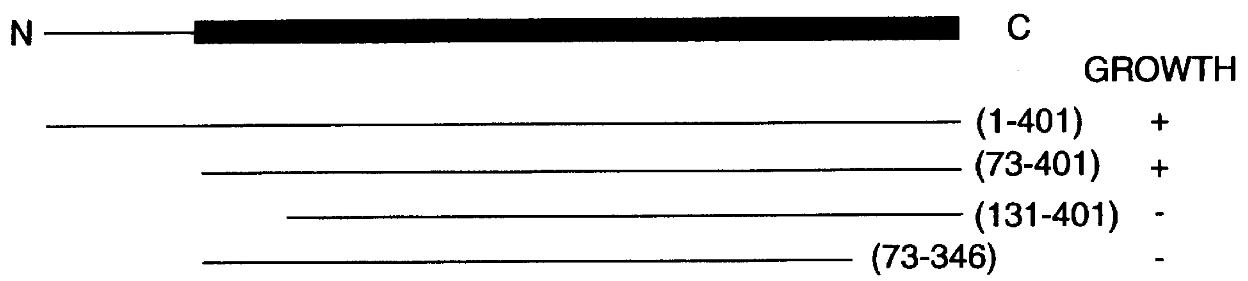

FIG. 4

```
Kvß1 YRNLGKSGLRVSCLGLGTWVTFGGQISDEVAERLMTIAYESGVNLFDTAEVYAAGKAEVILGSIIKKKGWRRSSLVITTK
Kvß2 Y-------------------------T--M--H---L--DN-I----------------V--N-----------------
Kvß3 --------------------------------------------------------------------------------

Kvß1 LYWGGKAETERGLSRKHIIEGLKGSLQRLQLEYVDVVFANRPDSNTPMEEIVRAMTHVINQGMAMYWGTSRWSAMEIMEA
Kvß2 IF---------------------A--E----------------P-----------------------------S------
Kvß3 --------------------------------------------------------------------------------

Kvß1 YSVARQFNMIPPVCEQAEYHLFQREKVEVQLPELYHKIGVGAMTWSPLACGIISGKYGNGVPESSRASLKCYQWLKERIV
Kvß2 --------L---I-------M-------------F-----------------V----DS-I-PY------G-----DK-L
Kvß3 --------------------------------------------------------------------------------

Kvß1 SEEGRKQQNKLKDLSPIAERLGCTLPQLAVAWCLRNEGVSSVLLGSSTPEQLIENLGAIQVLPKMTSHVVNEIDNILRNK
Kvß2 -----R--A---E-QA-------------I---------------A-NA---M--I--------LS-SI-H---S--G--
Kvß3 --------------------------------------------------------------------------------

Kvß1 PYSKKDYRS         [SEQ ID NO:1]
Kvß2 ---------  (85)   [SEQ ID NO:2]
Kvß3 ---------  (100)  [SEQ ID NO:3]
```

FIG. 5

SD, -leu, -trp, +his

SD, -leu, -trp, -his

SD, -leu, -trp, +his

SD, -leu, -trp, -his

SD, -leu, -trp, +his

SD, -leu, -trp, -his

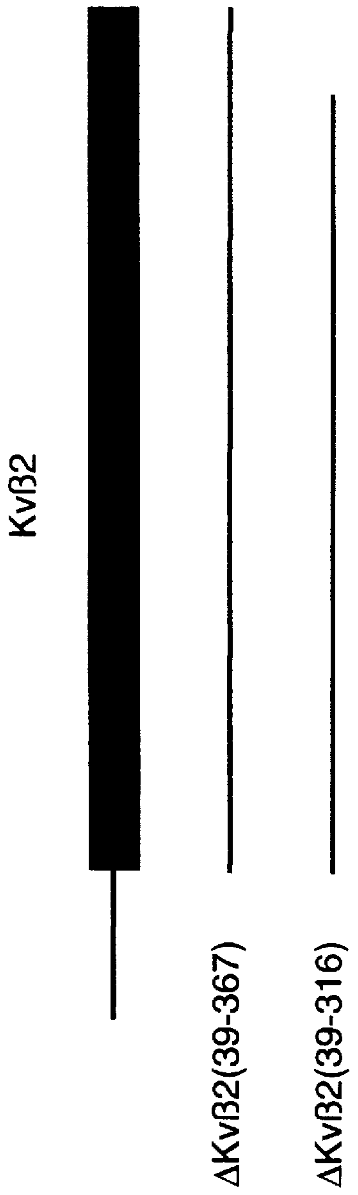
FIG. 9A
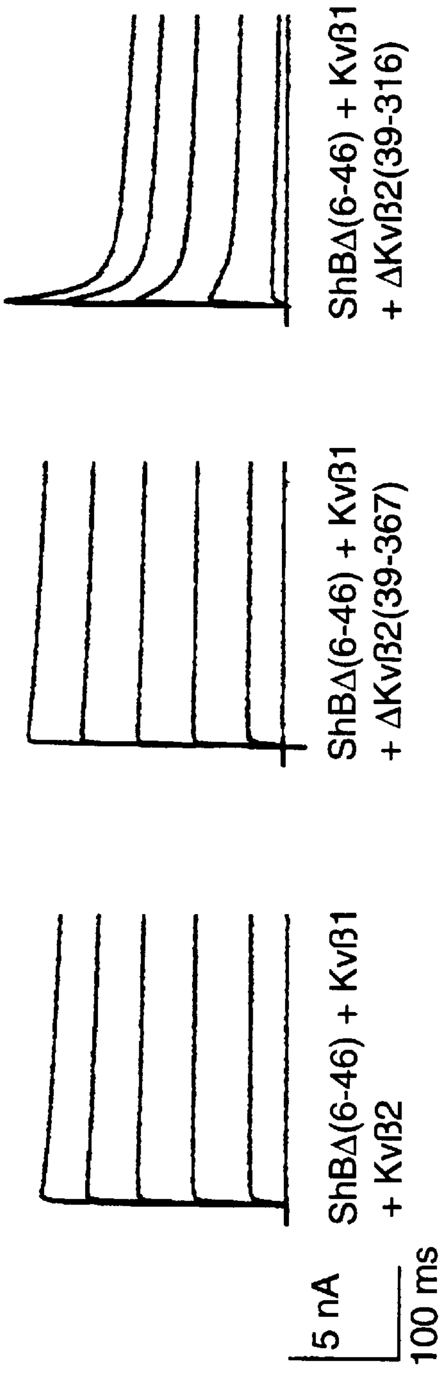
FIG. 9B
FIG. 9C
FIG. 9D

NAB FIG. 10B

| Name | Access Number | Species | Sequence |
|---|---|---|---|
| $NAB_{KV1}$ | | | |
| | M95914 | aplysia | cys-glu-arg-val-val-ile-asn-val-ser-gly- |
| | M94258 | xenopus | cys-glu-arg-val-val-ile-asn-val-ser-gly- |
| xsh2 | M35664 | xenopus | cys-glu-arg-val-val-ile-asn-ile-ser-gly- |
| MK1/MBK1 | M30439 | mouse | cys-glu-arg-val-val-ile-asn-ile-ser-gly- |
| MK1.6 | M96688 | mouse | ser-glu-arg-leu-val-ile-asn-ile-ser-gly- |
| MK2 | M30440 | mouse | cys-glu-arg-val-val-ile-asn-ile-ser-gly- |
| MK3 | M30441 | mouse | gly-glu-arg-val-val-ile-asn-ile-ser-gly- |
| KCNA4 | U03723 | mouse | cys-glu-arg-val-val-ile-asn-val-ser-gly- |
| BK2/RAK | J04731 | rat | cys-glu-arg-val-val-ile-asn-ile-ser-gly- |
| Kv1 | M27158 | rat | his-gln-arg-val-leu-ile-asn-ile-ser-gly- |
| Kv2 | M27159 | rat | ser-glu-arg-leu-val-ile-asn-ile-ser-gly- |
| kv3/RGK5 | M31744 | rat | gly-glu-arg-val-val-ile-asn-ile-ser-gly- |
| RCK1/BK1/RBK1 | X12589 | rat | cys-glu-arg-val-val-ile-asn-ile-ser-gly- |
| RCK2 | X17621 | rat | ser-glu-arg-leu-val-ile-asn-ile-ser-gly- |
| RCK3 | X16001 | rat | gly-glu-arg-val-val-ile-asn-ile-ser-gly- |
| RCK4/RHK1 | X16002 | rat | cys-glu-arg-val-val-ile-asn-val-ser-gly- |
| RCK5/NGK1 | X16003 | rat | gly-glu-arg-val-val-ile-asn-ile-ser-gly- |
| .... | L19740 | dog | his-gln-arg-val-leu-ile-asn-ile-ser-gly- |
| .... | x57033 | cow | cys-glu-arg-val-val-ile-asn-val-ser-gly- |
| HBK2 | X17622 | human | ser-glu-arg-leu-val-ile-asn-ile-ser-gly- |
| HK2 | M60451 | human | his-gln-arg-val-his-ile-asn-ile-ser-gly- |
| HLK3 | M85217 | human | gly-glu-arg-val-val-ile-asn-ile-ser-gly- |
| HPCN1 | M55513 | human | his-gln-arg-val-his-ile-asn-ile-ser-gly- |
| HPCN2/HK1 | M55514 | human | cys-glu-arg-val-val-ile-asn-val-ser-gly- |
| HPCN3/HGK5/KCNA3 | M55515 | human | gly-glu-arg-val-val-ile-asn-ile-ser-gly- |
| KCNA5 | M83254 | human | his-gln-arg-val-his-ile-asn-ile-ser-gly- |
| | L02750 | human | cys-glu-arg-val-val-ile-asn-ile-ser-gly- |
| | L02751 | human | cys-glu-arg-val-val-ile-asn-val-ser-gly- |
| | L02752 | human | cys-glu-arg-val-val-ile-asn-ile-ser-gly- |

| | | | |
|---|---|---|---|
| **$NAB_{Kv2}$** | | | |
| mshab | M64228 | mouse | ser-arg-arg-val-arg-leu-asn-val-gly-gly- |
| CDrk | M77482 | rat | ser-arg-arg-val-lys-ile-asn-val-gly-gly- |
| hDrk1 | X68302 | human | ser-arg-arg-val-arg-leu-asn-val-gly-gly- |
| hkv2.1 | L02840 | human | ser-arg-arg-val-arg-leu-asn-val-gly-gly- |
| **$NAB_{Kv3}$** | | | |
| mkv3.3 | X60796 | mouse | ser-gly-lys-ile-val-ile-asn-val-gly-gly- |
| KSHIIIA | M84202 | rat | asn-glu-arg-val-ile-leu-asn-val-gly-gly- |
| .... | M84210 | rat | ser-gly-lys-ile-val-ile-asn-val-gly-gly- |
| .... | x62841 | rat | ser-glu-lys-ile-ile-ile-asn-val-gly-gly- |
| KCNC1 | S56770 | human | ser-glu-arg-ile-val-ile-asn-val-gly-gly- |
| | M64676 | human | ser-glu-lys-ile-ile-ile-asn-val-gly-gly- |
| **$NAB_{Kv4}$** | | | |
| mshal | M64226 | mouse | asp-glu-val-leu-val-val-asn-val-ser-gly- |
| RK5 | M59980 | rat | asp-ala-leu-ile-val-leu-asn-val-ser-gly- |

NAB

FIG. 10B

NAB FIG. 10B leu-arg-phe-glu-thr-gln-leu-lys-thr-leu-asn-gln-phe-pro-asp-thr-leu-leu-gly-
leu-arg-phe-glu-thr-gln-leu-lys-thr-leu-ala-gln-phe-pro-ser-thr-leu-leu-gly-
leu-arg-phe-glu-thr-gln-leu-lys-thr-leu-ser-gln-phe-pro-glu-thr-leu-leu-gly-
leu-arg-phe-glu-thr-gln-leu-lys-thr-leu-ala-gln-phe-pro-asn-thr-leu-leu-gly-
leu-arg-phe-glu-thr-gln-leu-arg-thr-leu-ser-leu-phe-pro-asp-thr-leu-leu-gly-
leu-arg-phe-glu-thr-gln-leu-lys-thr-leu-ala-gln-phe-pro-glu-thr-leu-leu-gly-
leu-arg-phe-glu-thr-gln-leu-lys-thr-leu-cys-gln-phe-pro-glu-thr-leu-leu-gly-
leu-arg-phe-glu-thr-gln-met-lys-thr-leu-ala-gln-phe-pro-glu-thr-leu-leu-gly-
leu-arg-phe-glu-thr-gln-leu-lys-thr-leu-ala-gln-phe-pro-glu-thr-leu-leu-gly-
leu-arg-phe-glu-thr-gln-leu-gly-thr-leu-ala-gln-phe-pro-asn-thr-leu-leu-gly-
leu-arg-tyr-glu-thr-gln-leu-arg-thr-leu-ser-leu-phe-pro-asp-thr-leu-leu-gly-
leu-arg-phe-glu-thr-gln-leu-lys-thr-leu-cys-gln-phe-pro-glu-thr-leu-leu-gly-
leu-arg-phe-glu-thr-gln-leu-lys-thr-leu-ala-gln-phe-pro-asn-thr-leu-leu-gly-
leu-arg-tyr-glu-thr-gln-leu-arg-thr-leu-ser-leu-phe-pro-asp-thr-leu-leu-gly-
leu-arg-phe-glu-thr-gln-leu-lys-thr-leu-cys-gln-phe-pro-glu-thr-leu-leu-gly-
leu-arg-phe-glu-thr-gln-met-lys-thr-leu-ala-gln-phe-pro-glu-thr-leu-leu-gly-
leu-arg-phe-glu-thr-gln-leu-lys-thr-leu-cys-gln-phe-pro-glu-thr-leu-leu-gly-
leu-arg-phe-glu-ala-gln-leu-gly-thr-leu-ala-gln-phe-pro-asp-thr-leu-leu-gly-
leu-arg-phe-glu-thr-gln-met-lys-thr-leu-ala-gln-phe-pro-glu-thr-leu-leu-gly-
leu-arg-phe-glu-thr-gln-leu-arg-thr-leu-ser-leu-phe-pro-asp-thr-leu-leu-gly-
leu-arg-phe-glu-thr-gln-leu-gly-thr-leu-ala-gln-phe-pro-asn-thr-leu-leu-gly-
val-arg-phe-glu-thr-gln-leu-lys-thr-leu-cys-gln-phe-pro-glu-thr-leu-leu-gly-
leu-arg-phe-glu-thr-gln-leu-gly-thr-gln-ala-gln-phe-pro-asn-thr-leu-leu-gly-
leu-arg-phe-glu-thr-gln-met-lys-thr-leu-ala-gln-phe-pro-glu-thr-leu-leu-gly-
leu-arg-phe-glu-thr-gln-leu-lys-thr-leu-cys-gln-phe-pro-glu-thr-leu-leu-gly-
leu-arg-phe-glu-thr-gln-leu-gly-thr-leu-ala-gln-phe-pro-asn-thr-leu-leu-gly-
leu-arg-phe-glu-thr-gln-leu-lys-thr-leu-ala-gln-phe-pro-asn-thr-leu-leu-gly-
leu-arg-phe-glu-thr-gln-met-lys-thr-leu-ala-gln-phe-pro-glu-thr-leu-leu-gly-
leu-arg-phe-glu-thr-gln-leu-lys-thr-leu-ala-gln-phe-pro-glu-thr-leu-leu-glyleu-ala-his-glu-val-leu-trp-arg-thr-leu-asp-arg-leu-pro-arg-thr-arg-leu-gly-
leu-asn-his-glu-val-leu-trp-arg-thr-leu-asp-arg-leu-pro-arg-thr-arg-leu-gly-
leu-ala-his-glu-val-leu-trp-arg-thr-leu-asp-arg-leu-pro-arg-thr-arg-leu-gly-
leu-ala-his-glu-val-leu-trp-arg-thr-leu-asp-arg-leu-pro-arg-thr-arg-leu-glyval-arg-his-glu-thr-tyr-arg-ser-thr-leu-arg-thr-leu-pro-gly-thr-arg-leu-ala-
thr-arg-his-glu-thr-tyr-arg-ser-thr-leu-lys-thr-leu-pro-gly-thr-arg-leu-ala-
val-arg-his-glu-thr-tyr-arg-ser-thr-leu-arg-thr-leu-pro-gly-thr-arg-leu-ala-
thr-arg-his-glu-thr-tyr-arg-ser-thr-leu-arg-thr-leu-pro-gly-thr-arg-leu-ala-
thr-arg-his-gln-thr-tyr-arg-ser-thr-leu-arg-thr-leu-pro-gly-thr-arg-leu-ala-
thr-arg-his-glu-thr-tyr-arg-ser-thr-leu-arg-thr-leu-pro-gly-thr-arg-leu-alaarg-arg-phe-glu-thr-trp-lys-asn-thr-leu-asp-arg-tyr-pro-asp-thr-leu-leu-gly-
thr-arg-phe-gln-thr-trp-gln-asp-thr-leu-glu-arg-tyr-pro-asp-thr-leu-leu-gly-

NAB
FIG. 10B asn-pro-gln-lys-..............................................
asn-pro-lys-lys-..............................................
asp-pro-lys-lys-..............................................
asn-pro-lys-lys-..............................................
asp-pro-gly-arg-..............................................
asp-pro-lys-lys-..............................................
asp-pro-lys-arg-..............................................
asp-pro-glu-lys-..............................................
asp-pro-lys-lys-..............................................
asp-pro-ala-lys-..............................................
asp-pro-gly-arg-..............................................
asp-pro-lys-arg-..............................................
asn-pro-lys-lys-..............................................
asp-pro-gly-arg-..............................................
asp-pro-lys-arg-..............................................
asp-pro-glu-lys-..............................................
asp-pro-lys-arg-..............................................
asp-pro-ala-lys-..............................................
asp-pro-glu-lys-..............................................
asp-pro-gly-arg-..............................................
asp-pro-ala-lys-..............................................
asp-pro-lys-arg-..............................................
asp-pro-ala-lys-..............................................
asp-pro-glu-lys-..............................................
asp-pro-lys-arg-..............................................
asp-pro-ala-lys-..............................................
asn-pro-lys-lys-..............................................
asp-pro-glu-lys-..............................................
asp-pro-lys-lys-..............................................

NAB

FIG. 10B (continued)

```
lys-leu-arg-asp-cys-asn-thr-his-asp-ser-leu-leu-gln-........................val-
lys-leu-arg-asp-cys-asn-thr-his-glu-ser-leu-leu-glu-........................val-
lys-leu-arg-asp-cys-asn-thr-his-asp-ser-leu-leu-glu-........................val-
lys-leu-arg-asp-cys-asn-thr-his-asp-ser-leu-leu-glu-........................val-

gly-leu-thr-glu-pro-glu-ala-ala-............................................ala-
leu-leu-ala-[SEQ ID NO:38] <- 58 aa.... insert -> ..............................
gly-leu-thr-glu-pro-glu-ala-ala-............................................ala-
trp-leu-ala-asp-pro-asp-gly-gly-gly-arg-pro-glu-ser-asp-gly-gly-gly-ala-gly-ser-
trp-leu-ala-glu-pro-asp-ala-his-............................................ser-
trp-leu-ala-asp-pro-asp-gly-gly-gly-arg-pro-glu-thr-asp-gly-gly-gly-val-gly-ser-

ser-ser-glu-lys-................................................................
ser-ser-glu-arg-................................................................
```

NAB
FIG. 10B (continued)

arg-asn-arg-tyr-tyr-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-val-arg-phe-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-thr-gln-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-leu-his-tyr-phe-asp-pro-leu-arg-asn-glu-tyr-phe-phe-asp-arg-asn-
arg-val-arg-phe-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-val-arg-phe-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-thr-gln-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-leu-arg-tyr-phe-asp-pro-leu-arg-asn-glu-tyr-phe-phe-asp-arg-asn-
arg-thr-gln-tyr-phe-asp-pro-leu-arg-asn-glu-tyr-phe-phe-asp-arg-asn-
arg-val-arg-phe-phe-asp-pro-leu-arg-asn-glu-tyr-phe-phe-asp-arg-asn-
arg-leu-pro-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-leu-pro-tyr-phe-asp-pro-leu-arg-asn-glu-tyr-phe-phe-asp-arg-asn-
arg-thr-gln-tyr-phe-asp-pro-leu-arg-asn-glu-tyr-phe-phe-asp-arg-asn-
arg-met-arg-tyr-phe-asp-pro-val-arg-asn-glu-tyr-phe-phe-asp-arg-asn-
arg-leu-arg-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-
arg-thr-gln-tyr-phe-asp-pro-leu-arg-asn-glu-tyr-phe-phe-asp-arg-asn-
arg-met-arg-tyr-phe-asp-pro-leu-arg-asn-glu-tyr-phe-phe-asp-arg-asn-

NAB

FIG. 10B (continued)

```
·cys-asp-asp-tyr-....ser-leu-glu-asp-asn-glu-tyr-phe-phe-asp-arg-his-
·cys-asp-asp-tyr-....asn-leu-asn-glu-asn-glu-tyr-phe-phe-asp-arg-his-
·cys-asp-asp-tyr-....ser-leu-asp-asp-asn-glu-tyr-phe-phe-asp-arg-his-
·cys-asp-asp-tyr-....ser-leu-asp-asp-asn-glu-tyr-phe-phe-asp-arg-his-

·arg-phe-asp-tyr-....asp-pro-gly-thr-asp-glu-phe-phe-phe-asp-arg-his-
 .........................gly-gly-gly-arg-glu-phe-phe-phe-asp-arg-his-
·arg-phe-asp-tyr-....asp-pro-gly-thr-asp-glu-phe-phe-phe-asp-arg-his-
·ser-gly-ser-ser-gly-gly-gly-gly-gly-cys-glu-phe-phe-phe-asp-arg-his-
·his-phe-asp-tyr-....asp-pro-arg-ala-asp-glu-phe-phe-phe-asp-arg-his-
·ser-gly-thr-ser-....gly-gly-gly-gly-cys-glu-phe-phe-phe-asp-arg-his-

 glu-phe-phe-tyr-....asp-ala-glu-ser-gly-glu-tyr-phe-phe-asp-arg-asp-
 asp-phe-phe-tyr-....his-pro-glu-thr-gln-gln-tyr-phe-phe-asp-arg-asp-
```

NAB

FIG. 10B (continued)

arg-pro-ser-phe-asp-ala-ile-leu-tyr-phe-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-phe-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-ile-arg-arg-pro-val
arg-pro-ser-phe-asp-ala-ile-leu-tyr-tyr-tyr-gln-ser-gly-gly-arg-leu-lys-arg-pro-val
arg-pro-ser-phe-asp-ala-ile-leu-tyr-tyr-tyr-gln-ser-gly-gly-arg-leu-arg-arg-pro-val
arg-pro-ser-phe-asp-gly-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-ile-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-leu-asp-ala-ile-leu-tyr-tyr-tyr-gln-ser-gly-gly-arg-ile-arg-arg-pro-val
arg-pro-ser-phe-asp-ala-ile-leu-tyr-tyr-tyr-gln-ser-gly-gly-arg-leu-lys-arg-pro-val
arg-pro-ser-phe-asp-ala-ile-leu-tyr-tyr-tyr-gln-ser-gly-gly-arg-ile-arg-arg-pro-val
arg-pro-ser-phe-asp-gly-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-lys-arg-pro-val
arg-pro-ser-phe-asp-ala-ile-leu-tyr-tyr-tyr-gln-ser-gly-gly-arg-leu-arg-arg-pro-val
arg-pro-ser-phe-asp-gly-ile-leu-tyr-tyr-tyr-gln-ser-gly-gly-arg-leu-arg-gly-....val
arg-pro-ser-phe-asp-ala-ile-leu-tyr-tyr-tyr-gln-ser-gly-gly-arg-ile-arg-arg-pro-val
arg-pro-ser-phe-asp-gly-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-lys-arg-pro-val
arg-pro-ser-phe-asp-ala-ile-leu-tyr-tyr-tyr-gln-ser-gly-gly-arg-ile-arg-arg-pro-val
arg-pro-ser-phe-asp-gly-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-arg-arg-pro-val
arg-pro-ser-phe-asp-ala-ile-leu-tyr-tyr-tyr-gln-ser-gly-gly-arg-leu-lys-arg-pro-val
arg-pro-ser-phe-asp-ala-ile-leu-tyr-tyr-tyr-gln-ser-gly-gly-arg-leu-arg-arg-pro-val NAB
FIG. 10B (continued)

```
pro-gly-ala-phe-thr-ser-ile-leu-asn-phe-tyr-arg-thr-gly-....arg-leu-his-met-met-glu
pro-gly-ala-phe-thr-ser-ile-leu-asn-phe-tyr-arg-thr-gly-....lys-leu-his-met-met-glu
pro-gly-ala-phe-thr-ser-ile-leu-asn-phe-tyr-arg-thr-gly-....arg-leu-his-met-met-glu
pro-gly-ala-phe-thr-ser-ile-leu-asn-phe-tyr-arg-thr-gly-....arg-leu-his-met-met-glu

pro-gly-val-phe-ala-tyr-val-leu-asn-tyr-tyr-arg-thr-gly-....lys-leu-his-cys-pro-ala
pro-gly-val-phe-ala-tyr-val-leu-asn-tyr-tyr-arg-thr-gly-....lys-leu-his-cys-pro-ala
pro-gly-val-phe-ala-tyr-val-leu-asn-tyr-tyr-arg-thr-gly-....lys-leu-his-cys-pro-ala
pro-gly-val-phe-ala-tyr-val-leu-asn-tyr-tyr-arg-thr-gly-....lys-leu-his-cys-pro-ala
pro-gly-val-phe-ala-his-ile-leu-asn-tyr-tyr-arg-thr-gly-....lys-leu-his-cys-pro-ala
pro-gly-val-phe-ala-tyr-val-leu-asn-tyr-tyr-arg-thr-gly-....lys-leu-his-cys-pro-ala

pro-asp-met-phe-arg-his-val-leu-asn-phe-tyr-arg-thr-gly-....arg-leu-his-cys-pro-arg
pro-asp-ile-phe-arg-his-ile-leu-asn-phe-tyr-arg-thr-gly-........leu-his-tyr-pro-arg
```

NAB

FIG. 10B (continued)

-asn-val-pro-leu-asp-val-phe-ser-glu-glu-ile-lys-phe-tyr-glu-leu-gly-
-asn-val-pro-leu-asp-met-phe-ser-glu-glu-ile-lys-phe-tyr-glu-leu-gly-
-asn-val-pro-leu-asp-ile-phe-ser-glu-glu-ile-arg-phe-tyr-glu-leu-gly-
-asn-val-pro-leu-asp-met-phe-ser-glu-glu-ile-lys-phe-tyr-glu-leu-gly-
-asn-val-pro-leu-asp-ile-phe-met-glu-glu-ile-arg-phe-tyr-gln-leu-gly-
-asn-val-pro-leu-asp-ile-phe-ser-glu-glu-ile-arg-phe-tyr-glu-leu-gly-
-asn-val-pro-ile-asp-ile-phe-ser-glu-glu-ile-arg-phe-tyr-gln-leu-gly-
-asn-val-pro-phe-asp-ile-phe-thr-glu-glu-val-lys-phe-tyr-gln-leu-gly-
-asn-val-pro-leu-asp-ile-phe-ser-glu-glu-ile-arg-phe-tyr-glu-leu-gly-
-asn-val-ser-leu-asp-val-phe-ala-asp-glu-ile-arg-phe-tyr-gln-leu-gly-
-asn-val-pro-leu-asp-ile-phe-met-glu-glu-ile-arg-phe-tyr-gln-leu-gly-
-asn-val-pro-ile-asp-ile-phe-ser-glu-glu-ile-arg-phe-tyr-gln-leu-gly-
-asn-val-pro-leu-asp-met-phe-ser-glu-glu-ile-lys-phe-tyr-glu-leu-gly-
-asn-val-pro-leu-asp-ile-phe-met-glu-glu-ile-arg-phe-tyr-gln-leu-gly-
-asn-val-pro-ile-asp-ile-phe-ser-glu-glu-ile-arg-phe-tyr-gln-leu-gly-
-asn-val-pro-phe-asp-ile-phe-thr-glu-glu-val-lys-phe-tyr-gln-leu-gly-
-asn-val-pro-ile-asp-ile-phe-ser-glu-glu-ile-arg-phe-tyr-gln-leu-gly-
-asn-val-ser-leu-asp-val-phe-ala-asp-glu-ile-arg-phe-tyr-gln-leu-gly-
-asn-val-pro-phe-asp-ile-phe-thr-glu-glu-val-lys-phe-tyr-gln-leu-gly-
-asn-val-pro-leu-asp-ile-phe-leu-glu-glu-ile-arg-phe-tyr-gln-leu-gly-
-asn-val-ser-leu-asp-val-phe-ala-asp-glu-ile-arg-phe-tyr-gln-leu-gly-
-asn-val-pro-ile-asp-ile-phe-ser-glu-glu-ile-arg-phe-tyr-gln-leu-gly-
-asn-val-ser-leu-asp-val-phe-ala-asp-glu-ile-arg-phe-tyr-gln-leu-gly-
-asn-val-pro-phe-asp-ile-phe-thr-glu-glu-val-lys-phe-tyr-gln-leu-gly-
-asn-val-pro-ile-asp-ile-phe-ser-glu-glu-ile-arg-phe-tyr-gln-leu-gly-
-asn-val-ser-leu-asp-val-phe-ala-asp-glu-ile-arg-phe-tyr-gln-leu-gly-
-asn-val-pro-leu-asp-met-phe-ser-glu-glu-ile-lys-phe-tyr-glu-leu-gly-
-asn-val-pro-phe-asp-ile-phe-thr-glu-glu-val-lys-phe-tyr-gln-leu-gly-
-asn-val-pro-leu-asp-ile-phe-ser-glu-glu-ile-arg-phe-tyr-glu-leu-gly-

NAB

FIG. 10B (continued)

```
-glu-met-cys-ala-leu-ser-phe-ser-gln-glu-leu-asp-tyr-trp-gly-ile-asp-
-glu-met-cys-ala-leu-ser-phe-gly-gln-glu-leu-asp-tyr-trp-gly-ile-asp-
-glu-met-cys-ala-leu-ser-phe-ser-gln-glu-leu-asp-tyr-trp-gly-ile-asp-
-glu-met-cys-ala-leu-ser-phe-ser-gln-glu-leu-asp-tyr-trp-gly-ile-asp-

-asp-val-cys-gly-pro-leu-phe-glu-glu-glu-leu-gly-phe-trp-gly-ile-asp-
-asp-val-cys-gly-pro-leu-phe-glu-glu-glu-leu-ala-phe-trp-gly-ile-asp-
-asp-val-cys-gly-pro-leu-phe-glu-glu-glu-leu-gly-phe-trp-gly-ile-asp-
-asp-val-cys-gly-pro-leu-phe-glu-glu-glu-leu-thr-phe-trp-gly-ile-asp-
-asp-val-cys-gly-pro-leu-tyr-glu-glu-glu-leu-ala-phe-trp-gly-ile-asp-
-asp-val-cys-gly-pro-leu-phe-glu-glu-glu-leu-thr-phe-trp-gly-ile-asp-

-gln-glu-cys-ile-gln-ala-phe-asp-glu-glu-leu-ala-phe-tyr-gly-leu-val-
-his-glu-cys-ile-ser-ala-tyr-asp-glu-glu-leu-ala-phe-phe-gly-leu-ile-
```

NAB

FIG. 10B (continued)

ala-ile-phe-ser-val-val-ile-ile-leu-leu-ser-ile-val-ile-phe-cys-leu-glu-[SEQ ID NO:4]
ala-ile-ile-ser-val-met-val-ile-leu-ile-ser-ile-val-ile-phe-cys-leu-glu-[SEQ ID NO:5]
ala-ile-val-ser-val-ser-val-ile-leu-ile-ser-ile-ile-thr-phe-cys-leu-glu-[SEQ ID NO:6]
ala-ile-val-ser-val-met-val-ile-leu-ile-ser-ile-val-ile-phe-cys-leu-glu-[SEQ ID NO:7]
ala-ile-val-ser-val-leu-val-ile-leu-ile-ser-ile-val-ile-phe-cys-leu-glu-[SEQ ID NO:8]
ala-ile-val-ser-val-met-val-ile-leu-ile-ser-ile-val-ser-phe-cys-leu-glu-[SEQ ID NO:9]
ala-ile-val-ser-val-leu-val-ile-leu-ile-ser-ile-val-ile-phe-cys-leu-glu-[SEQ ID NO:10]
ala-ile-val-ser-val-leu-val-ile-leu-ile-ser-ile-val-ile-phe-cys-leu-glu-[SEQ ID NO:11]
ala-ile-val-ser-val-met-val-ile-leu-ile-ser-ile-val-ser-phe-cys-leu-glu-[SEQ ID NO:12]
ala-ile-val-ser-val-leu-val-ile-leu-ile-ser-ile-ile-thr-phe-cys-leu-glu-[SEQ ID NO:13]
ala-ile-val-ser-val-leu-val-ile-leu-ile-ser-ile-val-ile-phe-cys-leu-glu-[SEQ ID NO:14]
ala-ile-val-ser-val-leu-val-ile-leu-ile-ser-ile-val-ile-phe-cys-leu-glu-[SEQ ID NO:15]
ala-ile-val-ser-val-met-val-ile-leu-ile-ser-ile-val-ile-phe-cys-leu-glu-[SEQ ID NO:16]
ala-ile-val-ser-val-leu-val-ile-leu-ile-ser-ile-val-ile-phe-cys-leu-glu-[SEQ ID NO:17]
ala-ile-val-ser-val-leu-val-ile-leu-ile-ser-ile-val-ile-phe-cys-leu-glu-[SEQ ID NO:18]
ala-ile-ala-ile-val-ser-val-leu-val-ile-leu-ile-ser-ile-val-ile-phe-cys-[SEQ ID NO:19]
ala-ile-val-ser-val-met-val-ile-leu-ile-ser-ile-val-ser-phe-cys-leu-glu-[SEQ ID NO:20]
ala-ile-val-ser-val-met-val-ile-leu-ile-ser-ile-val-ser-phe-cys-leu-glu-[SEQ ID NO:21]
ala-ile-val-ser-val-leu-val-ile-leu-ile-ser-ile-val-ile-phe-cys-leu-glu-[SEQ ID NO:22]
ala-ile-val-ser-val-leu-val-ile-leu-ile-ser-ile-val-ile-phe-cys-leu-glu-[SEQ ID NO:23]
ala-ile-ala-ile-val-ser-val-leu-val-ile-leu-ile-ser-ile-ile-thr-phe-cys-[SEQ ID NO:24]
ala-ile-val-ser-val-leu-val-ile-leu-ile-ser-ile-val-ile-phe-cys-leu-glu-[SEQ ID NO:25]
ala-ile-ala-ile-val-ser-val-leu-val-ile-leu-ile-ser-ile-ile-thr-phe-cys-[SEQ ID NO:26]
ala-ile-val-ser-val-leu-val-ile-leu-ile-ser-ile-val-ile-phe-cys-leu-glu-[SEQ ID NO:27]
ala-ile-val-ser-val-leu-val-ile-leu-ile-ser-ile-val-ile-phe-cys-leu-glu-[SEQ ID NO:28]
ala-ile-ala-ile-val-ser-val-leu-val-ile-leu-ile-ser-ile-ile-thr-phe-cys-[SEQ ID NO:29]
ala-ile-val-ser-val-met-val-ile-leu-ile-ser-ile-val-ile-phe-cys-leu-glu-[SEQ ID NO:30]
ala-ile-val-ser-val-leu-val-ile-leu-ile-ser-ile-val-ile-phe-cys-leu-glu-[SEQ ID NO:31]
ala-ile-val-ser-val-met-val-ile-leu-ile-ser-ile-val-ser-phe-cys-leu-glu-[SEQ ID NO:32]

NAB

FIG. 10B (continued)

ile-leu-ala-ile-ile-ser-ile-met-phe-ile-val-leu-ser-thr-ile-ala-leu-ser-leu-[SEQ ID NO:33]
ile-leu-ala-ile-val-ser-ile-leu-phe-ile-val-leu-ser-thr-ile-ala-leu-ser-leu-[SEQ ID NO:34]
ile-leu-ala-ile-ile-ser-ile-met-phe-ile-val-leu-ser-thr-ile-ala-leu-ser-leu-[SEQ ID NO:35]
ile-leu-ala-ile-ile-ser-ile-met-phe-ile-val-leu-ser-thr-ile-ala-leu-ser-leu-[SEQ ID NO:36]

ala-arg-ala-ala-gly-ala-thr-trp-trp-arg-arg-trp-gln-pro-arg-val-trp-ala-[SEQ ID NO:37]
ala-arg-phe-ile-ala-phe-ala-ser-leu-phe-phe-ile-leu-val-ser-ile-thr-thr-[SEQ ID NO:39]
ala-leu-phe-glu-asp-pro-tyr-ser-ser-arg-ala-ala-arg-tyr-val-ala-phe-ala-[SEQ ID NO:40]
ala-ala-arg-val-val-ala-phe-ala-ser-leu-phe-phe-ile-leu-val-ser-ile-thr-[SEQ ID NO:41]
ala-arg-tyr-val-ala-phe-ala-ser-leu-phe-phe-ile-leu-val-ser-ile-thr-thr-[SEQ ID NO:42]
ala-arg-val-val-ala-phe-ala-ser-leu-phe-phe-ile-leu-val-ser-ile-thr-thr-[SEQ ID NO:43]

ala-ala-leu-val-phe-tyr-tyr-val-thr-gly-phe-phe-ile-ala-val-ser-val-[SEQ ID NO:44]
met-ala-leu-val-phe-tyr-tyr-val-thr-gly-phe-phe-ile-ala-val-ser-val-[SEQ ID NO:45]

NAB
FIG. 10B (continued)

glu-asn-ala-phe-glu-arg-tyr-arg-glu-asp-glu-gly-phe-ile-lys-
glu-glu-ala-met-glu-lys-phe-arg-glu-asp-glu-gly-phe-val-lys-
glu-glu-ala-met-glu-ile-phe-arg-glu-asp-glu-gly-phe-ile-lys-
glu-glu-ala-met-glu-lys-phe-arg-glu-asp-glu-gly-phe-ile-lys-
glu-glu-ala-leu-ala-ala-phe-arg-glu-asp-glu-gly-cys-leu-pro-
glu-glu-ala-met-glu-met-phe-arg-glu-asp-glu-gly-tyr-ile-lys-
glu-glu-ala-met-glu-lys-phe-arg-glu-asp-glu-gly-phe-leu-arg-
glu-glu-ala-leu-leu-lys-phe-arg-glu-asp-glu-gly-phe-val-arg-
glu-glu-ala-met-glu-met-phe-arg-glu-asp-glu-gly-tyr-ile-lys-
asp-glu-ala-met-glu-arg-phe-arg-glu-asp-glu-gly-phe-ile-lys-
asp-glu-ala-leu-ala-ala-phe-arg-glu-asp-glu-gly-cys-leu-pro-
glu-glu-ala-met-glu-lys-phe-arg-glu-asp-glu-gly-phe-leu-arg-
glu-glu-ala-met-glu-lys-phe-arg-glu-asp-glu-gly-phe-ile-lys-
asp-glu-ala-leu-ala-ala-phe-arg-glu-asp-glu-gly-cys-leu-pro-
glu-glu-ala-met-glu-lys-phe-arg-glu-asp-glu-gly-phe-leu-arg-
glu-glu-ala-leu-leu-lys-phe-arg-glu-asp-glu-gly-phe-val-arg-
glu-glu-ala-met-glu-lys-phe-arg-glu-asp-glu-gly-phe-leu-arg-
asp-glu-ala-leu-glu-arg-phe-arg-glu-asp-glu-gly-tyr-ile-lys-
glu-glu-ala-leu-leu-lys-phe-arg-glu-asp-glu-gly-phe-val-arg-
asp-glu-ala-leu-ala-ala-phe-arg-glu-asp-glu-gly-cys-leu-pro-
asp-glu-ala-met-glu-arg-phe-arg-glu-asp-glu-gly-phe-ile-lys-
glu-glu-ala-met-glu-lys-phe-arg-glu-asp-glu-gly-phe-leu-arg-
asp-glu-ala-met-glu-arg-phe-gly-glu-asp-glu-gly-phe-ile-lys-
glu-glu-ala-leu-leu-lys-phe-arg-glu-asp-glu-gly-phe-val-arg-
glu-glu-ala-met-glu-lys-phe-arg-glu-asp-glu-gly-phe-leu-arg-
asp-glu-ala-met-glu-arg-phe-arg-glu-asp-glu-gly-phe-ile-lys-
glu-glu-ala-met-glu-lys-phe-arg-glu-asp-glu-gly-phe-ile-lys-
glu-glu-ala-leu-leu-lys-phe-arg-glu-asp-glu-gly-phe-val-arg-
glu-glu-ala-met-glu-met-phe-arg-glu-asp-glu-gly-tyr-ile-lys-

NAB FIG. 10B (continued)

glu-ile-tyr-leu-glu-ser-cys-cys-gln-ala-arg-tyr-his-gln-lys-
glu-ile-tyr-leu-glu-ser-cys-cys-gln-ala-arg-tyr-his-gln-lys-
glu-ile-tyr-leu-glu-ser-cys-cys-gln-ala-arg-tyr-his-gln-lys-
glu-ile-tyr-leu-glu-ser-cys-cys-gln-ala-arg-tyr-his-gln-lysglu-thr-asp-val-glu-ala-cys-cys-trp-met-thr-tyr-arg-gln-his-
glu-thr-asp-val-glu-pro-cys-cys-trp-met-thr-tyr-arg-gln-his-
glu-thr-asp-val-glu-ala-cys-cys-trp-met-thr-tyr-arg-gln-his-
glu-thr-asp-val-glu-pro-cys-cys-trp-met-thr-tyr-arg-gln-his-
glu-thr-asp-val-glu-pro-cys-cys-trp-met-thr-tyr-arg-gln-his-
glu-thr-asp-val-glu-pro-cys-cys-trp-met-thr-tyr-arg-gln-hispro-glu-leu-val-gly-asp-cys-cys-leu-glu-glu-tyr-arg-asp-arg-
pro-glu-ile-ile-gly-asp-cys-cys-tyr-glu-glu-tyr-lys-asp-arg- NAB
FIG. 10B (continued)

glu-glu-glu-lys-pro-leu-pro-gln-asn-glu-phe-gln-arg-arg-val-trp-leu-leu-
glu-glu-glu-arg-pro-leu-pro-asp-lys-glu-phe-gln-arg-gln-val-trp-leu-leu-
glu-glu-glu-lys-pro-leu-pro-arg-asn-glu-phe-gln-arg-gln-val-trp-leu-ile-
glu-glu-glu-arg-pro-leu-pro-glu-lys-glu-tyr-gln-arg-gln-val-trp-leu-leu-
glu-gly-gly-glu-asp-glu-lys-pro-leu-pro-ser-gln-pro-phe-gln-arg-gln-val-
glu-glu-glu-arg-pro-leu-pro-glu-asn-glu-phe-gln-arg-gln-val-trp-leu-leu-
glu-glu-glu-arg-pro-leu-pro-arg-arg-asp-phe-gln-arg-gln-val-trp-leu-leu-
glu-glu-glu-asp-arg-ala-leu-pro-glu-asn-glu-phe-lys-lys-gln-ile-trp-leu-
glu-glu-glu-arg-pro-leu-pro-glu-asn-glu-phe-gln-arg-gln-val-trp-leu-leu-
glu-glu-glu-lys-pro-leu-pro-arg-asn-glu-phe-gln-arg-gln-val-trp-leu-ile-
glu-gly-gly-glu-asp-glu-lys-pro-leu-pro-ser-gln-pro-phe-gln-arg-gln-val-
glu-glu-glu-arg-pro-leu-pro-arg-arg-asp-phe-gln-arg-gln-val-trp-leu-leu-
glu-glu-glu-arg-pro-leu-pro-glu-lys-glu-tyr-gln-arg-gln-val-trp-leu-leu-
glu-gly-gly-glu-asp-glu-lys-pro-leu-pro-ser-gln-pro-phe-gln-arg-gln-val-
glu-glu-glu-arg-pro-leu-pro-arg-arg-asp-phe-gln-arg-gln-val-trp-leu-leu-
glu-glu-glu-asp-arg-ala-leu-pro-glu-asn-glu-phe-lys-lys-gln-ile-trp-leu-
glu-glu-glu-arg-pro-leu-pro-glu-asn-glu-phe-gln-arg-gln-val-trp-leu-leu-
glu-glu-glu-arg-pro-leu-pro-glu-asn-glu-phe-gln-arg-gln-val-trp-leu-leu-
glu-glu-glu-asp-arg-ala-leu-pro-glu-asn-glu-phe-lys-lys-gln-ile-trp-leu-
glu-gly-gly-glu-asp-glu-lys-pro-leu-pro-ser-gln-pro-phe-gln-arg-gln-val-
glu-glu-glu-lys-pro-leu-pro-arg-asn-glu-phe-gln-arg-gln-val-trp-leu-ile-
glu-glu-glu-arg-pro-leu-pro-arg-arg-asp-phe-gln-arg-gln-val-trp-leu-leu-
glu-glu-glu-lys-pro-leu-val-arg-asn-glu-phe-gln-arg-gln-val-trp-leu-ile-
glu-glu-glu-asp-arg-ala-leu-pro-glu-asn-glu-phe-lys-lys-gln-ile-trp-leu-
glu-glu-glu-arg-pro-leu-pro-arg-arg-asp-phe-gln-arg-gln-val-trp-leu-leu-
glu-glu-glu-lys-pro-leu-pro-arg-asn-glu-phe-gln-arg-gln-val-trp-leu-ile-
glu-glu-glu-arg-pro-leu-pro-glu-lys-glu-tyr-gln-arg-gln-val-trp-leu-leu-
glu-glu-glu-asp-arg-ala-leu-pro-glu-asn-glu-phe-lys-lys-gln-ile-trp-leu-
glu-glu-glu-arg-pro-leu-pro-glu-asn-glu-phe-gln-arg-gln-val-trp-leu-leu- LINKING REGION FIG. 10B (continued)

lys-glu-gln-met-asn-glu-glu-leu-lys-arg-glu-ala-glu-thr-leu-arg-glu-arg-
lys-glu-gln-met-asn-glu-glu-leu-arg-arg-glu-ala-glu-thr-met-arg-asp-gly-
lys-glu-gln-met-asn-glu-glu-leu-lys-arg-glu-ala-glu-thr-leu-arg-glu-arg-
lys-glu-gln-met-asn-glu-glu-leu-lys-arg-glu-ala-glu-thr-leu-arg-glu-argarg-asp-ala-glu-glu-ala-leu-asp-ser-phe-glu-ala-pro-asp-ser-ser-ala-asn-
arg-asp-ala-glu-glu-ala-leu-asp-ile-phe-glu-thr-pro-asp-leu-ile-gly-gly-
arg-asp-ala-glu-glu-ala-leu-asp-ser-phe-glu-ala-pro-asp-ser-ser-gly-asn-
arg-asp-ala-glu-glu-ala-leu-asp-ile-phe-glu-ser-pro-asp-gly-gly-gly-gly-
arg-asp-ala-glu-glu-ala-leu-asp-ser-phe-gly-gly-ala-pro-leu-asp-asn-ser-
arg-asp-ala-glu-glu-ala-leu-asp-ile-phe-glu-ser-pro-asp-gly-gly-gly-serlys-lys-glu-asn-ala-glu-arg-leu-ala-glu-asp-glu-glu-ala-glu-gln-ala-gly-
arg-arg-glu-asn-ala-glu-arg-leu-gln-asp-asp-ala-asp-thr-asp-asn-thr-gly- LINKING REGION
FIG. 10B (continued)

phe-glu-tyr-pro-glu-ser-ser-ala-ala-ala-arg-leu-cys-
phe-glu-phe-pro-glu-ser-ser-gly-pro-ala-arg-ile-ile-
phe-glu-tyr-pro-glu-ser-ser-gly-ser-ala-arg-ala-ile-
phe-glu-tyr-pro-glu-ser-ser-gly-pro-ala-arg-val-ile-
trp-leu-leu-phe-glu-tyr-pro-glu-ser-ser-gly-pro-ala-arg-gly-ile-
phe-glu-tyr-pro-glu-ser-ser-gly-pro-ala-arg-ile-ile-
phe-glu-tyr-pro-glu-ser-ser-gly-pro-ala-arg-gly-ile-
leu-phe-glu-tyr-pro-glu-ser-ser-ser-pro-ala-arg-gly-ile-
phe-glu-tyr-pro-glu-ser-ser-gly-pro-ala-arg-ile-ile-
phe-glu-tyr-pro-glu-ser-ser-gly-ser-ala-arg-ala-ile-
trp-leu-leu-phe-glu-tyr-pro-glu-ser-ser-gly-pro-ala-arg-gly-ile-
phe-glu-tyr-pro-glu-ser-ser-gly-pro-ala-arg-gly-ile-
phe-glu-tyr-pro-glu-ser-ser-gly-pro-ala-arg-val-ile-
trp-leu-leu-phe-glu-tyr-pro-glu-ser-ser-gly-pro-ala-arg-gly-ile-
phe-glu-tyr-pro-glu-ser-ser-gly-pro-ala-arg-gly-ile-
leu-phe-glu-tyr-pro-glu-ser-ser-ser-pro-ala-arg-
phe-glu-tyr-pro-glu-ser-ser-gly-pro-ala-arg-ile-ile-
phe-glu-tyr-pro-glu-ser-ser-gly-pro-ala-arg-ile-ile-
leu-phe-glu-tyr-pro-glu-ser-ser-ser-pro-ala-arg-gly-ile-
trp-leu-leu-phe-glu-tyr-pro-glu-ser-ser-gly-pro-ala-arg-gly-ile-
phe-glu-tyr-pro-glu-ser-ser-gly-ser-ala-arg-
phe-glu-tyr-pro-glu-ser-ser-gly-pro-ala-arg-gly-ile-
phe-glu-tyr-pro-glu-ser-ser-gly-ser-ala-arg-
leu-phe-glu-tyr-pro-glu-ser-ser-asp-pro-ala-arg-gly-ile-
phe-glu-tyr-pro-glu-ser-ser-gly-pro-ala-arg-gly-ile-
phe-glu-tyr-pro-glu-ser-ser-gly-ser-ala-arg-
phe-glu-tyr-pro-glu-ser-ser-gly-pro-ala-arg-val-ile-
leu-phe-glu-tyr-pro-glu-ser-ser-ser-pro-ala-arg-gly-ile-
phe-glu-tyr-pro-glu-ser-ser-gly-pro-ala-arg-ile-ile-

LINKING REGION
FIG. 10B (continued)

glu-gly-glu-glu-phe-asp-asn-thr-cys-cys-ala-glu-lys-arg-lys-lys-leu-trp-asp-leu-
glu-gly-glu-glu-phe-asp-asn-thr-cys-cys-pro-glu-lys-arg-lys-lys-leu-trp-asp-leu-
glu-gly-glu-glu-phe-asp-asn-thr-cys-cys-ala-glu-lys-arg-lys-lys-leu-trp-asp-leu-
glu-gly-glu-glu-phe-asp-asn-thr-cys-cys-ala-glu-lys-arg-lys-lys-leu-trp-asp-leuala-asn-ala-asn-ala-gly-gly-ala-his-asp-ala-gly-leu-asp-asp-glu-ala-gly-ala-gly-
asp-pro-gly-asp-asp-glu-asp-leu-gly-gly-lys-arg-leu-gly-ile-glu-asp-ala-ala-gly-
ala-asn-ala-asn-ala-gly-gly-ala-his-asp-ala-gly-leu-asp-asp-glu-ala-gly-ala-gly-
gly-ala-gly-pro-gly-asp-glu-ala-gly-asp-asp-glu-arg-glu-leu-ala-leu-gln-arg-leu-
ala-asp-asp-ala-asp-ala-asp-gly-pro-gly-asp-ser-gly-asp-gly-glu-asp-glu-leu-glu-
gly-ala-gly-pro-ser-asp-glu-ala-gly-asp-asp-glu-arg-glu-leu-ala-leu-gln-arg-leuglu-gly-pro-ala-leu-pro-ala-gly-ser-ser-leu-arg-gln-arg-leu-trp-arg-ala-phe-glu-
glu-ser-ala-leu-pro-thr-met-thr-ala-arg-gln-arg-val-trp-arg-ala-phe-glu-asn-pro- LINKING REGION
FIG. 10B (continued)

leu-glu-lys-pro-asn-ser-ser-val-ala-ala-lys-
leu-glu-lys-pro-asn-ser-ser-val-ala-ala-lys-
leu-glu-lys-pro-asn-ser-ser-val-ala-ala-lys-
leu-glu-lys-pro-asn-ser-ser-val-ala-ala-lysgly-gly-gly-leu-asp-gly-ala-gly-gly-glu-leu-lys-arg-leu-cys-phe-gln-asp-
leu-gly-gly-pro-asp-gly-lys-ser-gly-arg-trp-arg-lys-leu-gln-pro-arg-met-
gly-gly-gly-leu-asp-gly-ala-gly-gly-glu-leu-lys-arg-leu-cys-phe-gln-asp-
gly-pro-his-glu-gly-gly-ser-gly-pro-gly-ala-gly-ser-gly-gly-cys-arg-gly-
met-thr-lys-arg-leu-ala-leu-ser-asp-ser-pro-asp-gly-arg-pro-gly-gly-phe-
gly-pro-his-glu-gly-gly-ala-gly-his-gly-ala-gly-ser-gly-gly-cys-arg-glyasn-pro-his-thr-ser-thr-
his-thr-ser-thr-

LINKING REGION
FIG. 10B (continued)

ala-gly-gly-gly-ala-gly-asp-leu-pro-gly-
trp-ala-leu-phe-glu-asp-pro-tyr-ser-ser-arg-ala-
ala-gly-gly-gly-ala-gly-gly-pro-ala-gly-gly-pro-gly-gly-ala-gly-gly-thr-trp-trp-arg-arg-trp-gln-pro-arg-val-trp-
trp-gln-pro-arg-met-trp-ala-leu-phe-glu-asp-pro-tyr-ser-ser-arg-
trp-arg-arg-trp-gln-pro-arg-ile-trp-ala-leu-phe-glu-asp-pro-tyr-ser-ser-arg-tyr-
trp-gln-pro-arg-met-trp-ala-leu-phe-glu-asp-pro-tyr-ser-ser-arg-ala- LINKING REGION
FIG. 10B (continued)

ala-ile-phe-ser-val-val-ile-ile-leu-leu-ser-ile-val-
ala-ile-ile-ser-val-met-val-ile-leu-ile-ser-ile-val-
ala-ile-val-ser-val-ser-val-ile-leu-ile-ser-ile-ile-
ala-ile-val-ser-val-met-val-ile-leu-ile-ser-ile-val-
ala-ile-val-ser-val-leu-val-ile-leu-ile-ser-ile-val-
ala-ile-val-ser-val-met-val-ile-leu-ile-ser-ile-val-
ala-ile-val-ser-val-leu-val-ile-leu-ile-ser-ile-val-
ala-ile-val-ser-val-leu-val-ile-leu-ile-ser-ile-val-
ala-ile-val-ser-val-met-val-ile-leu-ile-ser-ile-val-
ala-ile-val-ser-val-leu-val-ile-leu-ile-ser-ile-ile-
ala-ile-val-ser-val-leu-val-ile-leu-ile-ser-ile-val-
ala-ile-val-ser-val-leu-val-ile-leu-ile-ser-ile-val-
ala-ile-val-ser-val-met-val-ile-leu-ile-ser-ile-val-
ala-ile-val-ser-val-leu-val-ile-leu-ile-ser-ile-val-
ala-ile-val-ser-val-leu-val-ile-leu-ile-ser-ile-val-
ala-ile-ala-ile-val-ser-val-leu-val-ile-leu-ile-ser-
ala-ile-val-ser-val-met-val-ile-leu-ile-ser-ile-val-
ala-ile-val-ser-val-met-val-ile-leu-ile-ser-ile-val-
ala-ile-val-ser-val-leu-val-ile-leu-ile-ser-ile-val-
ala-ile-val-ser-val-leu-val-ile-leu-ile-ser-ile-val-
ala-ile-ala-ile-val-ser-val-leu-val-ile-leu-ile-ser-
ala-ile-val-ser-val-leu-val-ile-leu-ile-ser-ile-val-
ala-ile-ala-ile-val-ser-val-leu-val-ile-leu-ile-ser-
ala-ile-val-ser-val-leu-val-ile-leu-ile-ser-ile-val-
ala-ile-val-ser-val-leu-val-ile-leu-ile-ser-ile-val-
ala-ile-ala-ile-val-ser-val-leu-val-ile-leu-ile-ser-
ala-ile-val-ser-val-met-val-ile-leu-ile-ser-ile-val-
ala-ile-val-ser-val-leu-val-ile-leu-ile-ser-ile-val-
ala-ile-val-ser-val-met-val-ile-leu-ile-ser-ile-val-

ile-leu-ala-ile-ile-ser-ile-met-phe-ile-val-leu-ser-
ile-leu-ala-ile-val-ser-ile-leu-phe-ile-val-leu-ser-
ile-leu-ala-ile-ile-ser-ile-met-phe-ile-val-leu-ser-
ile-leu-ala-ile-ile-ser-ile-met-phe-ile-val-leu-serala-arg-ala-ala-gly-ala-thr-trp-trp-arg-arg-trp-gln-
ala-arg-phe-ile-ala-phe-ala-ser-leu-phe-phe-ile-leu-
ala-leu-phe-glu-asp-pro-tyr-ser-ser-arg-ala-ala-arg-
ala-ala-arg-val-val-ala-phe-ala-ser-leu-phe-phe-ile-
ala-arg-tyr-val-ala-phe-ala-ser-leu-phe-phe-ile-leu-
ala-arg-val-val-ala-phe-ala-ser-leu-phe-phe-ile-leuala-ala-leu-val-phe-tyr-tyr-val-thr-gly-phe-phe-ile-
met-ala-leu-val-phe-tyr-tyr-val-thr-gly-phe-phe-ile-

ile-phe-cys-leu-glu-[SEQ ID NO:5]
thr-phe-cys-leu-glu-[SEQ ID NO:6]
ile-phe-cys-leu-glu-[SEQ ID NO:7]
ile-phe-cys-leu-glu-[SEQ ID NO:8]
ser-phe-cys-leu-glu-[SEQ ID NO:9]
ile-phe-cys-leu-glu-[SEQ ID NO:10]
ile-phe-cys-leu-glu-[SEQ ID NO:11]
ser-phe-cys-leu-glu-[SEQ ID NO:12]
thr-phe-cys-leu-glu-[SEQ ID NO:13]
ile-phe-cys-leu-glu-[SEQ ID NO:14]
ile-phe-cys-leu-glu-[SEQ ID NO:15]
ile-phe-cys-leu-glu-[SEQ ID NO:16]
ile-phe-cys-leu-glu-[SEQ ID NO:17]
ile-phe-cys-leu-glu-[SEQ ID NO:18]
ile-val-ile-phe-cys-[SEQ ID NO:19]
ser-phe-cys-leu-glu-[SEQ ID NO:20]
ser-phe-cys-leu-glu-[SEQ ID NO:21]
ile-phe-cys-leu-glu-[SEQ ID NO:22]
ile-phe-cys-leu-glu-[SEQ ID NO:23]
ile-ile-thr-phe-cys-[SEQ ID NO:24]
ile-phe-cys-leu-glu-[SEQ ID NO:25]
ile-ile-thr-phe-cys-[SEQ ID NO:26]
ile-phe-cys-leu-glu-[SEQ ID NO:27]
ile-phe-cys-leu-glu-[SEQ ID NO:28]
ile-ile-thr-phe-cys-[SEQ ID NO:29]
ile-phe-cys-leu-glu-[SEQ ID NO:30]
ile-phe-cys-leu-glu-[SEQ ID NO:31]
ser-phe-cys-leu-glu-[SEQ ID NO:32]

thr-ile-ala-leu-ser-leu-[SEQ ID NO:34]
thr-ile-ala-leu-ser-leu-[SEQ ID NO:35]
thr-ile-ala-leu-ser-leu-[SEQ ID NO:36]

pro-arg-val-trp-ala-[SEQ ID NO:37]
val-ser-ile-thr-thr-[SEQ ID NO:39]
tyr-val-ala-phe-ala-[SEQ ID NO:40]
leu-val-ser-ile-thr-[SEQ ID NO:41]
val-ser-ile-thr-thr-[SEQ ID NO:42]
val-ser-ile-thr-thr-[SEQ ID NO:43]

ala-val-ser-val-[SEQ ID NO:44]
ala-val-ser-val-[SEQ ID NO:45]

COMPOUNDS AND RELATED METHODS FOR MODULATING POTASSIUM ION CHANNELS AND ASSAYS FOR SUCH COMPOUNDS

STATEMENT AS TO RIGHTS TO INVENTIONS MADE UNDER FEDERALLY SPONSORED RESEARCH AND DEVELOPMENT

This invention was made with Government support under Grant Number NS33324-01 awarded by the National Institutes of Health. The Government may have certain rights in this invention.

TECHNICAL FIELD OF THE INVENTION

The present invention relates to compounds and related methods for modulating Shaker-like potassium ion channel activity, and assays for identifying such compounds.

BACKGROUND OF THE INVENTION

Potassium ion ($K^+$) channels comprise a diverse family of membrane proteins that regulate action potentials, cardiac pacemaking, and neurotransmitter release in excitable tissues. In non-excitable tissues, these channels play important roles in hormone secretion, cell proliferation, cell volume regulation, and lymphocyte differentiation. These diverse and significant potassium channel functions have stimulated researchers to investigate potassium channels at the molecular level.

As a result of this research, it was found that a functional potassium channel has four identical and/or homologous polypeptides, generally referred to as α-subunits, that together form a central conduction pore, or channel, for potassium ions. As there are many types of α-subunits, the aforesaid functional diversity of the potassium channels arises primarily from the particular combination of α-subunits present in a particular potassium channel.

Another significant influence on the function of potassium channels is the regulatory interactions of the α-subunits with another type of polypeptide, a hydrophilic polypeptide commonly referred to as β-subunit. Thus, a combination of the particular α-subunits in a particular potassium ion channel, and the interaction of that channel with a β-subunit, allows individual cells to acquire their own characteristic potassium current properties.

One well-known type of potassium ion channel is a Shaker-like channel. These channels are distinguished from other types of potassium channels by the presence of an α-subunit having a hydrophobic core region composed of six transmembrane spanning domains (S1 to S6) flanked by cytoplasmic amino ($NH_2$)— and carboxyl(COOH)-terminal domains. The α-subunits present in the Shaker-like channels are encoded by one or more α-subunit genes. These genes have been divided into at least five subfamilies: Kv1 (Shaker), Kv2(Shab), Kv3 (Shaw), Kv4 (Shal), and Kv5.

One limitation on the structure of Shaker-like potassium ion channels is that α-subunits can only form channels with other α-subunits that were expressed using a gene from the same subfamily. In conducting systematic binding studies to investigate this phenomenon, it was found that there exists a highly conserved region within the $NH_2$-terminal domain of each Shaker-like α-subunit that mediates this subfamily-specific association. This conserved region is commonly referred to as the $NH_2$-terminal A and B box (NAB) (Drewe et al., *J. Neurosci.,* 12, 538–548 (1992), see also Aldrich *Current Biology,* 4, 839–840 (1994). Thus, due to their homology, the NAB's were determined to be the region of the α-subunits that enabled certain other α-subunits to associate with one another and thereby provide a basis for the number of functionally-diverse potassium channels.

While the interaction between the α-subunits with one another has been studied, the information regarding the impact of the differing α-subunit combinations on potassium channel properties remains limited. This lack of information is even greater with respect to the regulation of potassium channels by the β-subunits. The β-subunits were originally identified in membrane preparations from bovine brain as soluble proteins, and this discovery has led to the isolation of genes that encode two such β-subunits, Kvβ1 and Kvβ2 (Rettig et al., *Nature,* 369, 289–294 (1994); Scott et al., *Proc. Natl. Acad. Sci. USA,* 91, 1637–1641 (1994)). Although very little is known about the function of β-subunits, recent studies have revealed that a particular β-subunit (that encoded by Kvβ1), when introduced into Xenopus oocytes, functions to help close the ion pathway in one type of potassium ion channel in a relatively rapid manner. This accelerated pathway closure is referred to as N-type inactivation. However, the method by which this β-subunit accomplishes this inactivation is not well understood. Moreover, and more generally, other than as discussed previously, little is known about potassium ion channel regulation at the molecular level, including the existence and identification of component interactions that may play a role in such regulation.

Due to the importance of potassium ion channels in regulating clinically relevant characteristics of human health, such as heart rate, research has focused on identifying compounds which affect the function of potassium ion channels. By way of example, some classes of disorders that may be affected by effective manipulation of Shaker-like potassium ion channels include neurological disorders, tumor driven diseases, metabolic diseases, cardiac diseases, and autoimmune diseases. Examples of disease states and conditions from these and other classes, as well as affected normal body functions, encompass: hypoglycemia, anoxia/hypoxia, renal disease, osteoporosis, hyperkalemia, hypokalemia, hypertension, Addison's disease, abnormal apoptosis, induced apoptosis, clotting, modulation of acetylcholine function, and modulation of monoaminesepilepsy, allergic encephalomyelitis, multiple sclerosis (any demylelinating disease), acute traverse myelitis, neurofibromatosis, cardioplegia, cardiomyopathy, ischemia, ischemia reperfusion, cerebral ischemia, sickle cell anemia, cardiac arrythmias, peripheral monocuropathy, polynucuropathy, Gullain-Barre' Syndrome, peroneal muscular dystrophy, neuropathies, Parkinson's disease, palsies, cerebral palsy, progressive supranuclear palsy, pseudobubar palsy, Huntington's disease, dystonia, dyskinesias, chorea, althetosis, choreothetosis, tics, memory degeneration, taste perception, smooth muscle function, skeletal muscle function, sleep disorders, modulation of neurotransmitters, acute disseminated encephalomyelitis, optic neuromyelitis, muscular dystrophy, myasthenia gravis, multiple sclerosis, and cerebral vasospasm, hypertension, angina pectoris, asthma, congestive heart failure, ischemia related disorders, cardiac dysrhythmias, diabetes, carcinomas, neurocarcinomas, autoimmune-hypertrophy, neuromyotonia (Isaac's Syndrome) muscular disorders associated with drug abuse, and treatment for poisoning. The search for finding such compounds involves tedious, difficult, and/or insensitive biochemical methods that measure either the ability of a compound to bind to an ion channel (e.g., chromatography), or the ability of a compound to alter a physiological response (e.g., voltage clamp recording).

A system that has been used for measuring the interactions of two proteins is the yeast two-hybrid system. In this system, cDNA libraries or other suitable sources of protein coding sequences are expressed individually, in individual cells as fusion proteins with either a DNA-binding domain or a transactivation domain. There are, however, difficulties in using this system with respect to a particular protein of interest. For example, a particular protein to be studied may have a binding region for other proteins which is comprised of non-contiguous polypeptide sequences. In this case, it would be very difficult to identify an appropriate polypeptide to measure the protein-protein interactions. Additionally, one may find that the region of polypeptide to be used in the two hybrid system does not retain a structure similar to that found in the whole protein. Further, the polypeptide selected can be toxic to the host yeast, or can have intrinsic transcriptional activation potential. In each of these cases, the implementation of the yeast two-hybrid system would be difficult. Further, there exists no reliable indicator one may use to predict whether one could expect to encounter the aforementioned problems with respect to a particular polypeptide.

In view of the foregoing problems, there exists a need for compounds and related methods of artificially modulating potassium channels, and for an economical and efficient means of identifying such compounds. The present invention provides such compounds and related methods of modulating Shaker-like potassium ion channels, as well as an assay for identifying such compounds. These and other advantages of the present invention, as well as additional inventive features, will be apparent from the description of the invention provided herein.

BRIEF SUMMARY OF THE INVENTION

In one aspect of the present invention, the particular region of the α-subunit in a Shaker-like potassium ion channel that provides for the β-subunit-mediated regulation of potassium ion flow through the channel was identified. It was also found that the β-subunit formed a bond with this particular region, and that it was through this bonding that the aforesaid regulation was enabled. The particular region of the β-subunit which bonded to the α-subunit and thereby enabled the regulation was also identified.

The present invention therefore provides a polypeptide consisting essentially of the NAB and linking region of an α-subunit of Shaker-like potassium ion channel which binds to a core region of a β-subunit of said Shaker-like potassium ion channel. A related polypeptide is further provided; this polypeptide consisting essentially of the core region of a β-subunit of a Shaker-like potassium ion channel which binds to the NAB and linking region of an α-subunit of said Shaker-like channel. Nucleic acids sequences which encode these polypeptides, vectors containing those sequences, expression systems, hosts cells containing the aforesaid polypeptides, and pharmaceutical formulations of the polypeptides are also provided in other aspects of the present invention.

Another aspect of the present invention comprises a method of modulating the flow of potassium ions through a cell membrane surrounding a cytoplasm. This method comprises introducing either of the aforesaid polypeptides into the cytoplasm of the cell.

A further aspect of this invention comprises a method of identifying, or detecting, a molecule that binds to the NAB and linking region of an α-subunit of Shaker-like potassium ion channel is also provided. This method comprises: (a) contacting a putative NAB and linking region-binding molecule with the NAB and linking region of an α-subunit under conditions sufficient to allow for binding of the putative NAB and linking region-binding molecule and the NAB and linking region of the α-subunit, and (b) determining whether said binding has occurred. A related method is also provided for detecting a molecule that binds to the core region of a β-subunit of Shaker-like potassium ion channel.

Another aspect of the present invention is the use of an improved yeast two-hybrid system. The improvement of this system comprises: (a) a first vector containing nucleic acid sequences encoding a fusion protein of a DNA binding domain and a polypeptide selected from the group consisting of the core region of a β-subunit of a Shaker-like potassium ion channel, the NAB and linking region of an α-subunit of a Shaker-like potassium ion channel, a putative core region of a β-subunit binding polypeptide, and a putative NAB and linking region-binding polypeptide, and (b) a second vector containing nucleic acid sequences encoding a fusion protein of a transactivation domain and a polypeptide selected from the group consisting of the core region of a β-subunit of a Shaker-like potassium ion channel, the NAB and linking region of an α-subunit of a Shaker-like potassium ion channel, a putative core region of a β-subunit-binding polypeptide, and a putative NAB and linking region-binding polypeptide, wherein said first and second vectors do not both contain a putative binding polypeptide or the NAB and linking region of an α-subunit potassium ion channel.

In another aspect of the present invention, it was found that β-subunits may bind to other β-subunits independently of α-subunits of Shaker-like potassium ion channels, and that this further β-subunit to β-subunit bonding, under appropriate conditions, affects the flow of potassium ions through potassium ion channels. In this regard, another aspect of the present invention comprises a method of modulating the flow of potassium ions through a cell membrane surrounding a cytoplasm, the method comprising introducing exogenous Kvβ2 protein or a Kvβ core region polypeptide into the cytoplasm of the cell.

The invention may best be understood with reference to the accompanying drawings and in the following detailed description of the preferred embodiments.

BRIEF DESCRIPTION OF THE DRAWINGS

FIG. 4 depicts deletion mapping of the region in Kvβ1 which binds to NRCK4 wherein a diagram representing the coding sequence of Kvβ1 is shown. The shaded box indicates the core region (a.a. 73–401). Different coding regions as indicated were cloned into the pPC97 vector for the yeast two-hybrid test with pPC86-NRCK4. At the right side of the figure, symbols are used to indicate the viability of the yeast under selective conditions, with a "+" indicating growth, and a "−" indicating no growth.

FIG. 5 depicts an amino acid comparison of the conserved core region of Kvβ1 with those of Kvβ2(a.a. 39–367) and Kvβ3 (a.a. 80–408). Each sequence is listed in alternating fashion such that the top line of each grouping is Kvβ1 [SEQ ID NO:1]. Similarly, the middle lines indicate Kvβ2 [SEQ ID NO:2] and the lower lines are Kvβ3 [SEQ ID NO:3]. A "−" indicates that the amino acid at that position is identical to Kvβ1. The numbers in parentheses indicate the percentage of amino acid identity to Kvβ1. The amino acid positions at which the deletions were made are indicated on the top of Kvβ1 sequence.

FIG. 8B depicts the results of 17 cells positive in Shaker-like currents that were recorded for ShBΔ(6–46).

FIG. 8C depicts the results of 40 cells positive in Shaker-like currents that were recorded for the ShBΔ(6–46)+Kvβ1 transfection.

FIG. 8D depicts the results of 44 cells that were recorded for the ShBΔ(6–46)+Kvβ1+Kvβ2 transfection.

FIG. 9A shows a schematic diagram of Kvβ2 and its truncations which were subcloned and expressed in COS cells. The filled box indicates the C-terminal conserved core region of Kvβ2. The Δkvβ2(39–367) mutant is a deletion of Kvβ2 that contains only the C-terminal core region. The ΔKvβ2(39–316) mutation was constructed by further deleting 51 amino acids from its C-terminus of the core region.

FIG. 9B shows superimposed whole-cell voltage clamp recordings recorded for a typical cell transfected with ShBΔ(6–46)+Kvβ1+ΔKvβ2. Voltage steps are from −77 mV to +33 mV at 20 mV increments.

FIG. 9C shows superimposed whole-cell voltage clamp recordings recorded for a typical cell out of 39 COS cells transfected with ShBΔ(6–46)+Kvβ1+ΔKvβ2(39–367). Voltage steps are from −77 mV to +33 mV at 20 mV increments.

FIG. 9D shows superimposed whole-cell voltage clamp recordings recorded for a typical cell out of 49 COS cells transfected with ShBΔ(6–46)+Kvβ1+ΔKvβ2(39–316). Voltage steps are from −77 mV to +33 mV at 20 mV increments.

FIG. 9E denotes cells transfected with ShBΔ(6–46)+Kvβ1+Kvβ2.

FIG. 9F denotes cells transfected with ShBΔ(6–46)+Kvβ1+)Kvβ2(39–367).

FIG. 9G denotes cells transfected with ShBΔ(6–46)+Kvβ1.

FIG. 9H denotes cells transfected with ShBΔ(6–46)+Kvβ1+)Kvβ2(39–316).

FIG. 10B and 10B (continued) depict an amino acid alignment of Kvα subunits of the Shaker-like potassium ion channel indicating strong homology in the NAB regions and in the S1 transmembrane spanning region.

DESCRIPTION OF THE PREFERRED EMBODIMENTS

The present invention comprises several polypeptides which have been found to affect the regulation of potassium ion flow through Shaker-like potassium ion channels. One of these polypeptides consists essentially of the NAB and linking region of an α-subunit of a Shaker-like potassium ion channel which binds to a core region of a β-subunit of said Shaker-like potassium ion channel.

Figure 10A:
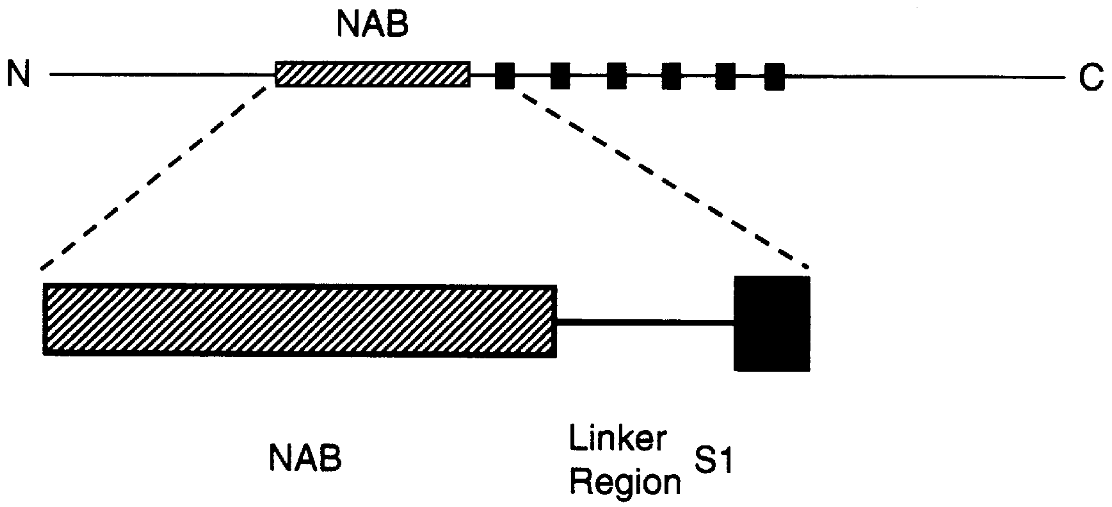
FIG. 10A is a schematic diagram depicting the coding sequence of an α-subunit. The sequences aligned in FIG. 10B are indicated by the detail in FIG. 10A and correspond to the NAB through the S1 transmembrane spanning region, which include the linking region of interest in the present invention.

The NAB portion of the NAB and linking region in α-subunits of Shaker-like potassium ion channels is well-known to those skilled in the art. In each α-subunit, there are six transmembrane spanning regions, usually referred to sequentially as S1 through S6. These spanning regions are most usually identified through comparison of a polypeptide sequence with conserved motifs that indicate a transmembrane spanning region or through biochemical means, often including proteases or flourophores or other suitable reagents, as are known in the field, to determine regions not exposed to aqueous elements of a cell. Since the structure of the Shaker-like potassium ion channels in general is well conserved and the sequences well known an inspection of the sequences is sufficient to identify with reasonable certainty the boundaries of the S1 spanning region. By way of example, such an alignment is provided in FIG. 10B. Thus, the identity of the S1 spanning region can be readily identified by an artisan of ordinary skill (see e.g., Xu et al., *J. Biol. Chem.,* 270, 1–8 (1995)). While there are a number of linking regions which connect the six spanning regions and the NAB together, the linking region that is relevant for purposes of defining the present invention is the linking region between the NAB and S1 spanning region (i.e., the NAB-S1 linking region). Although the existence of this linking region has been known, no function has been attributed to this region prior to the present invention.

In accordance with the present invention, it was surprisingly discovered that the NAB and linking region possessed significant potassium ion regulatory attributes. More specifically, it was found that the NAB and linking region serve as a receptor for a β-subunit core domain. The β-subunits have been known to modulate the function of the potassium ion channel, although the mechanism of that action was, prior to the present invention, very poorly understood.

While there are at least about 60 α-subunits that have been cloned, they can be grouped into five subfamilies. This grouping is based partially upon their sequence homology and further upon the observation that members of one subfamily will only form an oligomer with other α-subunits of the same family. In the present invention, certain β-subunits, namely Kvβ1 and Kvβ2, are disclosed to regulate the Kv1 family of α-subunits and the potassium ion channels composed of the Kv1 family α-subunits. Four β-subunits have been identified, i.e., Kvβ1, Kvβ2, Kvβ3, and most recently Kvβ-HK. Each of these β-subunits share a highly conserved core region which specifies binding to the NAB and linking region of the Kv1 subfamily of α-subunits. Because these Kvβ subunits were isolated from preparations of Kv1 α-subunits from rat brain tissue, it is reasonable to believe that Kvβ subunits specific for other Kv α-subunit subfamilies will be identified. Owing to the high degree of conservation of sequences among all known subunits of Shaker-like potassium ion channels, these additional members of this potassium ion channel family are expected to have homologous features, and the general features contained and described in the present invention will be applicable to newly discovered family members.

The second polypeptide of the present invention is a polypeptide that consists essentially of the core region of a β-subunit of a Shaker-like potassium ion channel which binds to the NAB and linking region of an α-subunit of said Shaker-like channel. In accordance with this aspect of the present invention, it was surprisingly found that it was the core region of β-subunits of Shaker-like potassium ion channels that interacted with the α-subunits of such channels, and in doing so enabled a regulatory response in the potassium channel. Prior to this discovery, it was not known that this region of the β-subunits was responsible for providing such enablement. In other words, prior to this invention it was not known that β-subunits bound directly to α-subunits of Shaker-like potassium ion channels nor what region, if any, was responsible for the mediation of such a response.

The core region of β-subunits, for purposes of the present invention, are those regions of the β-subunit that bind to the NAB and linking region of the α-subunit. By way of example, the amino acid sequences for the core regions of certain of the β-subunits are set forth herein in FIG. 5. These sequences can be easily identified in any β-subunits of a Shaker-like potassium ion channel because there is a significant degree of homology among these sequences. In the example of FIG. 5, the core domains of Kvβ2 and Kvβ3 are shown in alignment with Kvβ1. This alignment discloses an 85% identity for Kvβ2 and a 100% identity for Kvβ3. It is expected that core regions of currently unidentified β-subunits will contain a homology of at least 25%, preferably at least 40%, and most preferably greater than 70%, homology based on the homologies present in the α-subunits of this family and upon the homologies of the β-subunits identified thus far. Owing to the high degree of conservation of sequences among all known subunits of Shaker-like potassium ion channels, these additional members of this potassium channel family are expected to have homologous features and the general features contained and described in the present invention will be applicable to newly discovered family members.

Of course, any number of conservative amino acid substitutions can be made in the sequences of any polypeptide of the present invention. A "conservative amino acid substitution" is an amino acid substituted by an alternative amino acid of similar charge density, hydrophilicity/hydrophobicity, size, and/or configuration (e.g., Val for Ile). A "nonconservative amino acid substitution" is an amino acid substituted by an alternative amino acid of differing charge density, hydrophilicity/hydrophobicity, size, and/or configuration (e.g., Val for Phe). For the purposes of this invention it makes no difference if conservative amino acid changes are introduced into the polypeptide itself or into a nucleic acid sequence encoding said polypeptide. It is also to be expected that a number of non-conservative changes could be introduced without altering the functionality of the polypeptide. This is most easily observed by examining an alignment of the NAB regions from a single subfamily of α-subunits (Xu et al., *J. Biol. Chem.,* 270, 1–8 (1995)). Although the general sequence of the NAB is highly conserved among the different polypeptides of the subfamily, considerable amino acid changes are present which do not preclude the polypeptides from exhibiting the qualities of subfamily members (e.g., heterooligomerizing only with α-subunits of the same family). In a similar fashion, it is expected that a substantial number of amino acid changes can be artificially introduced or introduced by random or natural mutation and still not obstruct the function of the polypeptide. In addition, the length of the polypeptides of the present invention can be altered to the extent the functionality of the polypeptides is not adversely affected. For example, a suitable epitope or a polyhistidine (e.g., $His_6$) can be addended to either end of the polypeptide of the present invention.

As a further aspect of the present invention, there is provided an enriched or isolated nucleic acid comprising a sequence which encodes the polypeptides of the present invention. One of ordinary skill in the art, knowing the regions of the α- and β-subunits which comprise the polypeptides of the present invention, would be readily able to identify the nucleic acid sequence(s) that encode these polypeptides because the genes that encode the α- and β subunits previously have been sequenced or can be readily sequenced by methods known in the art.

Once the relevant nucleic acid sequences of the α- and β-subunits of the present invention are known or isolated, they can be introduced into an appropriate vector to create, clone, or express copies of these subunits. Any vector which is capable of enabling the translation of the nucleic acid sequences into the polypeptides of interest can be used. Vectors, for the purpose of this invention, encompass any plasmid, cosmid, phagemid, bacteriophage, single or double stranded RNA, virus or other vehicle, which contain one or more recombinant or heterologous DNA or RNA coding sequences of interest, which is under the control of a functional promoter and possibly also under the control of an enhancer. Of course, one of ordinary skill in the art will be able to select an appropriate vector to conduct such cloning or expression, this technique being well known in the art. Advantageously, the vector should possess the ability to support high level, low level, or regulatable levels of protein expression. Of course if the supplied nucleic acid is a ribonucleic acid, then it should contain appropriate translation signals and be of suitable stability in order to achieve the desired levels of expression. Appropriate phage and viral vectors include, but are not limited to, lambda (1) bacteriophage, EMBL bacteriophage, simian virus 40, bovine papilloma virus, Epstein-Barr virus, adenovirus, herpes virus, Harvey murine sarcoma virus, murine mammary tumor virus, and Rous sarcoma virus.

Reference to a vector or DNA sequences contained therein as "recombinant" merely acknowledges the linkage of DNA sequences which are not typically conjoined as isolated from nature. A "gene" is any nucleic acid sequence coding for a protein or a nascent mRNA molecule. Whereas a gene comprises coding sequences plus any noncoding (e.g., regulatory sequences), a "coding sequence" does not include any noncoding DNA. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer". Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region or within a transcribed region.

Preferably a vector according to the invention is compatible with the cell into which it is introduced, e.g., is capable of imparting expression on the cell of the polypeptide coding sequence, and may be stably maintained or relatively stably maintained in the host cell. Advantageously, the vector may comprise an origin of replication functional in the cell. When a potassium channel polypeptide coding sequence is transferred (i.e., as opposed to a potassium channel gene having its own promoter), optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant potassium channel polypeptide gene) when the promoter is capable of directing transcription of the coding sequence. In a recombinant vector of the present invention, preferably all the proper transcription (e.g., initiation and termination signals), translation (e.g., ribosome entry or binding site and the like) and processing signals (e.g., splice donor or acceptor sites, if necessary, and polyadenylation signals) are arranged correctly on the vector such that the polypeptide coding sequence will be appropriately transcribed and translated in the cells into which it is introduced. The manipulation of such signals to ensure appropriate expression in host cells is well within the knowledge and expertise of the ordinary skilled artisan. Whereas a potassium channel gene is controlled by (i.e., operably linked to) its own promoter, another promoter, including a constitutive promoter, such as, for instance the adenoviral type 2(Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, including promoters appropriate for expression in prokaryotic cells, can be employed to command expression of the polypeptide coding sequence.

Alternately, a tissue-specific promoter (i.e., a promoter that is preferentially activated in a given tissue and results in expression of a gene product in the tissue where activated) can be used in the vector when employed for expression in a animal host, or in cells, tissues, or organs of the host. Such promoters include, but are not limited to, the elastase I gene control region which is active in pancreatic acinar cells as described by Swift et al., *Cell,* 38, 639–646 (1984), and MacDonald, *Hepatology,* 7, 425–515 (1987). Similarly, a promoter that is selectively activated at a particular developmental stage can be employed, e.g., globin genes are transcribed differentially in embryos and adults. Another option is to use an inducible promoter, such as the IL-8 promoter, which is responsive to TNF, or to use other similar promoters responsive to other factors present in a host or that can be administered exogenously. According to the invention, any promoter or regulatory region can be altered by mutagenesis, so long as it has the desired binding capability and promoter strength.

Optionally, the vector also comprises some means by which the vector or its contained subcloned sequences can be identified and selected. Vector identification and/or selection can be accomplished using a variety of approaches known to those skilled in the art. For instance, vectors containing particular genes or coding sequences can be identified by hybridization, the presence or absence of so-called "marker" gene functions encoded by marker genes present on the vectors, and/or the expression of particular sequences. In the first approach, the presence of a particular sequence in a vector can be detected by polymerase chain reaction or hybridization (e.g., by DNA-DNA hybridization) using primers or probes comprising sequences that are homologous to the relevant sequence. In the second approach, the recombinant vector/host system can be identified and selected based upon the presence or absence of certain marker gene functions such as resistance to antibiotics, thymidine kinase activity, and the like, caused by particular genes encoding these functions present on the vector. In the third approach, vectors can be identified by assaying for a particular gene product encoded by the vector. Such assays can be based on the physical, immunological, or functional properties of the gene product.

A further aspect of the present invention is an expression system. The present inventive expression system consists essentially of a nucleic acid which encodes the polypeptides disclosed herein and transcriptional and translational control elements providing for expression of the nucleic acid. Accordingly, the present invention preferably provides vectors which comprise nucleic acids comprising a sequence that encode a polypeptides derived from the potassium channel family of genes.

A vector according to the present invention can be introduced into any suitable host cell, whether eukaryotic or prokaryotic. Suitable prokaryotic host cells include, but are not limited to, *Escherichia coli, Bacillus subtilis, Pseudomonas aeruginosa,* and members of the genus Salmonella (e.g., *S. typhimurium, S. typhi, S. enteritidis,* and the like). Preferably a prokaryotic host cell is avirulent. Suitable eukaryotic host cells include, but are not limited to, rodent or mouse cells, *Saccharomyces cerevisiae,* and, particularly, human cells. Preferably the vector comprises an expression vector appropriate for expression of a polypeptide coding sequence in a human or rat cell, yeast cell, or, alternatively, an *E. coli* cell. The isolation of such cells, and/or the maintenance of such cells or cell lines derived therefrom in culture, has become a routine matter, and one in which the ordinary skilled artisan is well versed.

The form of the introduced vector can vary with the rationale underlying the introduction of the vector into the host cell. For example, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus or phage, or stably introduced into the host genome through double or single crossover recombination events.

Any appropriate means of introducing the vector into a host cell can be employed. In the case of prokaryotic cells, vector introduction can be accomplished, for instance, by electroporation, transformation, transduction, conjugation, or triparental mating. For eukaryotic cells, vectors can be introduced through the use of, for example, electroporation, transfection, infection, membrane fusion with liposomes, high velocity bombardment with DNA-coated microprojectiles, incubation with calcium phosphate-DNA precipitate, direct microinjection into single cells, and the like. Other methods are available and are known to those skilled in the art.

Thus, the present invention provides a host cell wherein the cell has been modified by introduction of a vector comprising a nucleic acid comprising a sequence that encodes polypeptides, as described herein.

The present invention also provides a pharmaceutical composition comprising a polypeptide or nucleic acid of the present invention and a pharmaceutically acceptable carrier. Such a composition is particularly well suited to regulate the flow of potassium ions in a cell expressing Shaker-like potassium ion channels. As such, the present inventive composition is desirably introduced into an animal, such as a mammal, in any suitable manner so that the present inventive polypeptide is delivered into the cytoplasm of a cell containing a Shaker-like potassium ion channel or so that the present inventive nucleic acid is delivered into a cell containing a Shaker-like potassium ion channel, to thereby provide for the artificial regulation, or modulation, of the Shaker-like potassium channels in the cell. In order to accomplish this regulation, the composition should be administered in an amount effective to modulate the flow of potassium ions through the Shaker-like potassium channels in a cell so the acceleration of N-type inactivation of the cell mediated by a β-subunit is prevented. This amount is expected to range from 0.01 to about 100 mg/kg body weight of the animal. Of course, if appropriate, one skilled in the art can adjust these concentrations upward or downward to suit the particular requirements of the use.

Pharmaceutically acceptable carriers for use with the present inventive polypeptides include, for example, vehicles, adjuvants, excipients, and diluents, as are well-known to those who are skilled in the art and are readily available to the public. It is preferred that the pharmaceutically acceptable carrier be one which is chemically inert to the active compounds and one which has no detrimental side-effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The polypeptides and nucleic acids of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The polypeptide or nucleic acid can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents, and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The polypeptides and nucleic acids of the present invention can be made into injectable formulations. The requirements for effective pharmaceutical carriers for injectable compositions are well known to those of ordinary skill in the art. See *Pharmaceutics and Pharmacy Practice,* J. B. Lippincott Co., Philadelphia, Pa., Banker and Chalmers, eds., pages 238–250 (1982), and *ASHP Handbook on Injectable Drugs,* Toissel, 4th ed., pages 622–630 (1986).

Additionally, the polypeptides and nucleic acids of the present invention can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present inventive pharmaceutical compositions can be provided in unit dosage form. For example, unit dosage forms for aerosol, oral, vaginal, or rectal administration, such as syrups, elixirs, and suspensions, can be provided wherein each dosage unit, e.g., teaspoonful, tablespoonful, tablet, or suppository contains a predetermined amount of the pharmaceutical composition. Similarly, unit dosage forms for injection or intravenous administration can comprise a composition as a solution in sterile water, normal saline, or other pharmaceutically acceptable carrier.

The term "unit dosage form" as used herein refers to physically discrete units suitable as unitary dosages for human and animal subjects, each unit containing a predetermined quantity of the pharmaceutical composition calculated in an amount sufficient to produce the desired effect. The specifications for the unit dosage forms of the present invention depend on the particular effect to be achieved, and the particular pharmacodynamics associated with the polypeptide or nucleic acid in the individual host.

The pharmaceutical compositions of the present invention can further include other active agents. Suitable other active agents include other ion channel regulators, particularly other potassium ion channel regulators.

In addition, the present invention provides a method of modulating the flow of potassium ion flow in a mammal, which method comprises acutely or chronically administering to a mammal in need of modulation of potassium ion flow a therapeutically effective amount, including a prophylactically effective amount, of a polypeptide or nucleic acid of the present invention. The polypeptides and nucleic acids of the present invention can be administered as part of a pharmaceutical composition. In addition, the present inventive nucleic acids can be included in a vector and/or a host cell prior to such administration.

The method of the present invention has particular usefulness in the treatment of any disease state or condition involving potassium ion flow. Thus, the following disease states and conditions can be treated in accordance with the present invention: hypoglycemia, anoxia/hypoxia, renal disease, osteoporosis, hyperkalemia, hypokalemia, hypertension, Addison's disease, abnormal apoptosis, induced apoptosis, clotting, modulation of acetylcholine function, and modulation of monoaminesepilepsy, allergic encephalomyelitis, multiple sclerosis (any demylelinating disease), acute traverse myelitis, neurofibromatosis, cardioplegia, cardiomyopathy, ischemia, ischemia reperfusion, cerebral ischemia, sickle cell anemia, cardiac arrythmias, peripheral monocuropathy, polynucuropathy, Gullain-Barre' Syndrome, peroneal muscular dystrophy, neuropathiese, Parkinson's disease, palsies, cerebral palsy, progressive supranuclear palsy, pseudobubar palsy, Huntington's disease, dystonia, dyskinesias, chorea, althetosis, choreothetosis, tics, memory degeneration, taste perception, smooth muscle function, skeletal muscle function, sleep disorders, modulation of neurotransmitters, acute disseminated encephalomyelitis, optic neuromyelitis, muscular dystrophy, myasthenia gravis, multiple sclerosis, cerebral vasospasm, hypertension, angina pectoris, asthma, congestive heart failure, ischemia related disorders, cardiac dysrhythmias, diabetes, carcinomas, neurocarcinomas, autoimmune-hypertrophy, neuromyotonia (Isaac's Syndrome) muscular disorders associated with drug abuse, and treatment for poisoning. For example, the polypeptides and nucleic acids of the present invention can be acutely administered, e.g., within about a few minutes to about an hour of the onset or realization of symptoms. The polypeptides and nucleic acids of the present invention also can be used in the treatment of chronic disease states and conditions, in particular those conditions and disease states wherein chronic prophylactic or therapeutic administration of the polypeptides and nucleic acids of the present invention will treat the disease, prevent the onset of symptoms, or will reduce recovery time.

The present inventive method includes the administration to an animal, such as a mammal, particularly a human, in need of the desired potassium ion channel modulation of an effective amount, e.g., a therapeutically effective amount, of one or more of the aforementioned present inventive polypeptides or nucleic acids, alone or in combination with one or more other pharmaceutically active compounds.

One skilled in the art will appreciate that suitable methods of administering a polypeptide or nucleic acid of the present invention to an animal are available, and, although more than one route can be used to administer a particular polypeptide or nucleic acid, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or other therapeutic response in the animal over a reasonable time frame. One skilled in the art will recognize that dosage will depend upon a variety of factors including the strength of the particular polypeptide or nucleic acid employed, the age, species, condition, and body weight of the animal, as well as the severity/stage of the disease or condition. The size of the dose will also be determined by the route, timing, and frequency of administration as well as the existence, nature, and extent of any adverse side-effects that might accompany the administration of a particular polypeptide or nucleic acid and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the polypeptide or nucleic acid. Thereafter, the dosage is increased by small increments until the optimum effect under the circumstances is reached. For convenience, the total daily dosage may be divided and administered in portions during the day if desired. In proper doses and with suitable administration of a certain polypeptide or nucleic acid, the present invention provides for a wide range of selective potassium ion channel responses. Exemplary dosages range from about 0.01 to about 100 mg/kg body weight of the animal being treated/day. Preferred dosages range from about 0.1 to about 10 mg/kg body weight/day. Desirably, the present inventive polypeptides and nucleic acids are administered to a mammal in a quantity sufficient to achieve an effective amount in the mammal, e.g., an amount sufficient to achieve an effective blood and/or tissue level of the polypeptide or nucleic acid of the present invention sufficient to modulate the flow of potassium currents in the indicated cells.

The present invention further provides a method for modulating the flow of potassium ions through a cell membrane surrounding a cytoplasm which comprises introducing the polypeptides of the present invention into the cytoplasm of the cell or the nucleic acids of the present invention into the cell (which can be, but need not be, different from the therapeutic use of the present inventive polypeptides and nucleic acids as described above). This can be achieved using any suitable method for the introduction of polypeptides or nucleic acids into cells. Cells can be transformed for example by, but not limited to, chemical treatment with calcium chloride for bacterial systems, lithium acetate for yeast systems, or calcium phosphate for higher eukaryotic systems. Additionally, liposome-mediated or other lipophilic reagents as well as dimethylsulfoxide or DEAE-dextran mediated transfection techniques can be used to introduce the polypeptides or nucleic acids of the present invention into cells in order to effect the regulation of potassium ions in cells with Shaker-like potassium ion channels.

The present invention also provides methods of regulating potassium ion flow in a cell, particularly a mammalian cell, using exogenous sources of Kvβ2. In particular, the present invention provides a method of modulating the flow of potassium ions through a cell membrane surrounding a cytoplasm comprising introducing exogenous Kvβ2 protein into the cytoplasm of the cell. Similarly, the present invention provides a method of modulating the flow of potassium ions through a cell membrane surrounding a cytoplasm comprising introducing an exogenous nucleic acid which encodes a polypeptide comprising Kvβ2 into the cell.

While Kvβ2 is present in many cells and contributes to the modulation of the flow of potassium ions, the present invention provides for the administration of Kvβ2 polypeptides or nucleic acids to a cell in order to increase the level of Kvβ2 in the cell, desirably so that the level of Kvβ2 present in the cell reaches a level which is higher than the initial level of Kvβ2 present in the cell. Of course, the protein Kvβ2 can be administered in any suitable fashion as described herein for the present inventive polypeptides. Likewise, the nucleic acids which are capable of expressing Kvβ2 in this embodiment can be delivered in any suitable fashion and can be in any suitable form (e.g., in a vector and/or a host cell) as described for the present inventive nucleic acids.

This invention further provides a method of detecting a molecule that binds to the NAB and the NAB-S1 linking region of an α-subunit of a Shaker-like potassium ion channel. In particular, the present invention provides a method of detecting a molecule that binds to the NAB and the NAB-S1 linking region of an α-subunit of a Shaker-like potassium ion channel comprising (a) contacting a putative NAB and linking region-binding molecule with the NAB and linking region of an α-subunit under conditions sufficient to allow for binding of the putative NAB and linking region-binding molecule and the NAB and linking region of the α-subunit, and (b) determining whether said binding has occurred. The present invention also provides a method of detecting a molecule that binds to the core region of a β-subunit of a Shaker-like potassium ion channel comprising (a) contacting a putative core region of a β-subunit-binding molecule with the core region of a β-subunit under conditions sufficient to allow for binding of the putative core region of the β-subunit-binding molecule with the core region of the β-subunit, and (b) determining whether said binding has occurred. With respect to this latter method, the core region of the β-subunit is preferably of SEQ ID NO:1, SEQ ID NO:2, or SEQ ID NO:3.

This invention further provides a method of detecting a molecule that binds to the NAB and the NAB-S1 linking region of an α-subunit of a Shaker-like potassium ion channel utilizing an improved yeast two-hybrid system. The yeast two-hybrid system is generally known in the art (see, e.g. Fields et al., *Nature,* 340, 245–246 (1989); Chevray et al., *Proc. Natl. Acad. Sci. USA,* 89, 5789–5793 (1992)), and the present invention provides an improved yeast two-hybrid system by utilizing two vectors have not heretofore been utilized in such a system. In particular, the present invention provides an improved yeast two-hybrid system, wherein the improvement comprises (a) a first vector containing nucleic acid sequences encoding a fusion protein of a DNA binding domain and a polypeptide selected from the group consisting of the core region of a β-subunit of a Shaker-like potassium ion channel, the NAB and linking region of an α-subunit of a Shaker-like potassium ion channel, a putative core region of a β-subunit-binding polypeptide, and a putative NAB and linking region-binding polypeptide, and (b) a second vector containing nucleic acid sequences encoding a fusion protein of a transactivation domain and a polypeptide selected from the group consisting of the core region of a β-subunit of a Shaker-like potassium ion channel, the NAB and the NAB-S1 linking region of an α-subunit of a Shaker-like potassium ion channel, a putative core region of a β-subunit-binding polypeptide, and a putative NAB and linking region-binding polypeptide, wherein said first and second vectors do not both contain a putative binding polypeptide or the NAB and the NAB-S1 linking region of an α-subunit a Shaker-like potassium ion channel.

Preferably, in the context of the yeast two-hybrid system, one of these vectors expresses either the NAB and NAB-S1 linking region or the core region of a β-subunit expressed as a fusion protein of any suitable DNA binding polypeptide in any suitable vector such as pPC86 and pPC97. Examples of DNA binding polypeptides encompass those which bind enhancer sequences, among which the Gal4 DNA binding domain a well known example. The other of these vectors expresses a transactivation domain expressed as a fusion protein with a polypeptide that potentially binds the polypeptide introduced into the first vector. Suitable potential binding proteins include β-subunits of potassium channels or any other protein suspected of binding to the peptide introduced into the first vector. As is well known in the art, the expression of the DNA binding fusion protein and the transactivation fusion protein can be interchanged, such that the known (or first) polypeptide is expressed as a fusion with the transcription activating polypeptide rather than the DNA binding polypeptide and the second is expressed as a fusion protein with a DNA binding domain.

This invention further provides a method for screening potential drug compounds in an improved yeast two-hybrid system. The improvement comprises the use in the yeast two-hybrid system of two vectors expressing polypeptides of the Shaker-like potassium ion channels known to bind to each other. In one preferred embodiment, this system comprises a first vector expressing a fusion protein containing the NAB and linking region of an α-subunit of the family Kv1 and a second vector expressing a fusion protein of the core region of a β-subunit, with one of the polypeptides being expressed as a fusion protein with a DNA binding domain and the other said polypeptide being expressed as a fusion protein with a transcription activation. In a second preferred embodiment, both fusion proteins contain core regions of the β-subunits or functional equivalents thereof. In both preferred embodiments, a putative drug agent is introduced into the system, and a change in the reporter or marker protein product, for example, β-galactosidase activity, is assayed. Any putative drug agent which alters the level of expression of the reporter or marker as monitored by a suitable assay, for example, color change, is a suitable candidate as one which may be used to modulate the potassium flow through Shaker-like channels. The potential drug agent can be of any form suitable for entry into the nucleus of a yeast cell. The potential drug agent can be allowed to freely diffuse into the yeast nucleus if it is of suitable composition, or the transfer of the drug agent can be facilitated by agents which enhance yeast cell permeability. Suitable yeast cell permeability agents encompass, but are not limited to, catalytic enzymes which degrade yeast cell walls, organic solvents such as dimethylsulfoxide which is known to enhance membrane permeability, application of electrical current to a solution of suitably prepared yeast cells, liposomes, and physical means such as drug agent coated teflon pellets. Preferably an optimal combination of permeability enhancing agents is used to suit a particular class of potential drug agents.

In another embodiment of the present invention, it was surprisingly discovered that the two polypeptides of the present invention would function within a yeast two-hybrid system. Prior to the present invention, it was not known that the polypeptides of the present invention had the functions now attributed to them, nor was it known that they would be suitable for use within a yeast two-hybrid system, as many proteins are simply not capable of being used in such a system. Thus, the present invention provides in another aspect an improved yeast two-hybrid system, wherein the improvement comprises: (a) a first vector containing nucleic acid sequences encoding a fusion protein of a DNA binding domain and a polypeptide selected from the group consisting of the core region of a β-subunit of a Shaker-like potassium ion channel, the NAB and NAB-S1 linking region of an α-subunit of a Shaker-like potassium ion channel, a putative core region of a β-subunit-binding polypeptide, and a putative NAB and linking region-binding polypeptide, and (b) a second vector containing nucleic acid sequences encoding a fusion protein of a transactivation domain and a polypeptide selected from the group consisting of the core region of a β-subunit of a Shaker-like potassium ion channel, the NAB and the NAB-S1 linking region of an α-subunit of a Shaker-like potassium ion channel, a putative core region of a β-subunit-binding polypeptide, and a putative NAB and linking region-binding polypeptide, wherein said first and second vectors do not both contain a putative binding polypeptide or the NAB and linking region of an α-subunit a potassium ion channel.

The following examples further illustrate the present invention but, of course, should not be construed as in any way limiting its scope.

EXAMPLE 1

This experiment was undertaken to determine whether COS cells are a suitable system for transient expression and characterization of $K^+$ ion channels.

In this experiment, in order to identify a suitable host for $K^+$ channel expression, various cell lines were compared using patch clamp recording and immunoblot analysis. The transient expression of different $K^+$ channel subunits was achieved using a mammalian expression vector containing the SV40 replication origin. Transcription was driven by the human cytomegalovirus (CMV) immediate early promoter. A plasmid expressing the CD4 surface antigen was included as 10 percent of the total input DNA, which allowed identification of the transfected cells using beads coated with the anti-CD4 antibody (Jurman et al., *Biotechniques,* 17, 876–881 (1994)).

As an initial step, traces of a typical MOCK-transfected COS cell in a 50 millisecond pulse were recorded while the holding potential was stepped from −77 mV to a series of commanding potentials. Under these conditions, the MOCK transfected COS cells showed low endogenous currents, and were therefore deemed suitable for further study. See FIG. 1A (top panel).

Figure 1A:
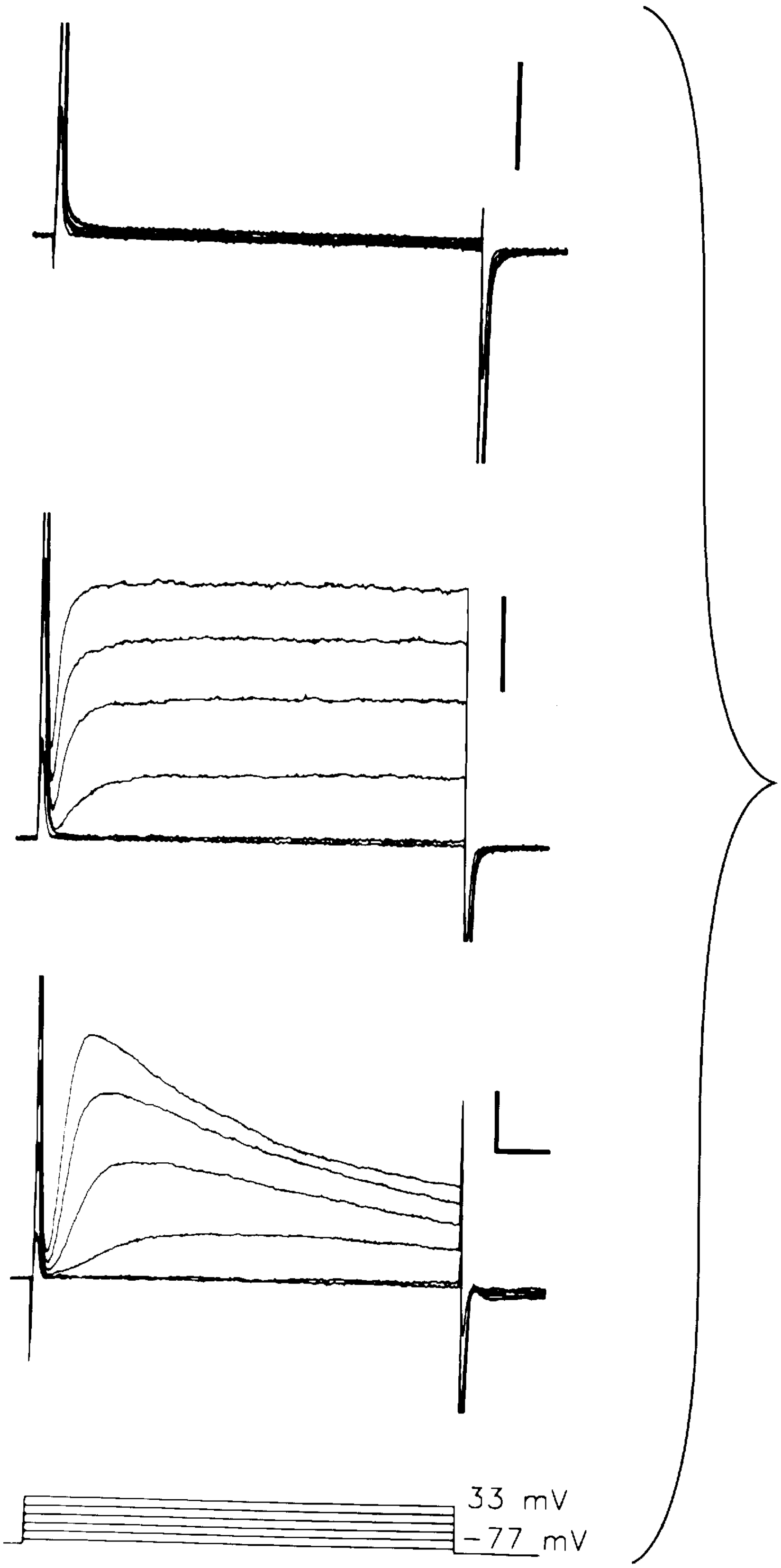
FIG. 1A is a collection of three graphs that depict the current response to different holding potentials recorded in COS cells. The top panel of FIG. 1A depicts the current response of MOCK transfected COS cells. The middle panel depicts the current responses of a cell transfected with ShBΔ(6–46), and the lower panel depicts the current response of a cell transfected with Shal2. Below the three panels is a scale indicating voltage steps from −77 mV to +33 mV at 20 mV increments. Horizontal scale bars indicate 5 msec, and vertical scale bars indicate 500 pA.
Figure 1B:
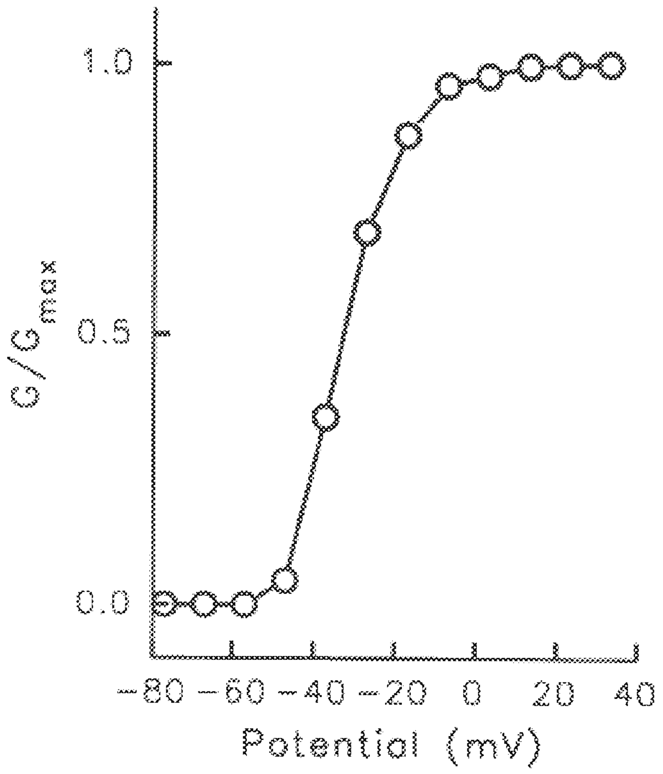
FIG. 1B is a graph of voltage-dependent activation of ShBΔ(6–46) expressed in COS cells. Conductance was calculated and normalized according to the maximum conductance ($G/C_{max}$) and plotted on the vertical axis. The horizontal axis depicts potentials in mV.

The Shaker B (ShB) and other $K^+$ channel α-subunits driven by the CMV promoter have currents up to 10 nA, depending upon the channel and the amount of transfected DNA (FIG. 1A). FIG. 1B shows the relative peak conductance as a function of voltage for ShBΔ(6–46), a mutated ShB potassium channel that lacks the inactivation gate (Hoshi et al., *Science,* 250, 533–538 (1990)). The voltage dependence of the peak current is qualitatively similar to that seen for Shaker-like currents recorded in Drosophila muscle and Xenopus oocytes (Iverson et al., *Proc. Natl. Acad. Sci. USA,* 85, 5723–5727 (1988); Timpe et al., *Neuron,* 8, 659–667 (1988); Zagotta et al., *Proc. Natl. Acad. Sci. USA,* 86, 7243–7247 (1989)).

To compare the possible endogenous Kv1 homologous polypeptides in different cells, total protein lysates from transfected cells were prepared and analyzed by immunoblot using an affinity-purified rabbit antibody, anti-NShB (Li et al., *Science,* 257, 1225–1230 (1992)). Because the affinity purification of the antibody was done using a fusion protein containing primarily the NAB region of ShB (NABShB), which is highly conserved within the Kv1 subfamily, the resultant immunoglobulin crossreacts with other Kv1 α-subunits.

Figure 1C:
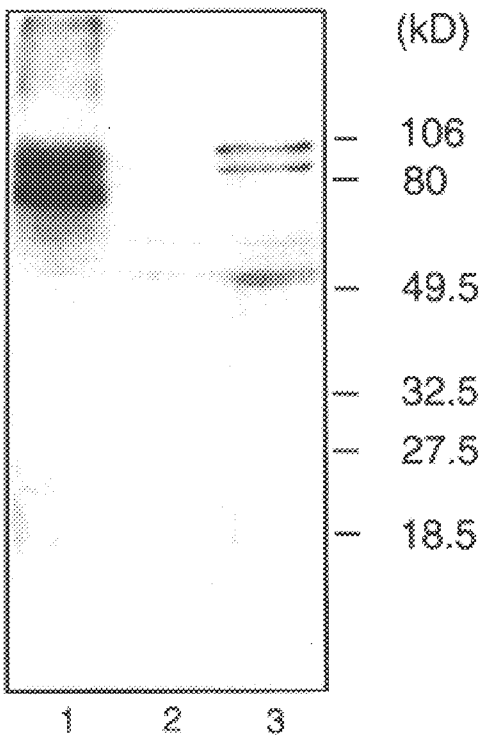
FIG. 1C depicts an immunoblot analysis of the ShB expression in transiently transfected COS cells. Equal amounts of protein, separated by SDS-PAGE and blotted to a nitrocellulose membrane, were detected by an affinity purified anti-NShB antibody. Lane 1 contains COS cell extracts transfected with ShB, lane 2 contains extracts of MOCK transfected cells, and lane 3 contains extracts of MOCK-transfected HEK293 cells. The numbers at the right side of the figure indicate molecular weights.

Under the foregoing conditions, little endogenous α-subunit proteins were detectable in the MOCK-transfected COS cells (FIG. 1C, lane 2). In contrast, high expression of the ShB polypeptide was detected in COS cells transfected with ShB cDNA (FIG. 1C, lane 1). As a control, two presumed endogenous α-subunits were detected in human embryonic kidney cells (HEK293) (FIG. 1C, lane 3), which also have higher endogenous voltage-sensitive $K^+$ currents.

The foregoing experiments demonstrated that the COS cell line is a reasonable system for the transient expression of $K^+$ ion channels.

EXAMPLE 2

This experiment was designed to exemplify the yeast two-hybrid system of the present invention.

To effectively test the interaction between Kvβ1 and various portions of α-subunits, a yeast two-hybrid system was used and is described in Table 1.

TABLE 1

Figure 2:
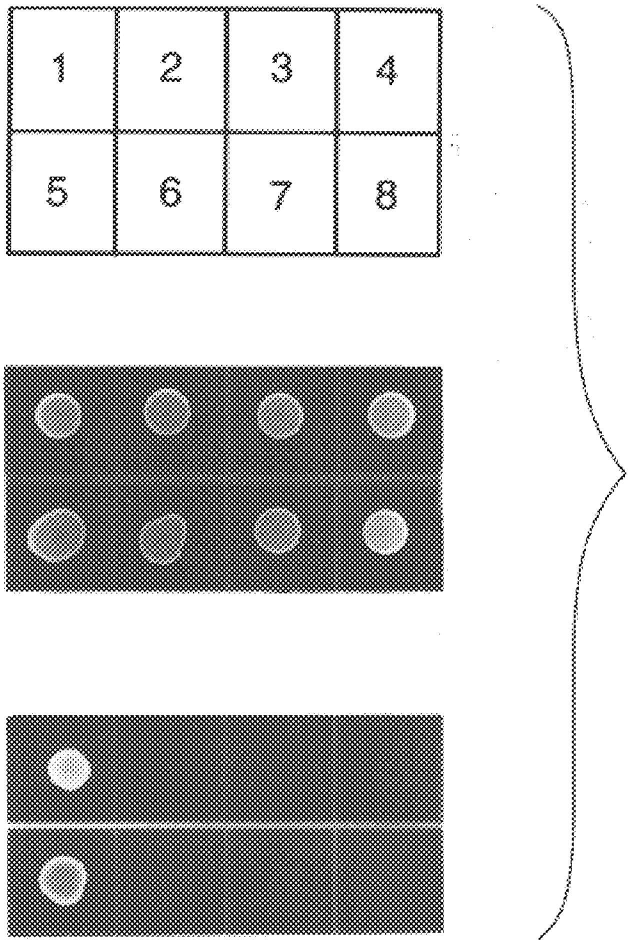
FIG. 2 depicts the results of a yeast two-hybrid assay wherein YGH1 yeast cells were transformed by different pairwise combinations of the two-hybrid constructs that express either fusion proteins of the DNA binding domain of GAL4 or the transcription activation domain of GAL4. The top panel shows the numbering scheme used to refer to the individual plate tests below. In the middle panel, the transformants carrying the two different fusion proteins were first selected by dextrose synthetic drop-out medium with no supplement of leucine and tryptophan (SD, −leu, −trp, +his) to ensure that in different combinations the transformants have both plasmids. In the lower panel, the identical number of cells in each combination were also dotted on the same medium without histidine (SD, −leu, −trp, −his). The transformants were allowed to grow at 30° C. for 65 hours.

Two-hybrid conditions for FIG. 2.

| | pPC97 (GAL4-DB) | pPC86 (GAL4-TA) |
|---|---|---|
| #1 | NRCK4 | Kvβ1 |
| #2 | CRCK4 | Kvβ1 |
| #3 | GAL4-DB | Kvβ1 |
| #4 | Kvβ1 | GAL4-TA |
| #5 | NShB (Kv1 subfamily) | Kvβ1 |
| #6 | NDRK1 (Kv2 subfamily) | Kvβ1 |
| #7 | NNGK2b (Kv3 subfamily) | Kvβ1 |
| #8 | Nrshal1 (Kv4 subfamily) | Kvβ1 |

Figure 3:
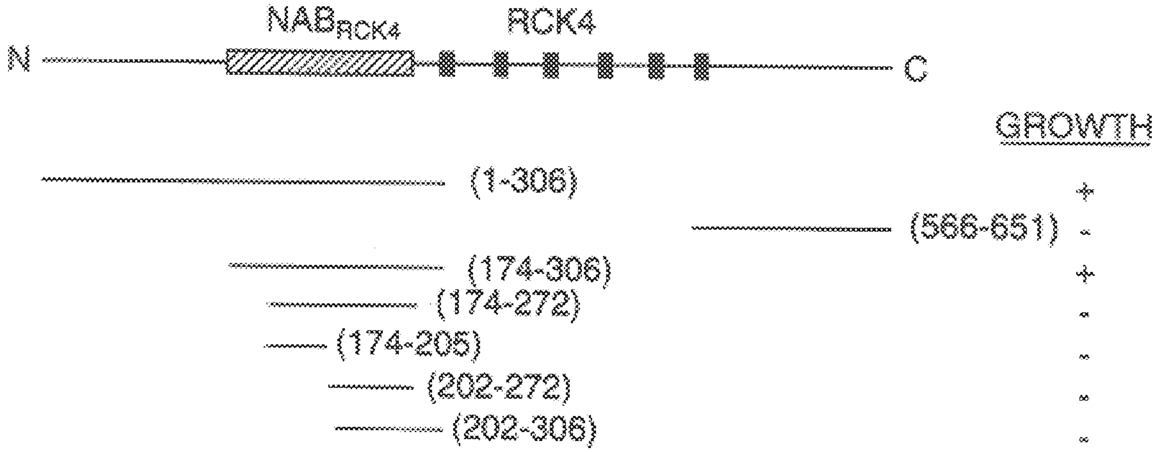
FIG. 3 depicts the results of deletion mapping of the region(s) in RCK4 for Kvβ1 binding. A diagram representing the coding sequence of RCK4 is shown. Black boxes indicate the putative membrane spanning segments, S1 to S6; the dashed box indicates the NABRCK4 region (a.a. 174–272). Different coding sequences as indicated in parentheses and represented by horizontal lines were cloned into the pPC86 vector for the yeast two-hybrid test with pPC97-Kvβ1 as described in FIG. 3 and the procedures of Example 3. At the right side of the figure, symbols are used to indicate the viability of the yeast under selective conditions, with a "+" indicating growth, and a "−" indicating no growth.

Cytoplasmic $NH_2$— and COOH— terminal domains of different α-subunits were subcloned and expressed as fusion proteins of the GAL4 DNA binding (DB) domain. Kvβ1 was expressed as a fusion protein of either the GAL4 DNA binding (DB) domain or transcription activation (TA) domain. The Kvβ1 fusion proteins did not activate transcription by themselves, because yeast transformants containing either GAL4-DB-Kvβ1/GAL4-TA or GAL4-TA-Kvβ1/GAL4-DB did not grow in synthetic medium lacking histidine (selection medium) (FIG. 2, Nos. 3 and 4). When Kvβ1 was coexpressed with the $NH_2$-terminal domain of RCK4 (NRCK4) (a.a. 1–306; an α-subunit sensitive to Kvβ1-mediated inactivation), the yeast transformants grew on a selective medium (FIG. 2, No. 1). As NRCK4 did not have endogenous transcription activation activity, it was determined that NRCK4 also has a binding site for Kvβ1. In contrast, coexpression of Kvβ1 and the COOH-terminal domain of RCK4 (CRCK4, a.a. 566–651) did not permit growth on the selective medium (FIG. 2, No. 2). It was determined from these results that Kvβ1 binds to the $NH_2$-terminal domain of RCK4 (FIG. 2 and FIG. 3).

While it was previously discovered that the $NH_2$-terminal domains of Kv1, Kv2, Kv3, and Kv4 associate with each other strictly within each subfamily, it was not known to what extent there was any analogous specificity as regarding the α-β subunit interaction. To determine this, Kvβ1 was coexpressed with the $NH_2$-terminal domains of α-subunits including ShB (Kv1), DRK1 (Kv2.1), NGK2b (Kv3.1), and rshal1 (Kv4.2) (Xu et al., *J. Biol. Chem.,* 270, 1–8 (1995)). Yeast transformants containing Kvβ1 and the $NH_2$-terminal domain of ShB, but not that of DRK1 (a.a. 1–182), NGK2b (a.a. 1–180) or rshal1 (a.a. 1–228), grew on the selective medium (FIG. 2, Nos. 5–8). In addition, coexpression of Kvβ1 with the $NH_2$-terminal domain of Drosophila Shab11 of the Kv2 subfamily, Shaw2 of the Kv3 subfamily, or Shal2 of the Kv4 subfamily did not result in growth of the transformants on the selective medium (data not shown). From this data, it was determined that the binding specificity of Kvβ1 to the $NH_2$-terminal domain of the α-subunits coincides precisely with the Kv1 subfamily.

This experiment demonstrated the relevant parameters of potassium channel α-β subunit interactions, and that the two hybrid system could be successfully used to determine physiologically relevant parameters of $K^+$ channel protein-protein interactions.

EXAMPLE 3

This experiment was designed to define a class of sequences useful in monitoring α- and β-subunit interactions in potassium ion channels.

In an effort to determine the actual region of NRCK4 that mediates interaction with Kvβ1, deletion mutants corresponding to different segments of NRCK4 were constructed. Their ability to interact was analyzed using the yeast two hybrid test.

The results indicated that the minimal region in NRCK4 capable of associating with Kvβ1 using the two hybrid test was a polypeptide fragment of amino acids 174–306, which overlaps with the NAB of RCK4 and includes the linking region between NAB and the transmembrane spanning region S1. In contrast, the same comparison between RCK4 and Shal2 shows only 24 percent amino acid identity.

This experiment demonstrates (FIG. 3) that the NABKv1 region of the α-subunits is a critical determinant of subfamily-specific α-Kvβ1 binding, and that the additional linking region is required to allow α-Kvβ1 binding. Surprisingly, it was found that it is NAB plus the linking region (i.e., the NAB-S1 linking region), as opposed to NAB alone, which provides a suitable affinity peptide for the core regions of Kvβ subunits.

EXAMPLE 4

This example was designed to determine whether the core regions of Kvβ of the present invention are responsible for the antagonism of Kvβ1 acceleration of inactivation.

Potassium channel inactivation accelerated by Kvβ1 was investigated by constructing deletion mutants of Kvβ1 and testing their association with NRCK4 using the two-hybrid system as described in prior examples. No detectable difference in association with RCK4 was found between the wild type Kvβ1 and Kvβ1D (1–72), which lacks the Kvβ1 inactivation gate. Thus, the Kvβ1 conserved core region (a.a. 73–401) was determined to be sufficient to bind NRCK4 (FIG. 4). On the basis of the foregoing data, it was concluded that the interaction between Kvβ1 and the $NH_2$-terminal domains of α-subunits seen in the two-hybrid test is different from the interaction between the Kvβ1 inactivation gate and its receptor.

Further deletions of Kvβ1 significantly reduced its ability to associate with NRCK4 (FIG. 4). This led to the conclusion that amino acids 73 to 401 are directly and indirectly involved in the α-Kvβ1 association. As it was known that the mapped region (a.a. 73–401), referred to herein as the core region, for the Kvβ1 binding is highly conserved among Kvβ1, Kvβ2, Kvβ3, and Kvβ-HK (FIG. 5), the results of this experiment suggest that the corresponding core regions of other β-subunits are involved in association with the $NH_2$-terminal domains of the α-subunits.

EXAMPLE 5

This example was designed to determine whether Kvβ1 and Kvβ2 share common binding epitopes on the Kvα1 family of α-subunits.

As Kvβ1 and Kvβ2 share considerable sequence homology, the potential interaction of Kvβ2 with the cytoplasmic regions of the Kv1.4, an α-subunit which has been found to interact with Kvβ2, was tested (Rhodes et al., *J. Neurosci.,* 15, 5360–5371 (1995)). To begin the test, the $NH_2$-terminal domain and COOH-terminal domain of Kv1.4 (RCK4) were subcloned. These truncated cytoplasmic fragments, i.e., the $NH_2$-terminal domain (a.a. 1–306) and COOH-terminal domain (a.a. 566–651), were expressed individually with Kvβ2 as GAL4 fusion proteins. Using this methodology, if Kvβ2 were to interact with one or both truncated Kv1.4 fragments, the resultant interaction(s) would confer the ability upon the yeast transformants to grow on synthetic medium lacking histidine. Table 2 below defines the conditions of the yeast two-hybrid system in FIG. 6A.

TABLE 2

Figure 6A:
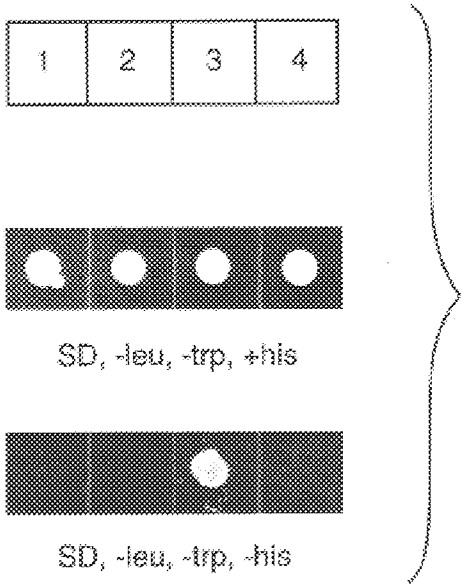
FIG. 6A depicts the results of a yeast two-hybrid assay wherein YGH1 yeast cells were transformed by different pairwise combinations of the two-hybrid constructs that express either fusion proteins of the DNA binding domain of GAL4 or the transcription activation domain of GAL4. The top panel shows the numbering scheme used to refer to the individual plate tests below. In the middle panel, the transformants carrying the two different fusion proteins were first selected by dextrose synthetic drop-out medium with no supplement of leucine and tryptophan (SD, −leu, −trp, +his) to ensure that in different combinations the transformants have both plasmids. In the lower panel, identical numbers of cells in each combination were also dotted on the same medium without histidine (SD, −leu, −trp, −his). The transformants were allowed to grow at 30° C. for 65 hours.

Two-hybrid conditions for FIG. 6A.

| | pPC97 (GAL4-DB) | pPC86 (GAL4-TA) |
|---|---|---|
| #1 | Kvβ2 | GAL4-TA |
| #2 | GAL4-DB | Nkv1.4 |
| #3 | Kvβ2 | Nkv1.4 |
| #4 | Kvβ2 | Ckv1.4 |

When Kvβ2 was expressed alone either as a fusion protein of GAL4 DNA binding domain (GAL4-DB) or that of GAL4 transcription activation domain (GAL4-TA), the transformants grew on double selection medium supplemented with histidine, thereby indicating that the transformants carry both plasmids (FIG. 6A, Nos. 1 & 2, top photograph). When the same number of transformants were allowed to grow on the triple selection medium lacking histidine, they showed no growth (FIG. 6A, Nos. 1 & 2, lower photograph). This indicated that Kvβ2 itself does not exert any activity which permits the yeast transformants to grow on the selection medium.

In contrast, the coexpression of Kvβ2 and the $NH_2$terminal domain (FIG. 6A, No. 3), not the COOH-terminal domain (FIG. 6A, No. 4), of Kv1.4 resulted in growth on the selection medium lacking histidine. Similar results were obtained using a β-galactosidase assay (data not shown). Thus, like Kvβ1, Kvβ2 was determined to interact with the $NH_2$-terminal domain of the Kv1.4 α-subunit.

The ability of Kvβ2 to interact with the $NH_2$-terminal domain of Kv1.4 suggests that the resulting association is essential for Kvβ2 to interact with α-subunits. In the case of Kvβ1, its subfamily-specific association with the $NH_2$-terminal domains of Kv1 α-subunits is essential for the Kvβ1-mediated inactivation. Coimmunoprecipitation of $K^+$ channel polypeptides in rat brain has indicated that Kvβ2 interacts with Kv1.2 and Kv1.4, but not Kv2.1 (Rhodes et al., *J. Neurosci.,* 15, 5360–5371 (1995)). What is not known, however, is whether the failure to detect the Kv2.1-Kvβ2 complex is due to the incompatibility of these two subunits to interact or their limited overlapping expression in vivo. To test the specificity of the Kvβ2-α (interaction, pairwise combinations of Kvβ2 and the $NH_2$-terminal domains of eight different α-subunits were analyzed in the yeast two hybrid system. The eight α-subunits included were: ShB (Kamb et al., *Cell,* 50, 405–413 (1987); Pongs et al., *EMBO J.,* 7, (1988); Tempel et al., *Science,* 237, 770–775, (1987), Shabll, Shaw2, and Shal2 from Drosophila (Butler et al., *Nucleic Acids Res.,* 18, 2173–2174 (1990); Kv1.4 (or RCK4) (Stuhmer et al., *EMBO J.,* 8, 3235–3244 (1989), Kv2.1 (or DPK1) (Frech et al., *Nature,* 340, 642–645 (1989), Kv3.1 (or NGK2b) (Yokoyama et al., *FEBS Lett.,* 259, 37–42 (1989), and Kv4.2(or rShal1) (Baldwin et al., *Neuron,* 7, 471–483 (1991); Roberds et al., *Proc. Natl. Acad. Sci. USA,* 88, 1798–1802 (1991)) from rat. These genes belong to the four major subfamilies (one fly gene and one rat gene for each subfamily). Table 3 defines the conditions of the two-hybrid system in FIG. 6B.

TABLE 3

Figure 6B:
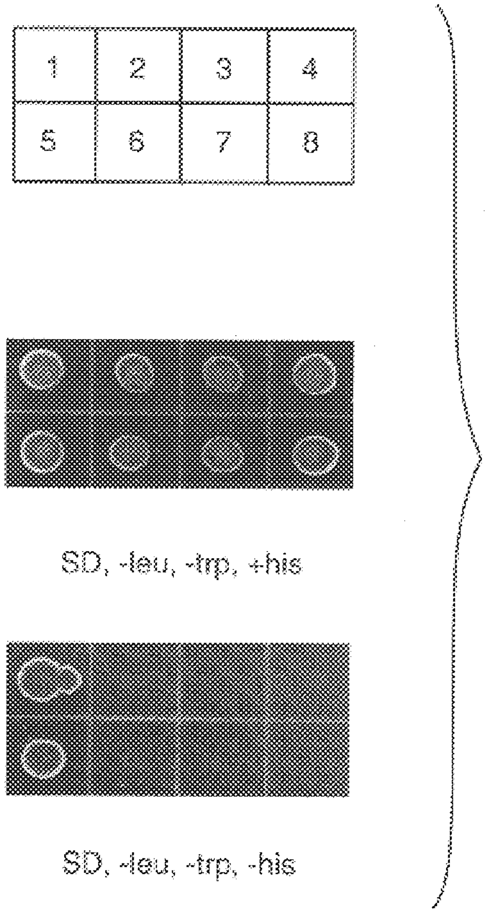
FIG. 6B depicts the results of a yeast two-hybrid assay wherein YGH1 yeast cells were transformed by different pairwise combinations of the two-hybrid constructs that express either fusion proteins of the DNA binding domain of GAL4 or the transcription activation domain of GAL4. The top panel shows the numbering scheme used to refer to the individual plate tests below. In the middle panel, the transformants carrying the two different fusion proteins were first selected by dextrose synthetic drop-out medium with no supplement of leucine and tryptophan (SD, −leu, −trp, +his) to ensure that in different combinations the transformants have both plasmids. In the lower panel, identical numbers of cells in each combination were also dotted on the same medium without histidine (SD, −leu, −trp, −his). The transformants were allowed to grow at 30° C. for 65 hours.

Two-hybrid conditions for FIG. 6B.

| | pPC97 (GAL4-DB) | pPC86 (GAL4-TA) |
|---|---|---|
| #1 | Kvβ2 | NShB (Drosophila, Kv1 subfamily) |
| #2 | Kvβ2 | NshabII (Drosophila, Kv2 subfamily) |
| #3 | Kvβ2 | Nshaw2 (Drosophila, Kv3 subfamily) |
| #4 | Kvβ2 | Nsha12 (Drosophila, Kv4 subfamily) |
| #5 | Kvβ2 | Nkv1.4 (rat, Kv1 subfamily) |
| #6 | Kvβ2 | Nkv2.1 (rat, Kv2 subfamily) |
| #7 | Kvβ2 | Nkv3.1 (rat, Kv3 subfamily) |
| #8 | Kvβ2 | Nkv4.2 (rat, Kv4 subfamily) |

Among the selected $NH_2$-terminal domains, Kvβ2 was found to interact only with the $NH_2$-terminal domains of ShB and Kv1.4 (FIG. 6B, Nos. 1 & 5), both of which belong to the Kv1 subfamily. Furthermore, the Kvβ2 interacting site was mapped to a.a. 174–306 within the NH2-terminal domain of Kv1.4. The mapped region coincides precisely with the domain which interacts with Kvβ1.

As a result of the foregoing experiments, it was determined that both Kvβ1 and Kvβ2 interact subfamily-specifically with the Kv1 α-subunits, and that they also share the same binding site on the α-subunits.

EXAMPLE 6

This experiment was designed to determine whether Kvβ2 can form an oligomeric complex with itself or with Kvβ1 in the absence of α-subunits. This ability is significant because, if Kvβ core regions are to be used as inhibitors of Kvβ1 or other Kvβ proteins, it is important to know that Kvβ proteins can oligomerize.

In this experiment, the coding sequences of Kvβ2 (a.a. 1–367) and Kvβ1 (a.a. 1–401) were subcloned into the yeast two hybrid vectors. Table 4 defines the conditions of the two-hybrid system in FIG. 7.

TABLE 4

Figure 7:
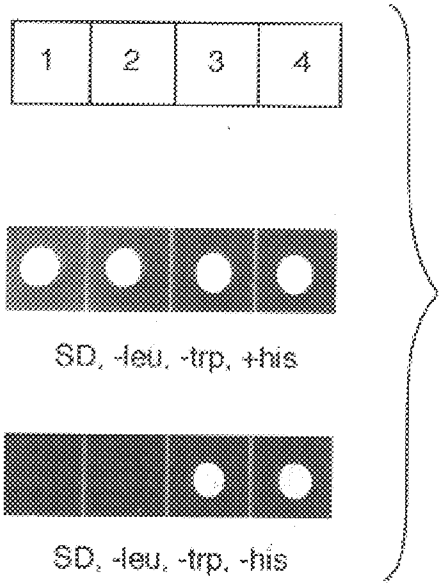
FIG. 7 depicts the results of a yeast two-hybrid assay wherein YGH1 yeast cells were transformed by different pairwise combinations of the two-hybrid constructs that express either fusion proteins of the DNA binding domain of GAL4 or the transcription activation domain of GAL4. The top panel shows the numbering scheme used to refer to the individual plate tests below. In the middle panel, the transformants carrying the two different fusion proteins were first selected by dextrose synthetic drop-out medium with no supplement of leucine and tryptophan (SD, −leu, −trp, +his) to ensure that in different combinations the transformants have both plasmids. In the lower panel, identical numbers of cells in each combination were also dotted on the same medium without histidine (SD, −leu, −trp, −his). The transformants were allowed to grow at 30° C. for 65 hours.

Two-hybrid conditions for FIG. 7.

| | pPC97 (GAL4-DB) | pPC86 (GAL4-TA) |
|---|---|---|
| #1 | Kvβ1 | GAL4-TA |
| #2 | GAL4-DB | Kvβ2 |
| #3 | Kvβ2 | Kvβ2 |
| #4 | Kvβ1 | Kvβ2 |

FIG. 7 shows that Kvβ2 can indeed interact with itself to form multimers as the yeast transformants grow in the selection medium lacking histidine (FIG. 7, Nos. 3 & 4). The foregoing data demonstrates that Kvβ2 is capable of interacting with itself in the absence of α-subunits.

As it was found that Kvβ2 forms multimers in the absence of α-subunits (FIG. 7, nos. 3 & 4) and has considerable overall sequence homology (73%) to Kvβ1, a further experiment was conducted in order to determine whether there was any interaction between Kvβ1 and Kvβ2. When Kvβ1 and Kvβ2 were subjected to the yeast two-hybrid analysis similar to the above experiment, it was observed that Kvβ1 and Kvβ2 also interact.

This experiment demonstrates that Kvβ1 and Kvβ2 can form heteromultimers in the absence of the pore-forming α-subunits.

EXAMPLE 7

Both Kvβ2 and Kvβ1 interact with the Kv1 α-subunits by recognizing the same region in the Kv1 α-subunits (FIG. 6). Additionally, it was previously demonstrated that Kvβ2 interacts with itself and/or Kvβ1 to form homo- and/or hetero-multimers (FIG. 7). Because Kvβ1, not Kvβ2, induces the fast inactivation of the Kv1 α-subunits which lack fast inactivation. This experiment was designed to determine whether Kvβ2 is effective in inactivating the acceleration of N-type inactivation of potassium channels activated by Kvβ1.

Figure 8A:
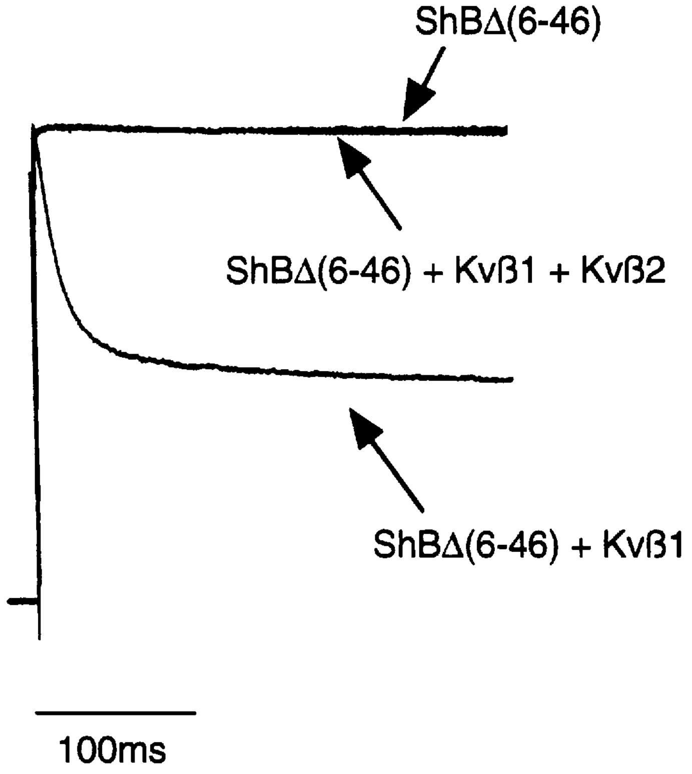
FIG. 8A is a representation of the inhibition of the Kvβ1-mediated inactivation by Kvβ2 using normalized $K^+$ currents obtained by whole cell voltage clamp recording. The current responses were recorded from COS cells transfected with ShBΔ(6–46), ShBΔ(6–46)+Kvβ1, or ShBΔ(6–46)+Kvβ1+Kvβ2. Plasmid inputs were 3 mg for ShBΔ(6–46), 18 mg for Kvβ1, and 15 mg for Kvβ2. Typical responses to a voltage step from −77 mV to +13 mV of one cell from each group were normalized according to the peak response and superimposed. The traces for ShBΔ(6–46)+Kvβ1 and ShBΔ(6–46)+Kvβ1+Kvβ2 have been fit by a two-exponential function to yield inactivation constants. ShBΔ(6–46)+Kvβ1: A2/(A1+A2)=0.19; t1=11.9 ms; t2=154 ms. ShBΔ(6–46)+Kvβ1+Kvβ2: A2/(A1+A2)=1; t1 (not available since A1=0); t2=178 ms.
Figure 8B:
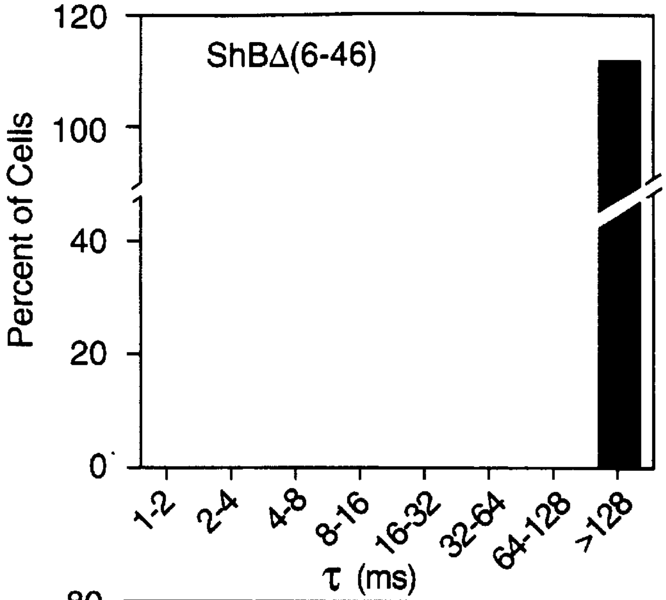
FIGS. 8B–8D depict graphs indicating the distribution of inactivation time constants. The decay phase of current responses (300 ms duration) to a voltage step from −77 mV to +13 mV was fit by a double exponential function to obtain the onset parameters of inactivation. The cell number (in percentage normalized to the total cell number recorded for that group) was plotted against the inactivation constants. For a given recorded trace, if the response shows both fast and slow inactivation, only t1 is used in this plot. If a trace shows no fast inactivation (i.e., A1=0), t2 is used in this plot.
Figure 8C:
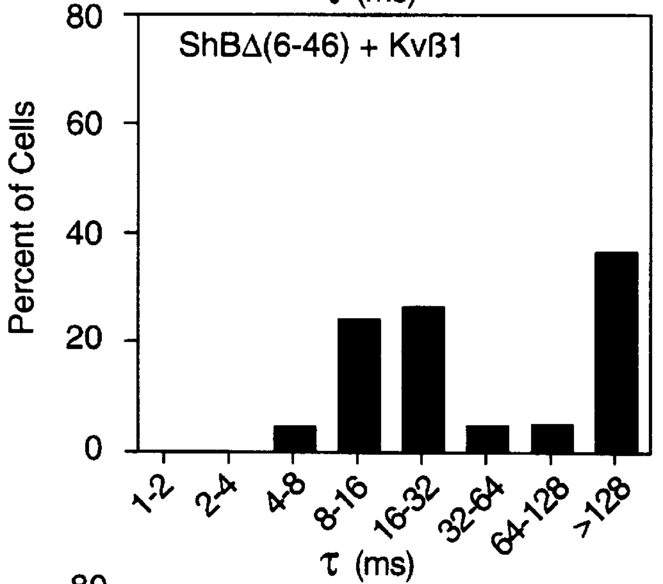
Figure 8D:
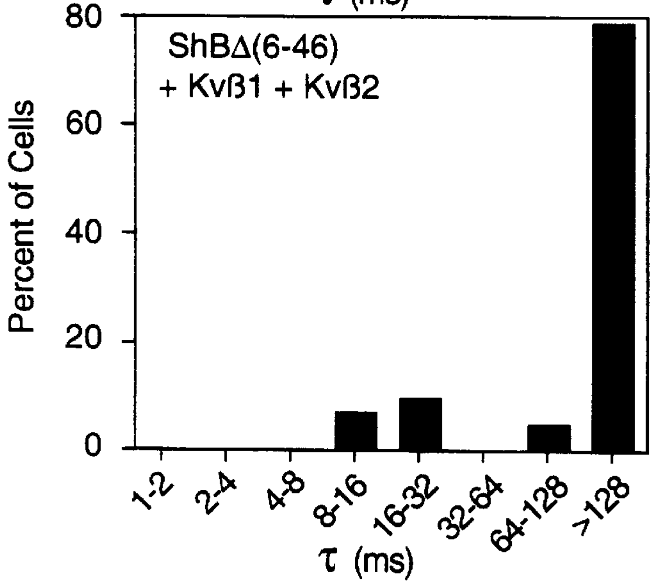

In this experiment, Kvβ1 and a compatible α-subunit were coexpressed in the presence or absence of Kvβ2, and an assay was conducted to determine whether Kvβ2 altered the ability of Kvβ1 to inactivate. More specifically, COS cells were cotransfected with non-inactivating ShBΔ(6–46) and Kvβ1 with a 1:6 plasmid ratio of α:Kvβ1. FIG. 8A (upper panel) shows three representative traces that were superimposed and normalized. These traces were recorded by stepping the holding potential from −77 mV to a test potential of +13 mV for a duration of 300 ms. ShBΔ(6–46) alone produced a trace with fast activating kinetics lacking N-type fast inactivation. When Kvβ1 was included in the transfection, however, Kvβ1-mediated fast inactivation was observed (FIG. 8A). If, however, both Kvβ1 and Kvβ2 were included in a plasmid ratio of α:Kvβ1:Kvβ2=1:6:5, most transfected cells showed traces similar to those obtained for ShBΔ(6–46) alone (see, e.g., FIG. 8A). When the inactivation properties of the representative traces were fit with a double exponential function, it was concluded that the presence of Kvβ2 removes the fast inactivation component of ShBΔ(6–46) induced by Kvβ1.

EXAMPLE 8

This experiment was designed to determine whether the formation of heteromultimeric α-Kvβ2 and/or Kvβ1-Kvβ2 complexes has any effect on inhibiting the Kvβ1-mediated inactivation.

Figure 9E:
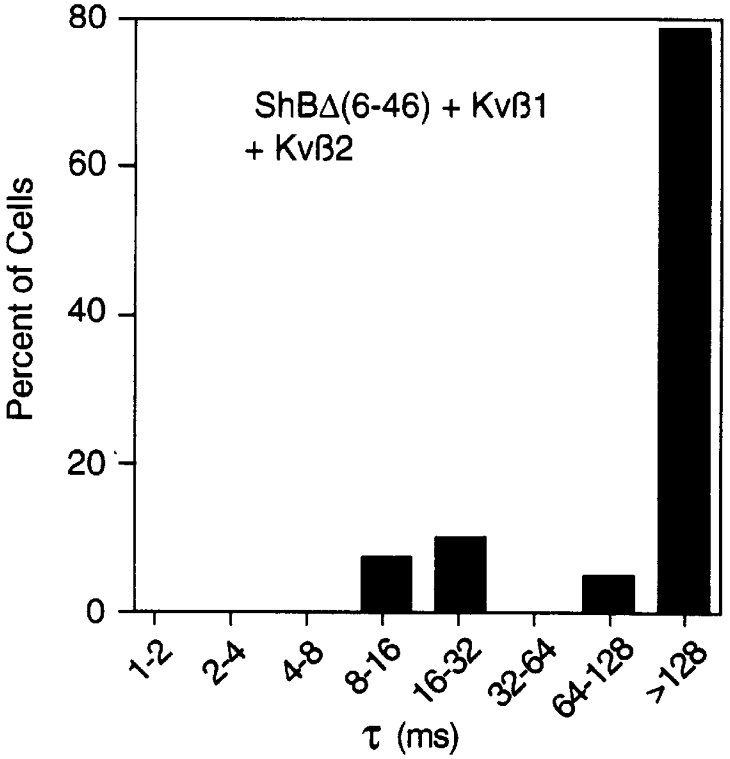
FIGS. 9E–9H depict the distribution of inactivation time constants. Typical responses to a voltage step from −77 mV to +13 mV of cells from each group were normalized according to the peak response. The inactivation time constant distribution on the horizontal axis is plotted against the cell number on the vertical axis.
Figure 9F:
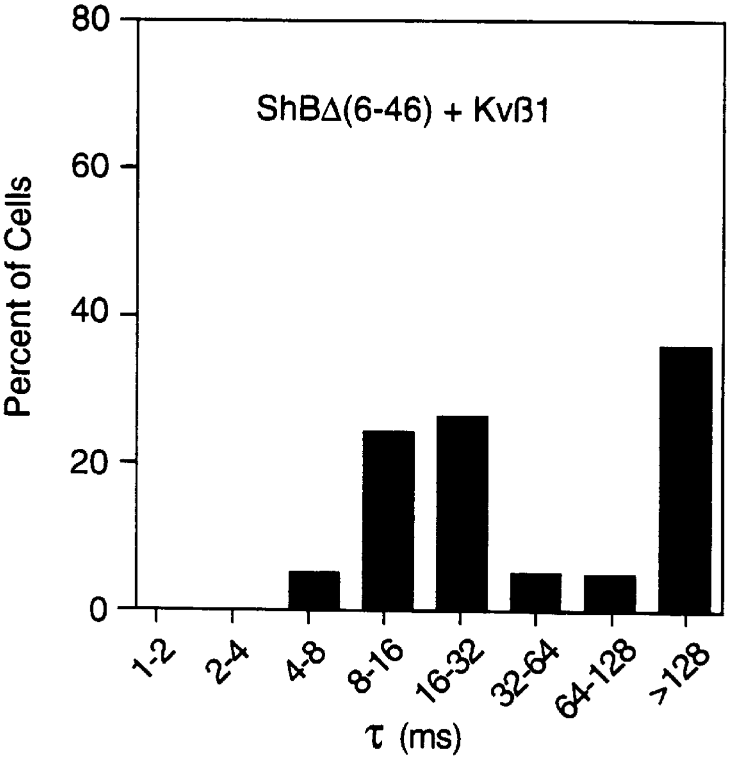
Figure 9G:
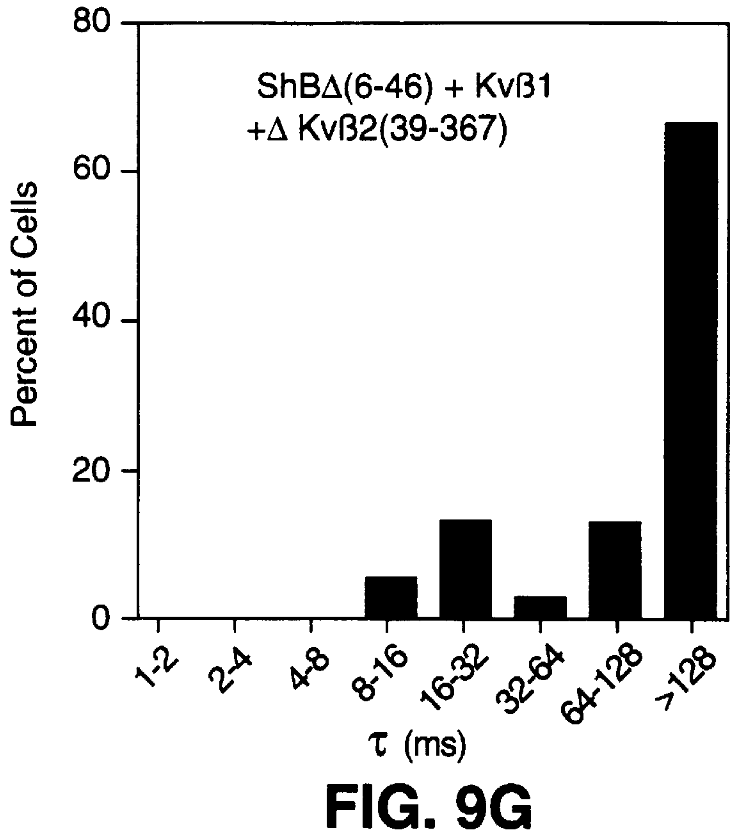
Figure 9H:
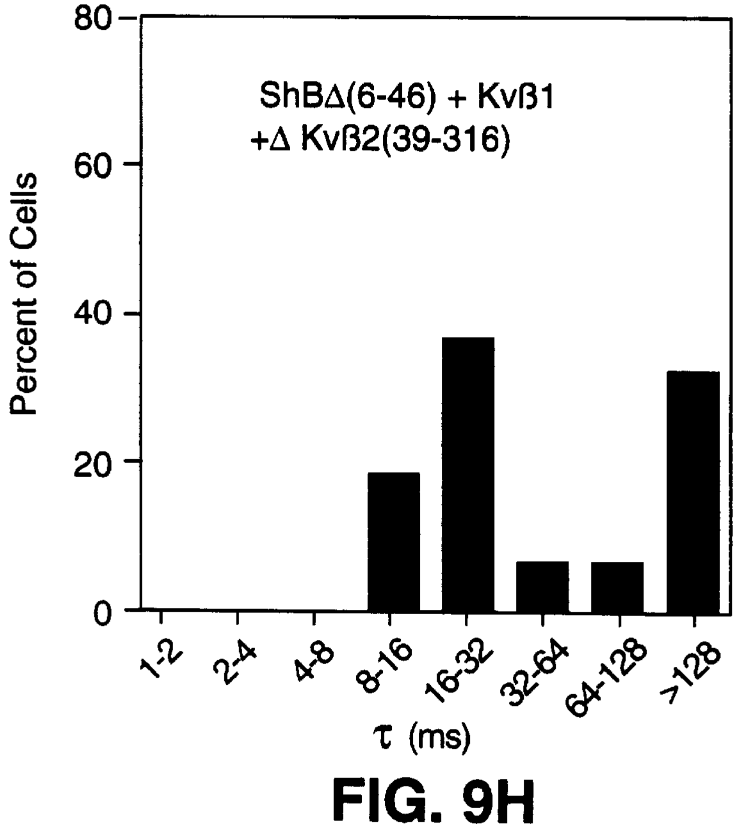

In this experiment, two Kvβ2 deletion mutants were constructed: ΔKvβ2(39–367) and ΔKvβ2(39–316) (FIG. 9A). The ΔKvβ2(39–367) mutant contained the intact interacting region mapped by the yeast two-hybrid analysis. In ΔKvβ2(39–316), 51 residues C-terminal to the interacting region of Kvβ2 were truncated. Under these conditions, the ability to interact should correlate with the activity in inhibiting the Kvβ1-mediated inactivation.

Cotransfection of ShBΔ(6–46) and Kvβ1 in the presence of either ΔKvβ2(39–367) or ΔKvβ2(39–316), and examination of the subsequent inactivation properties (FIG. 9C, 9D), revealed that the ability of Kvβ2 and ΔKvβ2(39–367), but not that of ΔKvβ2(39–316), were comparable. Among the 39 recorded Shaker-like positive cells transfected in the presence of ΔKvβ2(39–367), only 22.5% of cells were found to show fast inactivation (FIGS. 9B). ΔKvβ2(39–367) was found to act similarly to Kvβ2 by decreasing the number of cells that exhibited the fast inactivation (FIG. 9C).

In contrast, among the 49 recorded cells which were transfected in the presence of ΔKvβ2(39–316), 61% of cells showed fast inactivation. The distribution of inactivation constants from this group of cells was very similar to that obtained from cells transfected by ShBΔ(6–46)+Kvβ1.

This experiment demonstrated that the mutated Kvβ2 possesses the ability to interact with ShBΔ(6–46) and/or Kvβ1, and directly correlates with its ability to inhibit the Kvβ1-mediated inactivation. This further demonstrates that the coassembly of the Kvβ core plays an active role in inhibiting the Kvβ1-mediated inactivation.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 329 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Tyr Arg Asn Leu Gly Lys Ser Gly Leu Arg Val Ser Cys Leu Gly Leu
  1               5                  10                  15

Gly Thr Trp Val Thr Phe Gly Gly Gln Ile Ser Asp Glu Val Ala Glu
             20                  25                  30

Arg Leu Met Thr Ile Ala Tyr Glu Ser Gly Val Asn Leu Phe Asp Thr
         35                  40                  45

Ala Glu Val Tyr Ala Ala Gly Lys Ala Glu Val Ile Leu Gly Ser Ile
     50                  55                  60

Ile Lys Lys Lys Gly Trp Arg Arg Ser Ser Leu Val Ile Thr Thr Lys
 65                  70                  75                  80

Leu Tyr Trp Gly Gly Lys Ala Glu Thr Glu Arg Gly Leu Ser Arg Lys
                 85                  90                  95

His Ile Ile Glu Gly Leu Lys Gly Ser Leu Gln Arg Leu Gln Leu Glu
            100                 105                 110

Tyr Val Asp Val Val Phe Ala Asn Arg Pro Asp Ser Asn Thr Pro Met
        115                 120                 125

Glu Glu Ile Val Arg Ala Met Thr His Val Ile Asn Gln Gly Met Ala
    130                 135                 140

Met Tyr Trp Gly Thr Ser Arg Trp Ser Ala Met Glu Ile Met Glu Ala
145                 150                 155                 160

Tyr Ser Val Ala Arg Gln Phe Asn Met Ile Pro Pro Val Cys Glu Gln
                165                 170                 175

Ala Glu Tyr His Leu Phe Gln Arg Glu Lys Val Glu Val Gln Leu Pro
```

-continued 180 185 190

Glu Leu Tyr His Lys Ile Gly Val Gly Ala Met Thr Trp Ser Pro Leu
195 200 205

Ala Cys Gly Ile Ile Ser Gly Lys Tyr Gly Asn Gly Val Pro Glu Ser
210 215 220

Ser Arg Ala Ser Leu Lys Cys Tyr Gln Trp Leu Lys Glu Arg Ile Val
225 230 235 240

Ser Glu Glu Gly Arg Lys Gln Gln Asn Lys Leu Lys Asp Leu Ser Pro
245 250 255

Ile Ala Glu Arg Leu Gly Cys Thr Leu Pro Gln Leu Ala Val Ala Trp
260 265 270

Cys Leu Arg Asn Glu Gly Val Ser Ser Val Leu Leu Gly Ser Ser Thr
275 280 285

Pro Glu Gln Leu Ile Glu Asn Leu Gly Ala Ile Gln Val Leu Pro Lys
290 295 300

Met Thr Ser His Val Val Asn Glu Ile Asp Asn Ile Leu Arg Asn Lys
305 310 315 320

Pro Tyr Ser Lys Lys Asp Tyr Arg Ser
325

( 2 ) INFORMATION FOR SEQ ID NO:2:

( i ) SEQUENCE CHARACTERISTICS:
( A ) LENGTH: 329 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

Tyr Arg Asn Leu Gly Lys Ser Gly Leu Arg Val Ser Cys Leu Gly Leu
1 5 10 15

Gly Thr Trp Val Thr Phe Gly Gly Gln Ile Thr Asp Glu Met Ala Glu
20 25 30

His Leu Met Thr Leu Ala Tyr Asp Asn Gly Ile Asn Leu Phe Asp Thr
35 40 45

Ala Glu Val Tyr Ala Ala Gly Lys Ala Glu Val Val Leu Gly Asn Ile
50 55 60

Ile Lys Lys Lys Gly Trp Arg Arg Ser Ser Leu Val Ile Thr Thr Lys
65 70 75 80

Ile Phe Trp Gly Gly Lys Ala Glu Thr Glu Arg Gly Leu Ser Arg Lys
85 90 95

His Ile Ile Glu Gly Leu Lys Ala Ser Leu Glu Arg Leu Gln Leu Glu
100 105 110

Tyr Val Asp Val Val Phe Ala Asn Arg Pro Asp Pro Asn Thr Pro Met
115 120 125

Glu Glu Ile Val Arg Ala Met Thr His Val Ile Asn Gln Gly Met Ala
130 135 140

Met Tyr Trp Gly Thr Ser Arg Trp Ser Ser Met Glu Ile Met Glu Ala
145 150 155 160

Tyr Ser Val Ala Arg Gln Phe Asn Leu Ile Pro Pro Ile Cys Glu Gln
165 170 175

Ala Glu Tyr His Met Phe Gln Arg Glu Lys Val Glu Val Gln Leu Pro
180 185 190

Glu Leu Phe His Lys Ile Gly Val Gly Ala Met Thr Trp Ser Pro Leu
195 200 205

Ala Cys Gly Ile Val Ser Gly Lys Tyr Asp Ser Gly Ile Pro Pro Tyr
210 215 220

Ser Arg Ala Ser Leu Lys Gly Tyr Gln Trp Leu Lys Asp Lys Ile Leu
225 230 235 240

Ser Glu Glu Gly Arg Arg Gln Gln Ala Lys Leu Lys Glu Leu Gln Ala
245 250 255

Ile Ala Glu Arg Leu Gly Cys Thr Leu Pro Gln Leu Ala Ile Ala Trp
260 265 270

Cys Leu Arg Asn Glu Gly Val Ser Ser Val Leu Leu Gly Ala Ser Asn
275 280 285

Ala Glu Gln Leu Met Glu Asn Ile Gly Ala Ile Gln Val Leu Pro Lys
290 295 300

Leu Ser Ser Ser Ile Val His Glu Ile Asp Ser Ile Leu Gly Asn Lys
305 310 315 320

Pro Tyr Ser Lys Lys Asp Tyr Arg Ser
325

( 2 ) INFORMATION FOR SEQ ID NO:3:

( i ) SEQUENCE CHARACTERISTICS:
( A ) LENGTH: 329 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

Tyr Arg Asn Leu Gly Lys Ser Gly Leu Arg Val Ser Cys Leu Gly Leu
1 5 10 15

Gly Thr Trp Val Thr Phe Gly Gly Gln Ile Ser Asp Glu Val Ala Glu
20 25 30

Arg Leu Met Thr Ile Ala Tyr Glu Ser Gly Val Asn Leu Phe Asp Thr
35 40 45

Ala Glu Val Tyr Ala Ala Gly Lys Ala Glu Val Ile Leu Gly Ser Ile
50 55 60

Ile Lys Lys Lys Gly Trp Arg Arg Ser Ser Leu Val Ile Thr Thr Lys
65 70 75 80

Leu Tyr Trp Gly Gly Lys Ala Glu Thr Glu Arg Gly Leu Ser Arg Lys
85 90 95

His Ile Ile Glu Gly Leu Lys Gly Ser Leu Gln Arg Leu Gln Leu Glu
100 105 110

Tyr Val Asp Val Val Phe Ala Asn Arg Pro Asp Ser Asn Thr Pro Met
115 120 125

Glu Glu Ile Val Arg Ala Met Thr His Val Ile Asn Gln Gly Met Ala
130 135 140

Met Tyr Trp Gly Thr Ser Arg Trp Ser Ala Met Glu Ile Met Glu Ala
145 150 155 160

Tyr Ser Val Ala Arg Gln Phe Asn Met Ile Pro Pro Val Cys Glu Gln
165 170 175

Ala Glu Tyr His Leu Phe Gln Arg Glu Lys Val Glu Val Gln Leu Pro
180 185 190

Glu Leu Tyr His Lys Ile Gly Val Gly Ala Met Thr Trp Ser Pro Leu
195 200 205

Ala Cys Gly Ile Ile Ser Gly Lys Tyr Gly Asn Gly Val Pro Glu Ser
210 215 220

Ser Arg Ala Ser Leu Lys Cys Tyr Gln Trp Leu Lys Glu Arg Ile Val
225 230 235 240

Ser Glu Glu Gly Arg Lys Gln Gln Asn Lys Leu Lys Asp Leu Ser Pro
245 250 255

Ile Ala Glu Arg Leu Gly Cys Thr Leu Pro Gln Leu Ala Val Ala Trp
260 265 270

Cys Leu Arg Asn Glu Gly Val Ser Ser Val Leu Leu Gly Ser Ser Thr
275 280 285

Pro Glu Gln Leu Ile Glu Asn Leu Gly Ala Ile Gln Val Leu Pro Lys
290 295 300

Met Thr Ser His Val Val Asn Glu Ile Asp Asn Ile Leu Arg Asn Lys
305 310 315 320

Pro Tyr Ser Lys Lys Asp Tyr Arg Ser
325

( 2 ) INFORMATION FOR SEQ ID NO:4:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

Cys Glu Arg Val Val Ile Asn Val Ser Gly Leu Arg Phe Glu Thr Gln
1 5 10 15

Leu Lys Thr Leu Asn Gln Phe Pro Asp Thr Leu Leu Gly Asn Pro Gln
20 25 30

Lys Arg Asn Arg Tyr Tyr Asp Pro Leu Arg Asn Glu Tyr Phe Phe Asp
35 40 45

Arg Asn Arg Pro Ser Phe Asp Ala Ile Leu Tyr Phe Tyr Gln Ser Gly
50 55 60

Gly Arg Leu Arg Arg Pro Val Asn Val Pro Leu Asp Val Phe Ser Glu
65 70 75 80

Glu Ile Lys Phe Tyr Glu Leu Gly Glu Asn Ala Phe Glu Arg Tyr Arg
85 90 95

Glu Asp Glu Gly Phe Ile Lys Glu Glu Glu Lys Pro Leu Pro Gln Asn
100 105 110

Glu Phe Gln Arg Arg Val Trp Leu Leu Phe Glu Tyr Pro Glu Ser Ser
115 120 125

Ala Ala Ala Arg Leu Cys Ala Ile Phe Ser Val Val Ile Ile Leu Leu
130 135 140

Ser Ile Val Ile Phe Cys Leu Glu
145 150

( 2 ) INFORMATION FOR SEQ ID NO:5:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Cys Glu Arg Val Val Ile Asn Val Ser Gly Leu Arg Phe Glu Thr Gln
1 5 10 15

-continued

Leu Lys Thr Leu Ala Gln Phe Pro Ser Thr Leu Leu Gly Asn Pro Lys
20 25 30

Lys Arg Met Arg Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Arg Arg Pro Val Asn Val Pro Leu Asp Met Phe Ser Glu
65 70 75 80

Glu Ile Lys Phe Tyr Glu Leu Gly Glu Glu Ala Met Glu Lys Phe Arg
85 90 95

Glu Asp Glu Gly Phe Val Lys Glu Glu Glu Arg Pro Leu Pro Asp Lys
100 105 110

Glu Phe Gln Arg Gln Val Trp Leu Leu Phe Glu Phe Pro Glu Ser Ser
115 120 125

Gly Pro Ala Arg Ile Ile Ala Ile Ile Ser Val Met Val Ile Leu Ile
130 135 140

Ser Ile Val Ile Phe Cys Leu Glu
145 150

( 2 ) INFORMATION FOR SEQ ID NO:6:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

Cys Glu Arg Val Val Ile Asn Ile Ser Gly Leu Arg Phe Glu Thr Gln
1 5 10 15

Leu Lys Thr Leu Ser Gln Phe Pro Glu Thr Leu Leu Gly Asp Pro Lys
20 25 30

Lys Arg Met Arg Tyr Phe Asp Pro Leu Arg Asn Glu Tyr Phe Phe Asp
35 40 45

Arg Asn Arg Pro Ser Phe Asp Ala Ile Leu Tyr Phe Tyr Gln Ser Gly
50 55 60

Gly Arg Leu Arg Arg Pro Val Asn Val Pro Leu Asp Ile Phe Ser Glu
65 70 75 80

Glu Ile Arg Phe Tyr Glu Leu Gly Glu Glu Ala Met Glu Ile Phe Arg
85 90 95

Glu Asp Glu Gly Phe Ile Lys Glu Glu Glu Lys Pro Leu Pro Arg Asn
100 105 110

Glu Phe Gln Arg Gln Val Trp Leu Ile Phe Glu Tyr Pro Glu Ser Ser
115 120 125

Gly Ser Ala Arg Ala Ile Ala Ile Val Ser Val Ser Val Ile Leu Ile
130 135 140

Ser Ile Ile Thr Phe Cys Leu Glu
145 150

( 2 ) INFORMATION FOR SEQ ID NO:7:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:7:

Cys Glu Arg Val Val Ile Asn Ile Ser Gly Leu Arg Phe Glu Thr Gln
1 5 10 15

Leu Lys Thr Leu Ala Gln Phe Pro Asn Thr Leu Leu Gly Asn Pro Lys
20 25 30

Lys Arg Met Arg Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Arg Arg Pro Val Asn Val Pro Leu Asp Met Phe Ser Glu
65 70 75 80

Glu Ile Lys Phe Tyr Glu Leu Gly Glu Glu Ala Met Glu Lys Phe Arg
85 90 95

Glu Asp Glu Gly Phe Ile Lys Glu Glu Glu Arg Pro Leu Pro Glu Lys
100 105 110

Glu Tyr Gln Arg Gln Val Trp Leu Leu Phe Glu Tyr Pro Glu Ser Ser
115 120 125

Gly Pro Ala Arg Val Ile Ala Ile Val Ser Val Met Val Ile Leu Ile
130 135 140

Ser Ile Val Ile Phe Cys Leu Glu
145 150

( 2 ) INFORMATION FOR SEQ ID NO:8:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Ser Glu Arg Leu Val Ile Asn Ile Ser Gly Leu Arg Phe Glu Thr Gln
1 5 10 15

Leu Arg Thr Leu Ser Leu Phe Pro Asp Thr Leu Leu Gly Asp Pro Gly
20 25 30

Arg Arg Val Arg Phe Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Arg Arg Pro Val Asn Val Pro Leu Asp Ile Phe Met Glu
65 70 75 80

Glu Ile Arg Phe Tyr Gln Leu Gly Glu Glu Ala Leu Ala Ala Phe Arg
85 90 95

Glu Asp Glu Gly Cys Leu Pro Glu Gly Gly Glu Asp Glu Lys Pro Leu
100 105 110

Pro Ser Gln Pro Phe Gln Arg Gln Val Trp Leu Leu Phe Glu Tyr Pro
115 120 125

Glu Ser Ser Gly Pro Ala Arg Gly Ile Ala Ile Val Ser Val Leu Val
130 135 140

Ile Leu Ile Ser Ile Val Ile Phe Cys Leu Glu
145 150 155

( 2 ) INFORMATION FOR SEQ ID NO:9:

( i ) SEQUENCE CHARACTERISTICS:

-continued ( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

```
Cys Glu Arg Val Val Ile Asn Ile Ser Gly Leu Arg Phe Glu Thr Gln
1               5                   10                  15

Leu Lys Thr Leu Ala Gln Phe Pro Glu Thr Leu Leu Gly Asp Pro Lys
            20                  25                  30

Lys Arg Met Arg Tyr Phe Asp Pro Leu Arg Asn Glu Tyr Phe Phe Asp
        35                  40                  45

Arg Asn Arg Pro Ser Phe Asp Ala Ile Leu Tyr Tyr Tyr Gln Ser Gly
    50                  55                  60

Gly Arg Leu Arg Arg Pro Val Asn Val Pro Leu Asp Ile Phe Ser Glu
65                  70                  75                  80

Glu Ile Arg Phe Tyr Glu Leu Gly Glu Glu Ala Met Glu Met Phe Arg
                85                  90                  95

Glu Asp Glu Gly Tyr Ile Lys Glu Glu Glu Arg Pro Leu Pro Glu Asn
            100                 105                 110

Glu Phe Gln Arg Gln Val Trp Leu Leu Phe Glu Tyr Pro Glu Ser Ser
        115                 120                 125

Gly Pro Ala Arg Ile Ile Ala Ile Val Ser Val Met Val Ile Leu Ile
    130                 135                 140

Ser Ile Val Ser Phe Cys Leu Glu
145                 150
```

( 2 ) INFORMATION FOR SEQ ID NO:10:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

```
Gly Glu Arg Val Val Ile Asn Ile Ser Gly Leu Arg Phe Glu Thr Gln
1               5                   10                  15

Leu Lys Thr Leu Cys Gln Phe Pro Glu Thr Leu Leu Gly Asp Pro Lys
            20                  25                  30

Arg Arg Met Arg Tyr Phe Asp Pro Leu Arg Asn Glu Tyr Phe Phe Asp
        35                  40                  45

Arg Asn Arg Pro Ser Phe Asp Ala Ile Leu Tyr Tyr Tyr Gln Ser Gly
    50                  55                  60

Gly Arg Ile Arg Arg Pro Val Asn Val Pro Ile Asp Ile Phe Ser Glu
65                  70                  75                  80

Glu Ile Arg Phe Tyr Gln Leu Gly Glu Glu Ala Met Glu Lys Phe Arg
                85                  90                  95

Glu Asp Glu Gly Phe Leu Arg Glu Glu Glu Arg Pro Leu Pro Arg Arg
            100                 105                 110

Asp Phe Gln Arg Gln Val Trp Leu Leu Phe Glu Tyr Pro Glu Ser Ser
        115                 120                 125

Gly Pro Ala Arg Gly Ile Ala Ile Val Ser Val Leu Val Ile Leu Ile
    130                 135                 140

Ser Ile Val Ile Phe Cys Leu Glu
```

145 150

(2) INFORMATION FOR SEQ ID NO:11:

(i) SEQUENCE CHARACTERISTICS:
(A) LENGTH: 153 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:11:

```
Cys Glu Arg Val Val Ile Asn Val Ser Gly Leu Arg Phe Glu Thr Gln
  1               5                  10                  15
Met Lys Thr Leu Ala Gln Phe Pro Glu Thr Leu Leu Gly Asp Pro Glu
            20                  25                  30
Lys Arg Thr Gln Tyr Phe Asp Pro Leu Arg Asn Glu Tyr Phe Phe Asp
        35                  40                  45
Arg Asn Arg Pro Ser Phe Asp Ala Ile Leu Tyr Tyr Tyr Gln Ser Gly
    50                  55                  60
Gly Arg Leu Lys Arg Pro Val Asn Val Pro Phe Asp Ile Phe Thr Glu
 65                  70                  75                  80
Glu Val Lys Phe Tyr Gln Leu Gly Glu Glu Ala Leu Leu Lys Phe Arg
                 85                  90                  95
Glu Asp Glu Gly Phe Val Arg Glu Glu Glu Asp Arg Ala Leu Pro Glu
            100                 105                 110
Asn Glu Phe Lys Lys Gln Ile Trp Leu Leu Phe Glu Tyr Pro Glu Ser
        115                 120                 125
Ser Ser Pro Ala Arg Gly Ile Ala Ile Val Ser Val Leu Val Ile Leu
    130                 135                 140
Ile Ser Ile Val Ile Phe Cys Leu Glu
145                 150
```

(2) INFORMATION FOR SEQ ID NO:12:

(i) SEQUENCE CHARACTERISTICS:
(A) LENGTH: 152 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:12:

```
Cys Glu Arg Val Val Ile Asn Ile Ser Gly Leu Arg Phe Glu Thr Gln
  1               5                  10                  15
Leu Lys Thr Leu Ala Gln Phe Pro Glu Thr Leu Leu Gly Asp Pro Lys
            20                  25                  30
Lys Arg Met Arg Tyr Phe Asp Pro Leu Arg Asn Glu Tyr Phe Phe Asp
        35                  40                  45
Arg Asn Arg Pro Ser Phe Asp Ala Ile Leu Tyr Tyr Tyr Gln Ser Gly
    50                  55                  60
Gly Arg Leu Arg Arg Pro Val Asn Val Pro Leu Asp Ile Phe Ser Glu
 65                  70                  75                  80
Glu Ile Arg Phe Tyr Glu Leu Gly Glu Glu Ala Met Glu Met Phe Arg
                 85                  90                  95
Glu Asp Glu Gly Tyr Ile Lys Glu Glu Glu Arg Pro Leu Pro Glu Asn
            100                 105                 110
Glu Phe Gln Arg Gln Val Trp Leu Leu Phe Glu Tyr Pro Glu Ser Ser
```

115 120 125

Gly Pro Ala Arg Ile Ile Ala Ile Val Ser Val Met Val Ile Leu Ile
130 135 140

Ser Ile Val Ser Phe Cys Leu Glu
145 150

( 2 ) INFORMATION FOR SEQ ID NO:13:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:13:

His Gln Arg Val Leu Ile Asn Ile Ser Gly Leu Arg Phe Glu Thr Gln
1 5 10 15

Leu Gly Thr Leu Ala Gln Phe Pro Asn Thr Leu Leu Gly Asp Pro Ala
20 25 30

Lys Arg Leu His Tyr Phe Asp Pro Leu Arg Asn Glu Tyr Phe Phe Asp
35 40 45

Arg Asn Arg Pro Ser Phe Asp Gly Ile Leu Tyr Tyr Tyr Gln Ser Gly
50 55 60

Gly Arg Leu Arg Arg Pro Val Asn Val Ser Leu Asp Val Phe Ala Asp
65 70 75 80

Glu Ile Arg Phe Tyr Gln Leu Gly Asp Glu Ala Met Glu Arg Phe Arg
85 90 95

Glu Asp Glu Gly Phe Ile Lys Glu Glu Glu Lys Pro Leu Pro Arg Asn
100 105 110

Glu Phe Gln Arg Gln Val Trp Leu Ile Phe Glu Tyr Pro Glu Ser Ser
115 120 125

Gly Ser Ala Arg Ala Ile Ala Ile Val Ser Val Leu Val Ile Leu Ile
130 135 140

Ser Ile Ile Thr Phe Cys Leu Glu
145 150

( 2 ) INFORMATION FOR SEQ ID NO:14:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

Ser Glu Arg Leu Val Ile Asn Ile Ser Gly Leu Arg Tyr Glu Thr Gln
1 5 10 15

Leu Arg Thr Leu Ser Leu Phe Pro Asp Thr Leu Leu Gly Asp Pro Gly
20 25 30

Arg Arg Val Arg Phe Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Arg Arg Pro Val Asn Val Pro Leu Asp Ile Phe Met Glu
65 70 75 80

Glu Ile Arg Phe Tyr Gln Leu Gly Asp Glu Ala Leu Ala Ala Phe Arg

-continued 85 90 95

Glu Asp Glu Gly Cys Leu Pro Glu Gly Gly Glu Asp Glu Lys Pro Leu
100 105 110

Pro Ser Gln Pro Phe Gln Arg Gln Val Trp Leu Leu Phe Glu Tyr Pro
115 120 125

Glu Ser Ser Gly Pro Ala Arg Gly Ile Ala Ile Val Ser Val Leu Val
130 135 140

Ile Leu Ile Ser Ile Val Ile Phe Cys Leu Glu
145 150 155

( 2 ) INFORMATION FOR SEQ ID NO:15:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:15:

Gly Glu Arg Val Val Ile Asn Ile Ser Gly Leu Arg Phe Glu Thr Gln
1 5 10 15

Leu Lys Thr Leu Cys Gln Phe Pro Glu Thr Leu Leu Gly Asp Pro Lys
20 25 30

Arg Arg Met Arg Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Ile Arg Arg Pro Val Asn Val Pro Ile Asp Ile Phe Ser Glu
65 70 75 80

Glu Ile Arg Phe Tyr Gln Leu Gly Glu Glu Ala Met Glu Lys Phe Arg
85 90 95

Glu Asp Glu Gly Phe Leu Arg Glu Glu Glu Arg Pro Leu Pro Arg Arg
100 105 110

Asp Phe Gln Arg Gln Val Trp Leu Leu Phe Glu Tyr Pro Glu Ser Ser
115 120 125

Gly Pro Ala Arg Gly Ile Ala Ile Val Ser Val Leu Val Ile Leu Ile
130 135 140

Ser Ile Val Ile Phe Cys Leu Glu
145 150

( 2 ) INFORMATION FOR SEQ ID NO:16:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:16:

Cys Glu Arg Val Val Ile Asn Ile Ser Gly Leu Arg Phe Glu Thr Gln
1 5 10 15

Leu Lys Thr Leu Ala Gln Phe Pro Asn Thr Leu Leu Gly Asn Pro Lys
20 25 30

Lys Arg Met Arg Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly

-continued

```
            50                      55                      60

Gly Arg Leu Arg Arg Pro Val Asn Val Pro Leu Asp Met Phe Ser Glu
 65                     70                      75                  80

Glu Ile Lys Phe Tyr Glu Leu Gly Glu Glu Ala Met Glu Lys Phe Arg
                    85                      90                  95

Glu Asp Glu Gly Phe Ile Lys Glu Glu Glu Arg Pro Leu Pro Glu Lys
                100                     105                 110

Glu Tyr Gln Arg Gln Val Trp Leu Leu Phe Glu Tyr Pro Glu Ser Ser
            115                     120                 125

Gly Pro Ala Arg Val Ile Ala Ile Val Ser Val Met Val Ile Leu Ile
    130                     135                 140

Ser Ile Val Ile Phe Cys Leu Glu
145                     150
```

( 2 ) INFORMATION FOR SEQ ID NO:17:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:17:

```
Ser Glu Arg Leu Val Ile Asn Ile Ser Gly Leu Arg Tyr Glu Thr Gln
  1                   5                  10                  15

Leu Arg Thr Leu Ser Leu Phe Pro Asp Thr Leu Leu Gly Asp Pro Gly
                 20                  25                  30

Arg Arg Val Arg Phe Phe Asp Pro Leu Arg Asn Glu Tyr Phe Phe Asp
             35                  40                  45

Arg Asn Arg Pro Ser Phe Asp Ala Ile Leu Tyr Tyr Tyr Gln Ser Gly
         50                  55                  60

Gly Arg Leu Arg Arg Pro Val Asn Val Pro Leu Asp Ile Phe Met Glu
 65                  70                  75                  80

Glu Ile Arg Phe Tyr Gln Leu Gly Asp Glu Ala Leu Ala Ala Phe Arg
                 85                  90                  95

Glu Asp Glu Gly Cys Leu Pro Glu Gly Gly Glu Asp Glu Lys Pro Leu
                100                 105                 110

Pro Ser Gln Pro Phe Gln Arg Gln Val Trp Leu Leu Phe Glu Tyr Pro
            115                 120                 125

Glu Ser Ser Gly Pro Ala Arg Gly Ile Ala Ile Val Ser Val Leu Val
        130                 135                 140

Ile Leu Ile Ser Ile Val Ile Phe Cys Leu Glu
145                 150                 155
```

( 2 ) INFORMATION FOR SEQ ID NO:18:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:18:

```
Gly Glu Arg Val Val Ile Asn Ile Ser Gly Leu Arg Phe Glu Thr Gln
  1                   5                  10                  15

Leu Lys Thr Leu Cys Gln Phe Pro Glu Thr Leu Leu Gly Asp Pro Lys
```

-continued

```
                        20                                          25                                          30

Arg Arg Met Arg Tyr Phe Asp Pro Leu Arg Asn Glu Tyr Phe Phe Asp
            35                      40                      45

Arg Asn Arg Pro Ser Leu Asp Ala Ile Leu Tyr Tyr Tyr Gln Ser Gly
    50                      55                      60

Gly Arg Ile Arg Arg Pro Val Asn Val Pro Ile Asp Ile Phe Ser Glu
65                      70                      75                      80

Glu Ile Arg Phe Tyr Gln Leu Gly Glu Glu Ala Met Glu Lys Phe Arg
                    85                      90                      95

Glu Asp Glu Gly Phe Leu Arg Glu Glu Glu Arg Pro Leu Pro Arg Arg
            100                     105                     110

Asp Phe Gln Arg Gln Val Trp Leu Leu Phe Glu Tyr Pro Glu Ser Ser
        115                     120                     125

Gly Pro Ala Arg Gly Ile Ala Ile Val Ser Val Leu Val Ile Leu Ile
    130                     135                     140

Ser Ile Val Ile Phe Cys Leu Glu
145                     150
```

( 2 ) INFORMATION FOR SEQ ID NO:19:

( i ) SEQUENCE CHARACTERISTICS:
( A ) LENGTH: 151 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:19:

```
Cys Glu Arg Val Val Ile Asn Val Ser Gly Leu Arg Phe Glu Thr Gln
1               5                   10                  15

Met Lys Thr Leu Ala Gln Phe Pro Glu Thr Leu Leu Gly Asp Pro Glu
            20                  25                  30

Lys Arg Thr Gln Tyr Phe Asp Pro Leu Arg Asn Glu Tyr Phe Phe Asp
        35                  40                  45

Arg Asn Arg Pro Ser Phe Asp Ala Ile Leu Tyr Tyr Tyr Gln Ser Gly
    50                  55                  60

Gly Arg Leu Lys Arg Pro Val Asn Val Pro Phe Asp Ile Phe Thr Glu
65                  70                  75                  80

Glu Val Lys Phe Tyr Gln Leu Gly Glu Glu Ala Leu Leu Lys Phe Arg
                85                  90                  95

Glu Asp Glu Gly Phe Val Arg Glu Glu Glu Asp Arg Ala Leu Pro Glu
            100                 105                 110

Asn Glu Phe Lys Lys Gln Ile Trp Leu Leu Phe Glu Tyr Pro Glu Ser
        115                 120                 125

Ser Ser Pro Ala Arg Ala Ile Ala Ile Val Ser Val Leu Val Ile Leu
    130                 135                 140

Ile Ser Ile Val Ile Phe Cys
145                 150
```

( 2 ) INFORMATION FOR SEQ ID NO:20:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein -continued ( x i ) SEQUENCE DESCRIPTION: SEQ ID NO:20:

```
Gly Glu Arg Val Val Ile Asn Ile Ser Gly Leu Arg Phe Glu Thr Gln
  1               5                  10                  15

Leu Lys Thr Leu Cys Gln Phe Pro Glu Thr Leu Leu Gly Asp Pro Lys
             20                  25                  30

Arg Arg Met Arg Tyr Phe Asp Pro Leu Arg Asn Glu Tyr Phe Phe Asp
         35                  40                  45

Arg Asn Arg Pro Ser Phe Asp Ala Ile Leu Tyr Tyr Tyr Gln Ser Gly
     50                  55                  60

Gly Arg Ile Arg Arg Pro Val Asn Val Pro Ile Asp Ile Phe Ser Glu
 65                  70                  75                  80

Glu Ile Arg Phe Tyr Gln Leu Gly Glu Glu Ala Met Glu Lys Phe Arg
                 85                  90                  95

Glu Asp Glu Gly Phe Leu Arg Glu Glu Glu Arg Pro Leu Pro Glu Asn
            100                 105                 110

Glu Phe Gln Arg Gln Val Trp Leu Leu Phe Glu Tyr Pro Glu Ser Ser
        115                 120                 125

Gly Pro Ala Arg Ile Ile Ala Ile Val Ser Val Met Val Ile Leu Ile
    130                 135                 140

Ser Ile Val Ser Phe Cys Leu Glu
145                 150
```

( 2 ) INFORMATION FOR SEQ ID NO:21:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:21:

```
His Gln Arg Val Leu Ile Asn Ile Ser Gly Leu Arg Phe Glu Ala Gln
  1               5                  10                  15

Leu Gly Thr Leu Ala Gln Phe Pro Asp Thr Leu Leu Gly Asp Pro Ala
             20                  25                  30

Lys Arg Leu Arg Tyr Phe Asp Pro Leu Arg Asn Glu Tyr Phe Phe Asp
         35                  40                  45

Arg Asn Arg Pro Ser Phe Asp Gly Ile Leu Tyr Tyr Tyr Gln Ser Gly
     50                  55                  60

Gly Arg Leu Arg Arg Pro Val Asn Val Ser Leu Asp Val Phe Ala Asp
 65                  70                  75                  80

Glu Ile Arg Phe Tyr Gln Leu Gly Asp Glu Ala Leu Glu Arg Phe Arg
                 85                  90                  95

Glu Asp Glu Gly Tyr Ile Lys Glu Glu Glu Arg Pro Leu Pro Glu Asn
            100                 105                 110

Glu Phe Gln Arg Gln Val Trp Leu Leu Phe Glu Tyr Pro Glu Ser Ser
        115                 120                 125

Gly Pro Ala Arg Ile Ile Ala Ile Val Ser Val Met Val Ile Leu Ile
    130                 135                 140

Ser Ile Val Ser Phe Cys Leu Glu
145                 150
```

( 2 ) INFORMATION FOR SEQ ID NO:22:

( i ) SEQUENCE CHARACTERISTICS:
( A ) LENGTH: 153 amino acids

-continued ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:22:

```
Cys Glu Arg Val Val Ile Asn Val Ser Gly Leu Arg Phe Glu Thr Gln
1               5                   10                  15

Met Lys Thr Leu Ala Gln Phe Pro Glu Thr Leu Leu Gly Asp Pro Glu
            20                  25                  30

Lys Arg Thr Gln Tyr Phe Asp Pro Leu Arg Asn Glu Tyr Phe Phe Asp
        35                  40                  45

Arg Asn Arg Pro Ser Phe Asp Ala Ile Leu Tyr Tyr Tyr Gln Ser Gly
    50                  55                  60

Gly Arg Leu Lys Arg Pro Val Asn Val Pro Phe Asp Ile Phe Thr Glu
65                  70                  75                  80

Glu Val Lys Phe Tyr Gln Leu Gly Glu Glu Ala Leu Leu Lys Phe Arg
                85                  90                  95

Glu Asp Glu Gly Phe Val Arg Glu Glu Glu Asp Arg Ala Leu Pro Glu
            100                 105                 110

Asn Glu Phe Lys Lys Gln Ile Trp Leu Leu Phe Glu Tyr Pro Glu Ser
        115                 120                 125

Ser Ser Pro Ala Arg Gly Ile Ala Ile Val Ser Val Leu Val Ile Leu
    130                 135                 140

Ile Ser Ile Val Ile Phe Cys Leu Glu
145                 150
```

( 2 ) INFORMATION FOR SEQ ID NO:23:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:23:

```
Ser Glu Arg Leu Val Ile Asn Ile Ser Gly Leu Arg Phe Glu Thr Gln
1               5                   10                  15

Leu Arg Thr Leu Ser Leu Phe Pro Asp Thr Leu Leu Gly Asp Pro Gly
            20                  25                  30

Arg Arg Val Arg Phe Phe Asp Pro Leu Arg Asn Glu Tyr Phe Phe Asp
        35                  40                  45

Arg Asn Arg Pro Ser Phe Asp Ala Ile Leu Tyr Tyr Tyr Gln Ser Gly
    50                  55                  60

Gly Arg Leu Arg Arg Pro Val Asn Val Pro Leu Asp Ile Phe Leu Glu
65                  70                  75                  80

Glu Ile Arg Phe Tyr Gln Leu Gly Asp Glu Ala Leu Ala Ala Phe Arg
                85                  90                  95

Glu Asp Glu Gly Cys Leu Pro Glu Gly Gly Glu Asp Glu Lys Pro Leu
            100                 105                 110

Pro Ser Gln Pro Phe Gln Arg Gln Val Trp Leu Leu Phe Glu Tyr Pro
        115                 120                 125

Glu Ser Ser Gly Pro Ala Arg Gly Ile Ala Ile Val Ser Val Leu Val
    130                 135                 140

Ile Leu Ile Ser Ile Val Ile Phe Cys Leu Glu
145                 150                 155
```

-continued ( 2 ) INFORMATION FOR SEQ ID NO:24:

( i ) SEQUENCE CHARACTERISTICS:
( A ) LENGTH: 149 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:24:

```
His Gln Arg Val His Ile Asn Ile Ser Gly Leu Arg Phe Glu Thr Gln
  1               5                  10                  15

Leu Gly Thr Leu Ala Gln Phe Pro Asn Thr Leu Leu Gly Asp Pro Ala
             20                  25                  30

Lys Arg Leu Pro Tyr Phe Asp Pro Leu Arg Asn Glu Tyr Phe Phe Asp
         35                  40                  45

Arg Asn Arg Pro Ser Phe Asp Gly Ile Leu Tyr Tyr Tyr Gln Ser Gly
     50                  55                  60

Gly Arg Leu Arg Gly Val Asn Val Ser Leu Asp Val Phe Ala Asp Glu
 65                  70                  75                  80

Ile Arg Phe Tyr Gln Leu Gly Asp Glu Ala Met Glu Arg Phe Arg Glu
                 85                  90                  95

Asp Glu Gly Phe Ile Lys Glu Glu Glu Lys Pro Leu Pro Arg Asn Glu
            100                 105                 110

Phe Gln Arg Gln Val Trp Leu Ile Phe Glu Tyr Pro Glu Ser Ser Gly
        115                 120                 125

Ser Ala Arg Ala Ile Ala Ile Val Ser Val Leu Val Ile Leu Ile Ser
    130                 135                 140

Ile Ile Thr Phe Cys
145
```

( 2 ) INFORMATION FOR SEQ ID NO:25:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:25:

```
Gly Glu Arg Val Val Ile Asn Ile Ser Gly Val Arg Phe Glu Thr Gln
  1               5                  10                  15

Leu Lys Thr Leu Cys Gln Phe Pro Glu Thr Leu Leu Gly Asp Pro Lys
             20                  25                  30

Arg Arg Met Arg Tyr Phe Asp Pro Leu Arg Asn Glu Tyr Phe Phe Asp
         35                  40                  45

Arg Asn Arg Pro Ser Phe Asp Ala Ile Leu Tyr Tyr Tyr Gln Ser Gly
     50                  55                  60

Gly Arg Ile Arg Arg Pro Val Asn Val Pro Ile Asp Ile Phe Ser Glu
 65                  70                  75                  80

Glu Ile Arg Phe Tyr Gln Leu Gly Glu Glu Ala Met Glu Lys Phe Arg
                 85                  90                  95

Glu Asp Glu Gly Phe Leu Arg Glu Glu Glu Arg Pro Leu Pro Arg Arg
            100                 105                 110

Asp Phe Gln Arg Gln Val Trp Leu Leu Phe Glu Tyr Pro Glu Ser Ser
        115                 120                 125
```

| | | | | | | | | | | | | | | | |
|---|---|---|---|---|---|---|---|---|---|---|---|---|---|---|---|
| Gly | Pro | Ala | Arg | Gly | Ile | Ala | Ile | Val | Ser | Val | Leu | Val | Ile | Leu | Ile |
| | 130 | | | | | 135 | | | | | 140 | | | | |
| Ser | Ile | Val | Ile | Phe | Cys | Leu | Glu | | | | | | | | |
| 145 | | | | | 150 | | | | | | | | | | |

( 2 ) INFORMATION FOR SEQ ID NO:26:

( i ) SEQUENCE CHARACTERISTICS:
( A ) LENGTH: 150 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

| | | | | | | | | | | | | | | | |
|---|---|---|---|---|---|---|---|---|---|---|---|---|---|---|---|
| His | Gln | Arg | Val | His | Ile | Asn | Ile | Ser | Gly | Leu | Arg | Phe | Glu | Thr | Gln |
| 1 | | | | 5 | | | | | 10 | | | | | 15 | |
| Leu | Gly | Thr | Gln | Ala | Gln | Phe | Pro | Asn | Thr | Leu | Leu | Gly | Asp | Pro | Ala |
| | | | 20 | | | | | 25 | | | | | 30 | | |
| Lys | Arg | Leu | Pro | Tyr | Phe | Asp | Pro | Leu | Arg | Asn | Glu | Tyr | Phe | Phe | Asp |
| | | 35 | | | | | 40 | | | | | 45 | | | |
| Arg | Asn | Arg | Pro | Ser | Phe | Asp | Gly | Ile | Leu | Tyr | Tyr | Tyr | Gln | Ser | Gly |
| | 50 | | | | | 55 | | | | | 60 | | | | |
| Gly | Arg | Leu | Arg | Arg | Pro | Val | Asn | Val | Ser | Leu | Asp | Val | Phe | Ala | Asp |
| 65 | | | | | 70 | | | | | 75 | | | | | 80 |
| Glu | Ile | Arg | Phe | Tyr | Gln | Leu | Gly | Asp | Glu | Ala | Met | Glu | Arg | Phe | Gly |
| | | | | 85 | | | | | 90 | | | | | 95 | |
| Glu | Asp | Glu | Gly | Phe | Ile | Lys | Glu | Glu | Glu | Lys | Pro | Leu | Val | Arg | Asn |
| | | | 100 | | | | | 105 | | | | | 110 | | |
| Glu | Phe | Gln | Arg | Gln | Val | Trp | Leu | Ile | Phe | Glu | Tyr | Pro | Glu | Ser | Ser |
| | | 115 | | | | | 120 | | | | | 125 | | | |
| Gly | Ser | Ala | Arg | Ala | Ile | Ala | Ile | Val | Ser | Val | Leu | Val | Ile | Leu | Ile |
| | 130 | | | | | 135 | | | | | 140 | | | | |
| Ser | Ile | Ile | Thr | Phe | Cys | | | | | | | | | | |
| 145 | | | | | 150 | | | | | | | | | | |

( 2 ) INFORMATION FOR SEQ ID NO:27:

( i ) SEQUENCE CHARACTERISTICS:
( A ) LENGTH: 153 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:27:

| | | | | | | | | | | | | | | | |
|---|---|---|---|---|---|---|---|---|---|---|---|---|---|---|---|
| Cys | Glu | Arg | Val | Val | Ile | Asn | Val | Ser | Gly | Leu | Arg | Phe | Glu | Thr | Gln |
| 1 | | | | 5 | | | | | 10 | | | | | 15 | |
| Met | Lys | Thr | Leu | Ala | Gln | Phe | Pro | Glu | Thr | Leu | Leu | Gly | Asp | Pro | Glu |
| | | | 20 | | | | | 25 | | | | | 30 | | |
| Lys | Arg | Thr | Gln | Tyr | Phe | Asp | Pro | Leu | Arg | Asn | Glu | Tyr | Phe | Phe | Asp |
| | | 35 | | | | | 40 | | | | | 45 | | | |
| Arg | Asn | Arg | Pro | Ser | Phe | Asp | Ala | Ile | Leu | Tyr | Tyr | Tyr | Gln | Ser | Gly |
| | 50 | | | | | 55 | | | | | 60 | | | | |
| Gly | Arg | Leu | Lys | Arg | Pro | Val | Asn | Val | Pro | Phe | Asp | Ile | Phe | Thr | Glu |
| 65 | | | | | 70 | | | | | 75 | | | | | 80 |
| Glu | Val | Lys | Phe | Tyr | Gln | Leu | Gly | Glu | Glu | Ala | Leu | Leu | Lys | Phe | Arg |
| | | | | 85 | | | | | 90 | | | | | 95 | |

-continued

Glu Asp Glu Gly Phe Val Arg Glu Glu Glu Asp Arg Ala Leu Pro Glu
100 105 110

Asn Glu Phe Lys Lys Gln Ile Trp Leu Leu Phe Glu Tyr Pro Glu Ser
115 120 125

Ser Asp Pro Ala Arg Gly Ile Ala Ile Val Ser Val Leu Val Ile Leu
130 135 140

Ile Ser Ile Val Ile Phe Cys Leu Glu
145 150

( 2 ) INFORMATION FOR SEQ ID NO:28:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:28:

Gly Glu Arg Val Val Ile Asn Ile Ser Gly Leu Arg Phe Glu Thr Gln
1 5 10 15

Leu Lys Thr Leu Cys Gln Phe Pro Glu Thr Leu Leu Gly Asp Pro Lys
20 25 30

Arg Arg Met Arg Tyr Phe Asp Pro Val Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Ile Arg Arg Pro Val Asn Val Pro Ile Asp Ile Phe Ser Glu
65 70 75 80

Glu Ile Arg Phe Tyr Gln Leu Gly Glu Glu Ala Met Glu Lys Phe Arg
85 90 95

Glu Asp Glu Gly Phe Leu Arg Glu Glu Glu Arg Pro Leu Pro Arg Arg
100 105 110

Asp Phe Gln Arg Gln Val Trp Leu Leu Phe Glu Tyr Pro Glu Ser Ser
115 120 125

Gly Pro Ala Arg Gly Ile Ala Ile Val Ser Val Leu Val Ile Leu Ile
130 135 140

Ser Ile Val Ile Phe Cys Leu Glu
145 150

( 2 ) INFORMATION FOR SEQ ID NO:29:

( i ) SEQUENCE CHARACTERISTICS:
( A ) LENGTH: 150 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:29:

His Gln Arg Val His Ile Asn Ile Ser Gly Leu Arg Phe Glu Thr Gln
1 5 10 15

Leu Gly Thr Leu Ala Gln Phe Pro Asn Thr Leu Leu Gly Asp Pro Ala
20 25 30

Lys Arg Leu Arg Tyr Phe Asp Pro Leu Arg Asn Glu Tyr Phe Phe Asp
35 40 45

Arg Asn Arg Pro Ser Phe Asp Gly Ile Leu Tyr Tyr Tyr Gln Ser Gly
50 55 60

-continued

```
Gly Arg Leu Arg Arg Pro Val Asn Val Ser Leu Asp Val Phe Ala Asp
 65                 70                  75                  80

Glu Ile Arg Phe Tyr Gln Leu Gly Asp Glu Ala Met Glu Arg Phe Arg
                 85                  90                  95

Glu Asp Glu Gly Phe Ile Lys Glu Glu Glu Lys Pro Leu Pro Arg Asn
            100                 105                 110

Glu Phe Gln Arg Gln Val Trp Leu Ile Phe Glu Tyr Pro Glu Ser Ser
        115                 120                 125

Gly Ser Ala Arg Ala Ile Ala Ile Val Ser Val Leu Val Ile Leu Ile
    130                 135                 140

Ser Ile Ile Thr Phe Cys
145                 150
```

( 2 ) INFORMATION FOR SEQ ID NO:30:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:30:

```
Cys Glu Arg Val Val Ile Asn Ile Ser Gly Leu Arg Phe Glu Thr Gln
  1               5                  10                  15

Leu Lys Thr Leu Ala Gln Phe Pro Asn Thr Leu Leu Gly Asn Pro Lys
             20                  25                  30

Lys Arg Met Arg Tyr Phe Asp Pro Leu Arg Asn Glu Tyr Phe Phe Asp
         35                  40                  45

Arg Asn Arg Pro Ser Phe Asp Ala Ile Leu Tyr Tyr Tyr Gln Ser Gly
     50                  55                  60

Gly Arg Leu Arg Arg Pro Val Asn Val Pro Leu Asp Met Phe Ser Glu
 65                 70                  75                  80

Glu Ile Lys Phe Tyr Glu Leu Gly Glu Glu Ala Met Glu Lys Phe Arg
                 85                  90                  95

Glu Asp Glu Gly Phe Ile Lys Glu Glu Glu Arg Pro Leu Pro Glu Lys
            100                 105                 110

Glu Tyr Gln Arg Gln Val Trp Leu Leu Phe Glu Tyr Pro Glu Ser Ser
        115                 120                 125

Gly Pro Ala Arg Val Ile Ala Ile Val Ser Val Met Val Ile Leu Ile
    130                 135                 140

Ser Ile Val Ile Phe Cys Leu Glu
145                 150
```

( 2 ) INFORMATION FOR SEQ ID NO:31:

( i ) SEQUENCE CHARACTERISTICS:
( A ) LENGTH: 153 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:31:

```
Cys Glu Arg Val Val Ile Asn Val Ser Gly Leu Arg Phe Glu Thr Gln
  1               5                  10                  15

Met Lys Thr Leu Ala Gln Phe Pro Glu Thr Leu Leu Gly Asp Pro Glu
             20                  25                  30
```

-continued

Lys Arg Thr Gln Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Lys Arg Pro Val Asn Val Pro Phe Asp Ile Phe Thr Glu
65 70 75 80

Glu Val Lys Phe Tyr Gln Leu Gly Glu Glu Ala Leu Leu Lys Phe Arg
85 90 95

Glu Asp Glu Gly Phe Val Arg Glu Glu Glu Asp Arg Ala Leu Pro Glu
100 105 110

Asn Glu Phe Lys Lys Gln Ile Trp Leu Leu Phe Glu Tyr Pro Glu Ser
115 120 125

Ser Ser Pro Ala Arg Gly Ile Ala Ile Val Ser Val Leu Val Ile Leu
130 135 140

Ile Ser Ile Val Ile Phe Cys Leu Glu
145 150

( 2 ) INFORMATION FOR SEQ ID NO:32:

( i ) SEQUENCE CHARACTERISTICS:
( A ) LENGTH: 152 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:32:

Cys Glu Arg Val Val Ile Asn Ile Ser Gly Leu Arg Phe Glu Thr Gln
1 5 10 15

Leu Lys Thr Leu Ala Gln Phe Pro Glu Thr Leu Leu Gly Asp Pro Lys
20 25 30

Lys Arg Met Arg Tyr Phe Asp Pro Leu Arg Asn Glu Tyr Phe Phe Asp
35 40 45

Arg Asn Arg Pro Ser Phe Asp Ala Ile Leu Tyr Tyr Tyr Gln Ser Gly
50 55 60

Gly Arg Leu Arg Arg Pro Val Asn Val Pro Leu Asp Ile Phe Ser Glu
65 70 75 80

Glu Ile Arg Phe Tyr Glu Leu Gly Glu Glu Ala Met Glu Met Phe Arg
85 90 95

Glu Asp Glu Gly Tyr Ile Lys Glu Glu Glu Arg Pro Leu Pro Glu Asn
100 105 110

Glu Phe Gln Arg Gln Val Trp Leu Leu Phe Glu Tyr Pro Glu Ser Ser
115 120 125

Gly Pro Ala Arg Ile Ile Ala Ile Val Ser Val Met Val Ile Leu Ile
130 135 140

Ser Ile Val Ser Phe Cys Leu Glu
145 150

( 2 ) INFORMATION FOR SEQ ID NO:33:

( i ) SEQUENCE CHARACTERISTICS:
( A ) LENGTH: 179 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:33:

-continued

Ser Arg Arg Val Arg Leu Asn Val Gly Gly Leu Ala His Glu Val Leu
1 5 10 15

Trp Arg Thr Leu Asp Arg Leu Pro Arg Thr Arg Leu Gly Lys Leu Arg
20 25 30

Asp Cys Asn Thr His Asp Ser Leu Leu Gln Val Cys Asp Asp Tyr Ser
35 40 45

Leu Glu Asp Asn Glu Tyr Phe Phe Asp Arg His Pro Gly Ala Phe Thr
50 55 60

Ser Ile Leu Asn Phe Tyr Arg Thr Gly Arg Leu His Met Met Glu Glu
65 70 75 80

Met Cys Ala Leu Ser Phe Ser Gln Glu Leu Asp Tyr Trp Gly Ile Asp
85 90 95

Glu Ile Tyr Leu Glu Ser Cys Cys Gln Ala Arg Tyr His Gln Lys Lys
100 105 110

Glu Gln Met Asn Glu Glu Leu Lys Arg Glu Ala Glu Thr Leu Arg Glu
115 120 125

Arg Glu Gly Glu Glu Phe Asp Asn Thr Cys Cys Ala Glu Lys Arg Lys
130 135 140

Lys Leu Trp Asp Leu Leu Glu Lys Pro Asn Ser Ser Val Ala Ala Lys
145 150 155 160

Ile Leu Ala Ile Ile Ser Ile Met Phe Ile Val Leu Ser Thr Ile Ala
165 170 175

Leu Ser Leu ( 2 ) INFORMATION FOR SEQ ID NO:34:

( i ) SEQUENCE CHARACTERISTICS:
( A ) LENGTH: 179 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:34:

Ser Arg Arg Val Lys Ile Asn Val Gly Gly Leu Asn His Glu Val Leu
1 5 10 15

Trp Arg Thr Leu Asp Arg Leu Pro Arg Thr Arg Leu Gly Lys Leu Arg
20 25 30

Asp Cys Asn Thr His Glu Ser Leu Leu Glu Val Cys Asp Asp Tyr Asn
35 40 45

Leu Asn Glu Asn Glu Tyr Phe Phe Asp Arg His Pro Gly Ala Phe Thr
50 55 60

Ser Ile Leu Asn Phe Tyr Arg Thr Gly Lys Leu His Met Met Glu Glu
65 70 75 80

Met Cys Ala Leu Ser Phe Gly Gln Glu Leu Asp Tyr Trp Gly Ile Asp
85 90 95

Glu Ile Tyr Leu Glu Ser Cys Cys Gln Ala Arg Tyr His Gln Lys Lys
100 105 110

Glu Gln Met Asn Glu Glu Leu Arg Arg Glu Ala Glu Thr Met Arg Asp
115 120 125

Gly Glu Gly Glu Glu Phe Asp Asn Thr Cys Cys Pro Glu Lys Arg Lys
130 135 140

Lys Leu Trp Asp Leu Leu Glu Lys Pro Asn Ser Ser Val Ala Ala Lys
145 150 155 160

Ile Leu Ala Ile Val Ser Ile Leu Phe Ile Val Leu Ser Thr Ile Ala

-continued 165 170 175

Leu Ser Leu ( 2 ) INFORMATION FOR SEQ ID NO:35:

( i ) SEQUENCE CHARACTERISTICS:
( A ) LENGTH: 179 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:35:

Ser Arg Arg Val Arg Leu Asn Val Gly Gly Leu Ala His Glu Val Leu
1 5 10 15

Trp Arg Thr Leu Asp Arg Leu Pro Arg Thr Arg Leu Gly Lys Leu Arg
20 25 30

Asp Cys Asn Thr His Asp Ser Leu Leu Glu Val Cys Asp Asp Tyr Ser
35 40 45

Leu Asp Asp Asn Glu Tyr Phe Phe Asp Arg His Pro Gly Ala Phe Thr
50 55 60

Ser Ile Leu Asn Phe Tyr Arg Thr Gly Arg Leu His Met Met Glu Glu
65 70 75 80

Met Cys Ala Leu Ser Phe Ser Gln Glu Leu Asp Tyr Trp Gly Ile Asp
85 90 95

Glu Ile Tyr Leu Glu Ser Cys Cys Gln Ala Arg Tyr His Gln Lys Lys
100 105 110

Glu Gln Met Asn Glu Glu Leu Lys Arg Glu Ala Glu Thr Leu Arg Glu
115 120 125

Arg Glu Gly Glu Glu Phe Asp Asn Thr Cys Cys Ala Glu Lys Arg Lys
130 135 140

Lys Leu Trp Asp Leu Leu Glu Lys Pro Asn Ser Ser Val Ala Ala Lys
145 150 155 160

Ile Leu Ala Ile Ile Ser Ile Met Phe Ile Val Leu Ser Thr Ile Ala
165 170 175

Leu Ser Leu ( 2 ) INFORMATION FOR SEQ ID NO:36:

( i ) SEQUENCE CHARACTERISTICS:
( A ) LENGTH: 179 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

Ser Arg Arg Val Arg Leu Asn Val Gly Gly Leu Ala His Glu Val Leu
1 5 10 15

Trp Arg Thr Leu Asp Arg Leu Pro Arg Thr Arg Leu Gly Lys Leu Arg
20 25 30

Asp Cys Asn Thr His Asp Ser Leu Leu Glu Val Cys Asp Asp Tyr Ser
35 40 45

Leu Asp Asp Asn Glu Tyr Phe Phe Asp Arg His Pro Gly Ala Phe Thr
50 55 60

Ser Ile Leu Asn Phe Tyr Arg Thr Gly Arg Leu His Met Met Glu Glu
65 70 75 80

-continued

Met Cys Ala Leu Ser Phe Ser Gln Glu Leu Asp Tyr Trp Gly Ile Asp
85 90 95

Glu Ile Tyr Leu Glu Ser Cys Cys Gln Ala Arg Tyr His Gln Lys Lys
100 105 110

Glu Gln Met Asn Glu Glu Leu Lys Arg Glu Ala Glu Thr Leu Arg Glu
115 120 125

Arg Glu Gly Glu Glu Phe Asp Asn Thr Cys Cys Ala Glu Lys Arg Lys
130 135 140

Lys Leu Trp Asp Leu Leu Glu Lys Pro Asn Ser Ser Val Ala Ala Lys
145 150 155 160

Ile Leu Ala Ile Ile Ser Ile Met Phe Ile Val Leu Ser Thr Ile Ala
165 170 175

Leu Ser Leu ( 2 ) INFORMATION FOR SEQ ID NO:37:

( i ) SEQUENCE CHARACTERISTICS:
( A ) LENGTH: 190 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:37:

Ser Gly Lys Ile Val Ile Asn Val Gly Gly Val Arg His Glu Thr Tyr
1 5 10 15

Arg Ser Thr Leu Arg Thr Leu Pro Gly Thr Arg Leu Ala Gly Leu Thr
20 25 30

Glu Pro Glu Ala Ala Ala Arg Phe Asp Tyr Asp Pro Gly Thr Asp Glu
35 40 45

Phe Phe Phe Asp Arg His Pro Gly Val Phe Ala Tyr Val Leu Asn Tyr
50 55 60

Tyr Arg Thr Gly Lys Leu His Cys Pro Ala Asp Val Cys Gly Pro Leu
65 70 75 80

Phe Glu Glu Glu Leu Gly Phe Trp Gly Ile Asp Glu Thr Asp Val Glu
85 90 95

Ala Cys Cys Trp Met Thr Tyr Arg Gln His Arg Asp Ala Glu Glu Ala
100 105 110

Leu Asp Ser Phe Glu Ala Pro Asp Ser Ser Ala Asn Ala Asn Ala Asn
115 120 125

Ala Gly Gly Ala His Asp Ala Gly Leu Asp Asp Glu Ala Gly Ala Gly
130 135 140

Gly Gly Gly Leu Asp Gly Ala Gly Gly Glu Leu Lys Arg Leu Cys Phe
145 150 155 160

Gln Asp Ala Gly Gly Gly Ala Gly Asp Leu Pro Gly Ala Arg Ala Ala
165 170 175

Gly Ala Thr Trp Trp Arg Arg Trp Gln Pro Arg Val Trp Ala
180 185 190

( 2 ) INFORMATION FOR SEQ ID NO:38:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:38:

Asn Glu Arg Val Ile Leu Asn Val Gly Gly Thr Arg His Glu Thr Tyr
1 5 10 15

Arg Ser Thr Leu Lys Thr Leu Pro Gly Thr Arg Leu Ala Leu Leu Ala
20 25 30

( 2 ) INFORMATION FOR SEQ ID NO:39:

( i ) SEQUENCE CHARACTERISTICS:
( A ) LENGTH: 149 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:39:

Gly Gly Gly Arg Glu Phe Phe Phe Asp Arg His Pro Gly Val Phe Ala
1 5 10 15

Tyr Val Leu Asn Tyr Tyr Arg Thr Gly Lys Leu His Cys Pro Ala Asp
20 25 30

Val Cys Gly Pro Leu Phe Glu Glu Glu Leu Ala Phe Trp Gly Ile Asp
35 40 45

Glu Thr Asp Val Glu Pro Cys Cys Trp Met Thr Tyr Arg Gln His Arg
50 55 60

Asp Ala Glu Glu Ala Leu Asp Ile Phe Glu Thr Pro Asp Leu Ile Gly
65 70 75 80

Gly Asp Pro Gly Asp Asp Glu Asp Leu Gly Gly Lys Arg Leu Gly Ile
85 90 95

Glu Asp Ala Ala Gly Leu Gly Gly Pro Asp Gly Lys Ser Gly Arg Trp
100 105 110

Arg Lys Leu Gln Pro Arg Met Trp Ala Leu Phe Glu Asp Pro Tyr Ser
115 120 125

Ser Arg Ala Ala Arg Phe Ile Ala Phe Ala Ser Leu Phe Phe Ile Leu
130 135 140

Val Ser Ile Thr Thr
145

( 2 ) INFORMATION FOR SEQ ID NO:40:

( i ) SEQUENCE CHARACTERISTICS:
( A ) LENGTH: 208 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:40:

Ser Gly Lys Ile Val Ile Asn Val Gly Gly Val Arg His Glu Thr Tyr
1 5 10 15

Arg Ser Thr Leu Arg Thr Leu Pro Gly Thr Arg Leu Ala Gly Leu Thr
20 25 30

Glu Pro Glu Ala Ala Ala Arg Phe Asp Tyr Asp Pro Gly Thr Asp Glu
35 40 45

Phe Phe Phe Asp Arg His Pro Gly Val Phe Ala Tyr Val Leu Asn Tyr
50 55 60

Tyr Arg Thr Gly Lys Leu His Cys Pro Ala Asp Val Cys Gly Pro Leu
65 70 75 80

Phe Glu Glu Glu Leu Gly Phe Trp Gly Ile Asp Glu Thr Asp Val Glu

```
                          85                       90                       95

Ala Cys Cys Trp Met Thr Tyr Arg Gln His Arg Asp Ala Glu Glu Ala
            100                 105                 110

Leu Asp Ser Phe Glu Ala Pro Asp Ser Ser Gly Asn Ala Asn Ala Asn
        115                 120                 125

Ala Gly Gly Ala His Asp Ala Gly Leu Asp Asp Glu Ala Gly Ala Gly
    130                 135                 140

Gly Gly Gly Leu Asp Gly Ala Gly Gly Glu Leu Lys Arg Leu Cys Phe
145                 150                 155                 160

Gln Asp Ala Gly Gly Gly Ala Gly Gly Pro Ala Gly Gly Pro Gly Gly
                165                 170                 175

Ala Gly Gly Thr Trp Trp Arg Arg Trp Gln Pro Arg Val Trp Ala Leu
            180                 185                 190

Phe Glu Asp Pro Tyr Ser Ser Arg Ala Ala Arg Tyr Val Ala Phe Ala
        195                 200                 205
```

( 2 ) INFORMATION FOR SEQ ID NO:41:

( i ) SEQUENCE CHARACTERISTICS:
( A ) LENGTH: 208 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:41:

```
Ser Glu Lys Ile Ile Ile Asn Val Gly Gly Thr Arg His Glu Thr Tyr
1               5                   10                  15

Arg Ser Thr Leu Arg Thr Leu Pro Gly Thr Arg Leu Ala Trp Leu Ala
            20                  25                  30

Asp Pro Asp Gly Gly Gly Arg Pro Glu Ser Asp Gly Gly Gly Ala Gly
        35                  40                  45

Ser Ser Gly Ser Ser Gly Gly Gly Gly Gly Cys Glu Phe Phe Phe Asp
    50                  55                  60

Arg His Pro Gly Val Phe Ala Tyr Val Leu Asn Tyr Tyr Arg Thr Gly
65                  70                  75                  80

Lys Leu His Cys Pro Ala Asp Val Cys Gly Pro Leu Phe Glu Glu Glu
                85                  90                  95

Leu Thr Phe Trp Gly Ile Asp Glu Thr Asp Val Glu Pro Cys Cys Trp
            100                 105                 110

Met Thr Tyr Arg Gln His Arg Asp Ala Glu Glu Ala Leu Asp Ile Phe
        115                 120                 125

Glu Ser Pro Asp Gly Gly Gly Gly Gly Ala Gly Pro Gly Asp Glu Ala
    130                 135                 140

Gly Asp Asp Glu Arg Glu Leu Ala Leu Gln Arg Leu Gly Pro His Glu
145                 150                 155                 160

Gly Gly Ser Gly Pro Gly Ala Gly Ser Gly Gly Cys Arg Gly Trp Gln
                165                 170                 175

Pro Arg Met Trp Ala Leu Phe Glu Asp Pro Tyr Ser Ser Arg Ala Ala
            180                 185                 190

Arg Val Val Ala Phe Ala Ser Leu Phe Phe Ile Leu Val Ser Ile Thr
        195                 200                 205
```

( 2 ) INFORMATION FOR SEQ ID NO:42:

( i ) SEQUENCE CHARACTERISTICS:
( A ) LENGTH: 200 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:42:

Ser Glu Arg Ile Val Ile Asn Val Gly Gly Thr Arg His Gln Thr Tyr
1 5 10 15

Arg Ser Thr Leu Arg Thr Leu Pro Gly Thr Arg Leu Ala Trp Leu Ala
20 25 30

Glu Pro Asp Ala His Ser His Phe Asp Tyr Asp Pro Arg Ala Asp Glu
35 40 45

Phe Phe Phe Asp Arg His Pro Gly Val Phe Ala His Ile Leu Asn Tyr
50 55 60

Tyr Arg Thr Gly Lys Leu His Cys Pro Ala Asp Val Cys Gly Pro Leu
65 70 75 80

Tyr Glu Glu Glu Leu Ala Phe Trp Gly Ile Asp Glu Thr Asp Val Glu
85 90 95

Pro Cys Cys Trp Met Thr Tyr Arg Gln His Arg Asp Ala Glu Glu Ala
100 105 110

Leu Asp Ser Phe Gly Gly Ala Pro Leu Asp Asn Ser Ala Asp Asp Ala
115 120 125

Asp Ala Asp Gly Pro Gly Asp Ser Gly Asp Gly Glu Asp Glu Leu Glu
130 135 140

Met Thr Lys Arg Leu Ala Leu Ser Asp Ser Pro Asp Gly Arg Pro Gly
145 150 155 160

Gly Phe Trp Arg Arg Trp Gln Pro Arg Ile Trp Ala Leu Phe Glu Asp
165 170 175

Pro Tyr Ser Ser Arg Tyr Ala Arg Tyr Val Ala Phe Ala Ser Leu Phe
180 185 190

Phe Ile Leu Val Ser Ile Thr Thr
195 200

( 2 ) INFORMATION FOR SEQ ID NO:43:

( i ) SEQUENCE CHARACTERISTICS:
( A ) LENGTH: 208 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:43:

Ser Glu Lys Ile Ile Ile Asn Val Gly Gly Thr Arg His Glu Thr Tyr
1 5 10 15

Arg Ser Thr Leu Arg Thr Leu Pro Gly Thr Arg Leu Ala Trp Leu Ala
20 25 30

Asp Pro Asp Gly Gly Gly Arg Pro Glu Thr Asp Gly Gly Gly Val Gly
35 40 45

Ser Ser Gly Thr Ser Gly Gly Gly Gly Cys Glu Phe Phe Phe Asp Arg
50 55 60

His Pro Gly Val Phe Ala Tyr Val Leu Asn Tyr Tyr Arg Thr Gly Lys
65 70 75 80

Leu His Cys Pro Ala Asp Val Cys Gly Pro Leu Phe Glu Glu Glu Leu
85 90 95

Thr Phe Trp Gly Ile Asp Glu Thr Asp Val Glu Pro Cys Cys Trp Met
100 105 110

-continued

Thr Tyr Arg Gln His Arg Asp Ala Glu Glu Ala Leu Asp Ile Phe Glu
115 120 125

Ser Pro Asp Gly Gly Gly Ser Gly Ala Gly Pro Ser Asp Glu Ala Gly
130 135 140

Asp Asp Glu Arg Glu Leu Ala Leu Gln Arg Leu Gly Pro His Glu Gly
145 150 155 160

Gly Ala Gly His Gly Ala Gly Ser Gly Gly Cys Arg Gly Trp Gln Pro
165 170 175

Arg Met Trp Ala Leu Phe Glu Asp Pro Tyr Ser Ser Arg Ala Ala Arg
180 185 190

Val Val Ala Phe Ala Ser Leu Phe Phe Ile Leu Val Ser Ile Thr Thr
195 200 205

( 2 ) INFORMATION FOR SEQ ID NO:44:

( i ) SEQUENCE CHARACTERISTICS:
( A ) LENGTH: 162 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:44:

Asp Glu Val Leu Val Val Asn Val Ser Gly Arg Arg Phe Glu Thr Trp
1 5 10 15

Lys Asn Thr Leu Asp Arg Tyr Pro Asp Thr Leu Leu Gly Ser Ser Glu
20 25 30

Lys Glu Phe Phe Tyr Asp Ala Glu Ser Gly Glu Tyr Phe Phe Asp Arg
35 40 45

Asp Pro Asp Met Phe Arg His Val Leu Asn Phe Tyr Arg Thr Gly Arg
50 55 60

Leu His Cys Pro Arg Gln Glu Cys Ile Gln Ala Phe Asp Glu Glu Leu
65 70 75 80

Ala Phe Tyr Gly Leu Val Pro Glu Leu Val Gly Asp Cys Cys Leu Glu
85 90 95

Glu Tyr Arg Asp Arg Lys Lys Glu Asn Ala Glu Arg Leu Ala Glu Asp
100 105 110

Glu Glu Ala Glu Gln Ala Gly Glu Gly Pro Ala Leu Pro Ala Gly Ser
115 120 125

Ser Leu Arg Gln Arg Leu Trp Arg Ala Phe Glu Asn Pro His Thr Ser
130 135 140

Thr Ala Ala Leu Val Phe Tyr Tyr Val Thr Gly Phe Phe Ile Ala Val
145 150 155 160

Ser Val ( 2 ) INFORMATION FOR SEQ ID NO:45:

( i ) SEQUENCE CHARACTERISTICS:
( A ) LENGTH: 159 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:45:

Asp Ala Leu Ile Val Leu Asn Val Ser Gly Thr Arg Phe Gln Thr Trp
1 5 10 15

-continued

| | | | | | | | | | | | | | | | |
|---|---|---|---|---|---|---|---|---|---|---|---|---|---|---|---|
| Gln | Asp | Thr | Leu<br>20 | Glu | Arg | Tyr | Pro | Asp<br>25 | Thr | Leu | Leu | Gly | Ser<br>30 | Ser | Glu |
| Arg | Asp | Phe<br>35 | Phe | Tyr | His | Pro | Glu<br>40 | Thr | Gln | Gln | Tyr | Phe<br>45 | Phe | Asp | Arg |
| Asp | Pro<br>50 | Asp | Ile | Phe | Arg | His<br>55 | Ile | Leu | Asn | Phe | Tyr<br>60 | Arg | Thr | Gly | Leu |
| His<br>65 | Tyr | Pro | Arg | His | Glu<br>70 | Cys | Ile | Ser | Ala | Tyr<br>75 | Asp | Glu | Glu | Leu | Ala<br>80 |
| Phe | Phe | Gly | Leu | Ile<br>85 | Pro | Glu | Ile | Ile | Gly<br>90 | Asp | Cys | Cys | Tyr | Glu<br>95 | Glu |
| Tyr | Lys | Asp | Arg<br>100 | Arg | Arg | Glu | Asn | Ala<br>105 | Glu | Arg | Leu | Gln | Asp<br>110 | Asp | Ala |
| Asp | Thr | Asp<br>115 | Asn | Thr | Gly | Glu | Ser<br>120 | Ala | Leu | Pro | Thr | Met<br>125 | Thr | Ala | Arg |
| Gln | Arg<br>130 | Val | Trp | Arg | Ala | Phe<br>135 | Glu | Asn | Pro | His | Thr<br>140 | Ser | Thr | Met | Ala |
| Leu<br>145 | Val | Phe | Tyr | Tyr | Val<br>150 | Thr | Gly | Phe | Phe | Ile<br>155 | Ala | Val | Ser | Val | |

What is claimed is:

1. An isolated or purified nucleic acid which encodes a polypeptide, said polypeptide consisting of a core region of a β-subunit of a Shaker-like potassium ion channel as set forth in SEQ ID NO:1, wherein said polypeptide is incapable of accelerating the inactivation of an active α-subunit of a Shaker-like potassium ion channel.

2. An expression vector comprising the nucleic acid of claim 1.

3. A method of modulating the flow of potassium ions through a cell membrane surrounding a cytoplasm of a cell having Shaker-like potassium ion channels in vitro comprising introducing into the cell a promoter and, operably linked thereto, the nucleic acid of claim 1, such that the polypeptide encoded by said nucleic acid is expressed and inhibits the inactivation of an active potassium ion channel.

4. An isolated or purified nucleic acid which encodes a polypeptide, said polypeptide consisting of a core region of a β-subunit of a Shaker-like potassium ion channel as set forth in SEQ ID NO:2, wherein said polypeptide is incapable of accelerating the inactivation of an active α-subunit of a Shaker-like potassium ion channel.

5. An expression vector comprising the nucleic acid of claim 4.

6. A method of modulating the flow of potassium ions through a cell membrane surrounding a cytoplasm of a cell having Shaker-like potassium ion channels in vitro comprising introducing into the cell a promoter and, operably linked thereto, the nucleic acid of claim 4, such that the polypeptide encoded by said nucleic acid is expressed and inhibits the inactivation of an active potassium ion channel.

* * * * *